(12) United States Patent
Kim et al.

(10) Patent No.: US 9,523,683 B2
(45) Date of Patent: Dec. 20, 2016

(54) FUNCTIONALIZED POLYDIACETYLENE SENSORS

(71) Applicant: The Regents of the University of Michigan, Ann Arbor, MI (US)

(72) Inventors: Jinsang Kim, Ann Arbor, MI (US); Jiseok Lee, Ann Arbor, MI (US)

(73) Assignee: The Regents Of The University of Michigan, Ann Arbor, MI (US)

( * ) Notice: Subject to any disclaimer, the term of this patent is extended or adjusted under 35 U.S.C. 154(b) by 183 days.

(21) Appl. No.: 14/157,670

(22) Filed: Jan. 17, 2014

(65) Prior Publication Data

US 2015/0268232 A1 Sep. 24, 2015

Related U.S. Application Data

(62) Division of application No. 12/714,024, filed on Feb. 26, 2010, now Pat. No. 8,633,140.

(60) Provisional application No. 61/156,124, filed on Feb. 27, 2009.

(51) Int. Cl.

| | | |
|---|---|---|
| *G01N 33/542* | (2006.01) | |
| *G01N 33/543* | (2006.01) | |
| *C07C 233/20* | (2006.01) | |
| *C07C 233/49* | (2006.01) | |
| *C07C 233/55* | (2006.01) | |
| *C07C 251/48* | (2006.01) | |
| *C07D 251/30* | (2006.01) | |
| *C07H 21/00* | (2006.01) | |
| *C40B 40/04* | (2006.01) | |
| *C40B 80/00* | (2006.01) | |
| *G01N 33/52* | (2006.01) | |
| *G01N 33/58* | (2006.01) | |

(52) U.S. Cl.
CPC ......... *G01N 33/5432* (2013.01); *C07C 233/20* (2013.01); *C07C 233/49* (2013.01); *C07C 233/55* (2013.01); *C07C 251/48* (2013.01); *C07D 251/30* (2013.01); *C07H 21/00* (2013.01); *C40B 40/04* (2013.01); *C40B 80/00* (2013.01); *G01N 33/52* (2013.01); *G01N 33/542* (2013.01); *G01N 33/582* (2013.01); *C07B 2200/11* (2013.01)

(58) Field of Classification Search
None
See application file for complete search history.

(56) References Cited

PUBLICATIONS

Lee et al (2008 Macromolecular Research 16:73-5; published on the web Jan. 2008).*
Kim et al (2008 Advanced Materials 20:1117-21).*
Lee et al (2009 Advanced Materials 21:3674-7).*
Kim et al 2008 PMSE preprints 98:22-23.*

* cited by examiner

*Primary Examiner* — Christopher M Gross
(74) *Attorney, Agent, or Firm* — Harness, Dickey & Pierce, PLC

(57) ABSTRACT

A microarray includes a solid substrate having a surface, the surface having a plurality of binding spots and a plurality of reaction moieties bound to the binding spots. A reaction moiety includes a plurality of polyacetylene monomers, the polyacetylene monomers having a first coupling region and a second coupling region, the first coupling region having a first functional group operable to bind to the binding spot and the second coupling region comprising a second functional group operable to bind to an accessory molecule; and an accessory molecule having a binding region and an analyte reaction region, the analyte reaction region operable to selectively bind to the target analyte, and the binding region operable to bind to the second coupling region of the polyacetylene monomer. Upon binding a target analyte with the reaction moiety, a color change from the polyacetylene monomer occurs and the reaction moiety produces fluorescence.

15 Claims, 31 Drawing Sheets

FUNCTIONALIZED POLYDIACETYLENE SENSORS

CROSS-REFERENCE TO RELATED APPLICATIONS

This application claims the benefit of U.S. Provisional Application No. 61/156,124, filed on Feb. 27, 2009. The entire disclosure of the above application is incorporated herein by reference.

GOVERNMENT RIGHTS

This invention was made with government support under Grant No. DMR0644864 awarded by the National Science Foundation. The U.S. Government has certain rights in the invention.

REFERENCE TO A SEQUENCE LISTING

The material in the ASCII text file titled "2115004304USDVA_SEQLST.txt" is hereby incorporated by reference in its entirety. The ASCII text file titled "2115004304USDVA_SEQLST.txt" was created on Mar. 31, 2014 and the size is 724 bytes.

FIELD

The present disclosure relates to sensors, microarrays, liposomes, and nanoparticles including diacetylene constructs with fluorescence and target sensing capabilities.

INTRODUCTION

This section provides background information related to the present disclosure which is not necessarily prior art.

Molecular sensors are used to detect chemical species with high selectivity on the basis of molecular recognition rather than the physical properties of a target or analyte. Many types of sensing devices have been developed, including enzyme electrodes, optical immunosensors, ligand-receptor amperometers, and evanescent-wave probes. Detection methods using such sensors can involve changes in properties such as conductivity, absorbance, luminescence, fluorescence, and the like. Various sensors rely upon a direct binding event between a target molecule or analyte and a signaling agent in order to produce a measurable change in a property such as fluorescence. Difficulties with sensors often relate to the size of the signal event, which can make actual detection of the signal difficult and can affect the selectivity and make the sensor subject to false readings.

Molecular sensors can employ fluorescent labeling. The phenomenon of fluorescence is distinct from absorbance properties that give systems their color. In order to be fluorescent, the system absorbs one wavelength of light and then emits another. Upon absorbing the light, the system is excited to a higher energy state. It can then return to the ground or resting state by a variety of mechanisms, most of which do not lead to fluorescence. These alternative, non-radiative, mechanisms for returning to the ground state cause many strongly absorbing species to be non-fluorescent and consequently make the prediction of which species will be fluorescent difficult.

Fluorescent labeling can be performed by conjugation of fluorescent organic dyes. However, drawbacks of using fluorescent dyes can include a limited range of light emission and particularly poor photo-stability. Another alternative is semiconducting quantum dots, where inorganic quantum dots can be used for immunofluorescent labeling due to their high quantum yield, high molar extinction coefficients, broad absorption with narrow light emission, and good photo physical and chemical stability. Despite these advantageous properties, cytotoxicity can be a problem using quantum dots in live-cell and animal experiments. Alternative choices include dye-loaded latex particles and dye-doped silica colloids having improved photostability compared to conventional dye molecules. However, dye-loaded beads can have a critical limit of brightness due to self-quenching when a high density of dye is present at a nanoparticle surface, In this context, developing highly emissive and biocompatible luminescent materials that can be readily chemically modified would prove beneficial. Such materials would prove advantageous for labeling and sensor applications.

SUMMARY

The present technology includes systems, methods, articles, and compositions that relate to molecular sensors.

In some embodiments, particular polydiacetylene (PDA) monomers are provided. Sensors, liposomes, and microarrays can be made using the PDA monomers. Particular PDA monomers can be coupled to affinity components to make potassium and mercury sensors. Other PDA monomers can be used to make organophosphate sensors which can detect compounds such as nerve gas. Still other PDA monomers can be used to make melamine sensors. And other PDA monomers provide higher conductivity for sensors, such as wire sensors, compared to polydiacetylene in general.

In some embodiments, a sensor comprises a hydroxyphenyl-benzoxazole (HBO) derivative and a plurality of diacetylene monomer. At least a portion of the diacetylene monomers is coupled to a first affinity component having affinity for a first target. The sensor exhibits a change in fluorescence or conductivity when the affinity component interacts with the first target.

In some embodiments, the present technology provides microarrays having attached thereto, reaction moieties that are capable of binding to a target analyte and cause a change of color and production of fluorescence upon binding between the tethered reaction moiety and the target analyte. The reaction moiety comprises functionalized diacetylene monomers and polydiacetylene polymers having two regions, one for binding to a substrate and one for binding to an accessory molecule.

Further areas of applicability will become apparent from the description provided herein. The description and specific examples in this summary are intended for purposes of illustration only and are not intended to limit the scope of the present disclosure.

DRAWINGS

FIG. 1A depicts a polyfunctional sensor formed of a PDA liposome with affinity components for glucose, DNA, a reversible sensor, antibody-antigen, virus, peptide, CD, and temperature. Upon binding one or more targets, the PDA liposome shifts from a blue color to a fluorescent red color.

FIG. 1B, in the upper panels, depicts a schematic of a microarray sensor of coupled PDA liposomes having affinity components for mercury ions, where the lower panels depict actual fluorescent micrographs of microarray spots following addition of mercury.

Figure 7:
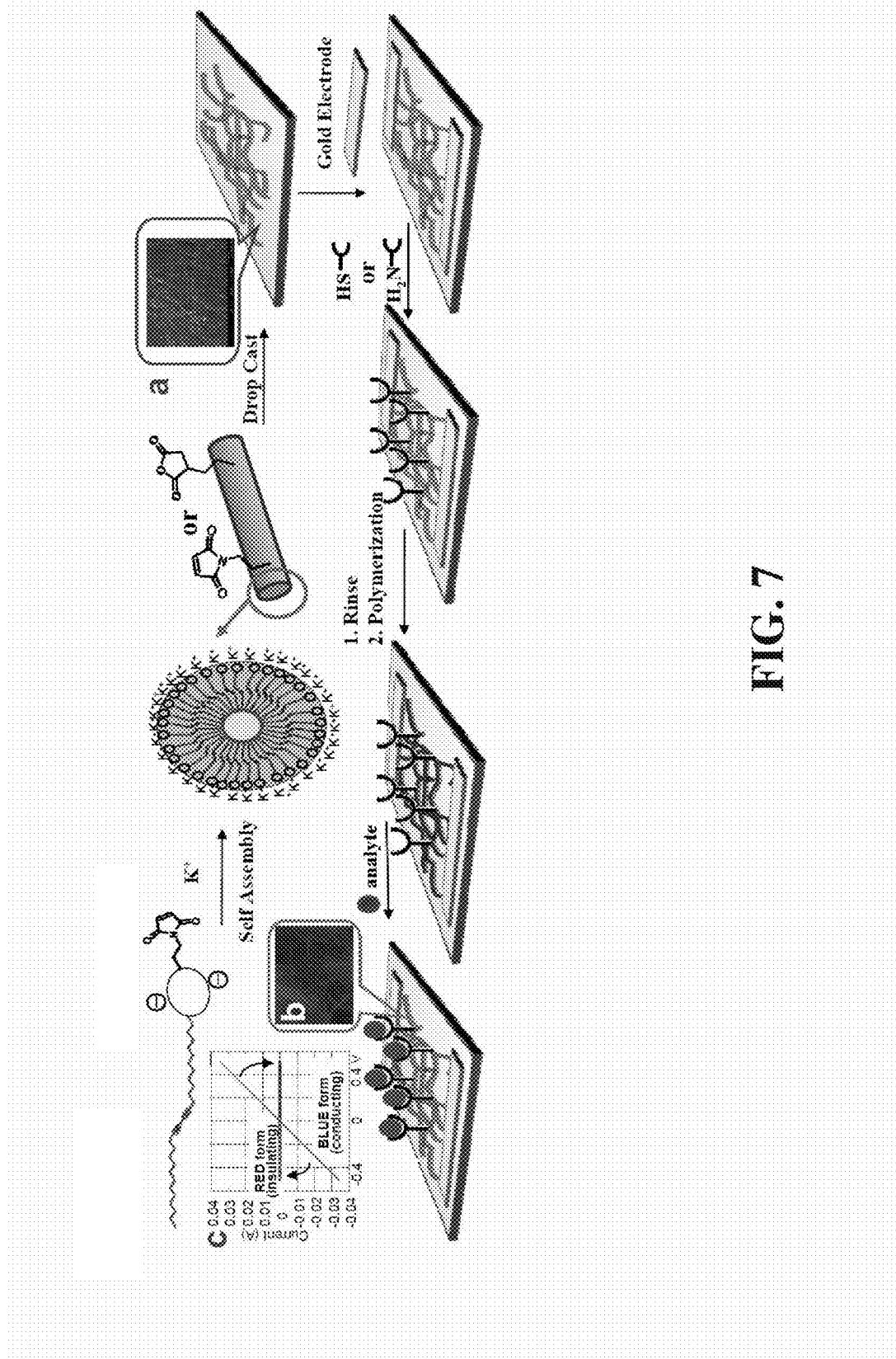

FIG. 7 depicts a schematic illustration of conductivity-based biosensor devices by using diacetylene nanowires. (a) is a scanning electron micrograph (SEM) image of PDA nanowires. (b) is a fluorescent microscope image of the polymerized PDA nanofibers after a heat treatment. (c) shows current (I)-voltage (V) curves of the PDA nanowire device before and after the heat treatment. The blue form (no bound target/analyte) is highly conducting but the red form (bound target/analyte) is not conducting at all.

Figure 8:
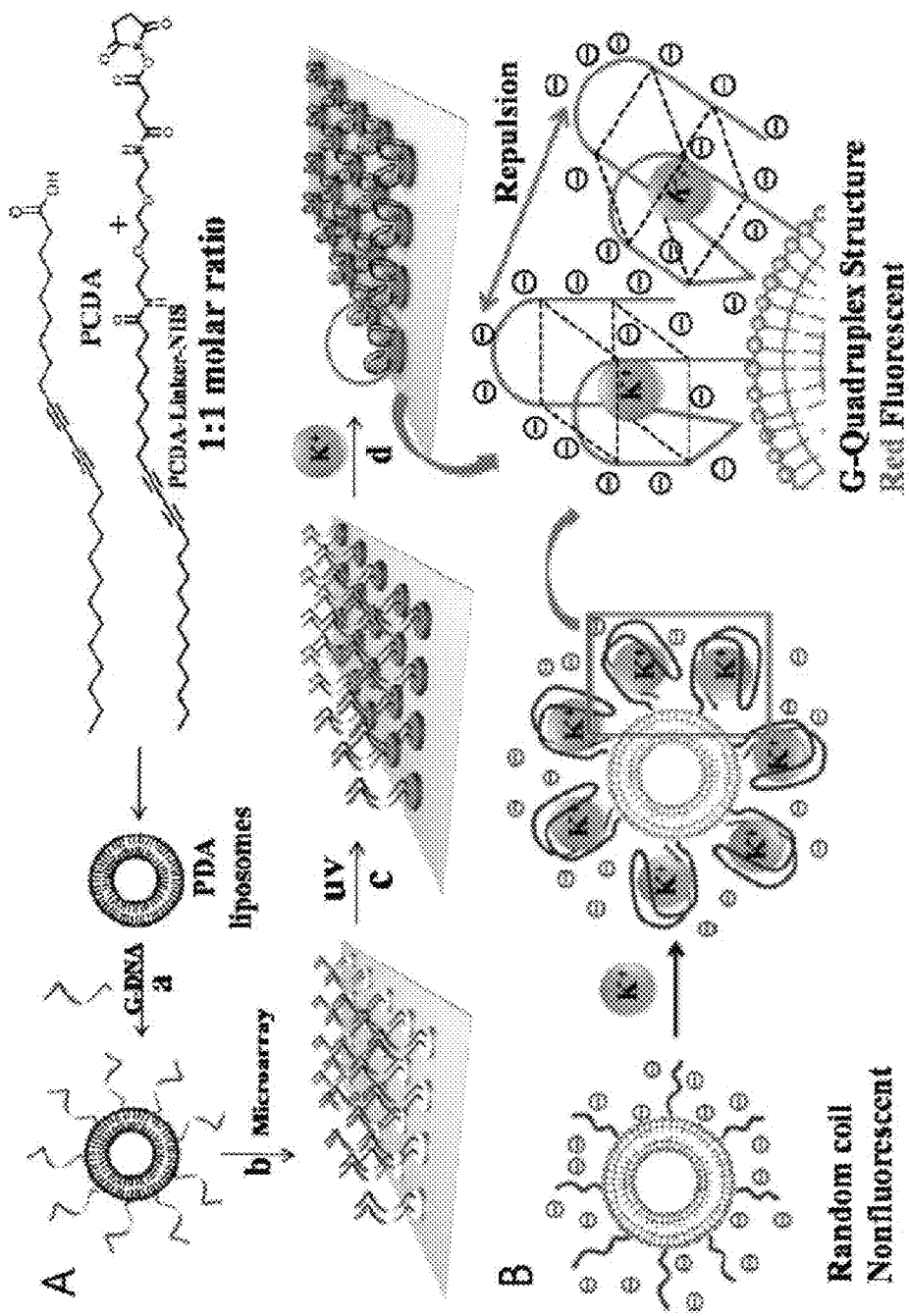

FIG. 8 panel A depicts the chemical structure of an embodiment of diacetylene monomers a schematic representation of the PDA liposome-based microarray for potassium detection. (a) Surface modification of the diacetylene liposome with the amine-functionalized G-rich ssDNA. (b) Microarray of G-rich ssDNA-tethered PDA liposomes onto an amine glass. (c) Photopolymerization of the G-rich ssDNA-tethered PDA liposomes using a 254 nm UV lamp. (d) Recognition of target potassium ions via the quadruplex formation results in red fluorescent emission. FIG. 8 panel B depicts a schematic representation of the G-quadruplex formation and the resulting steric repulsion.

Figure 9:
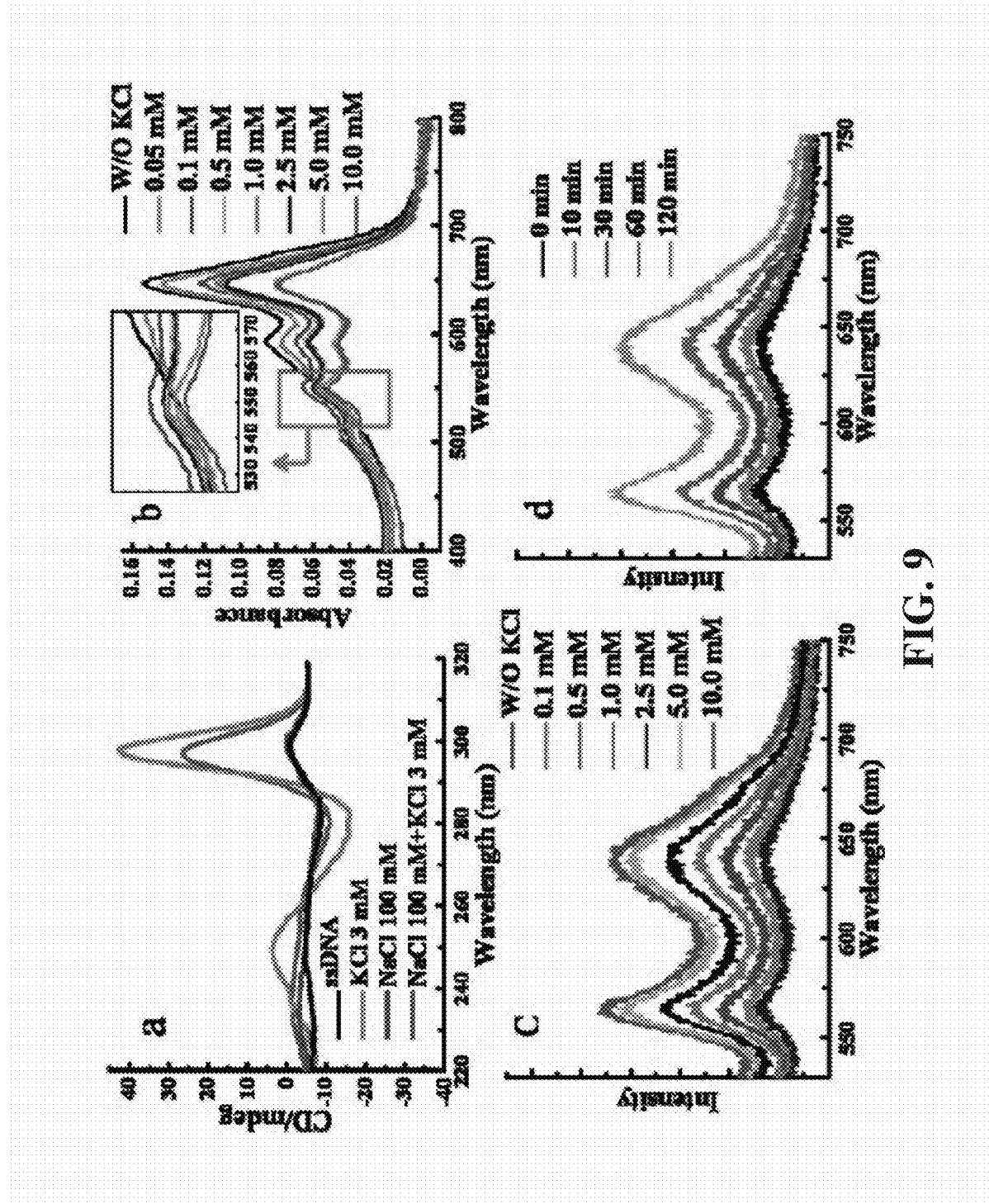

FIG. 9 depicts: (a) CD spectra of the G-quadruplex at 6° C. before and after adding K+ and Na+; (b) UV-vis spectrum; (c) PL spectrum change of G-rich ssDNA-tethered PDA liposome solution (1 mM) upon addition of KCl, where the concentration of KCl ranges from 0 to 10.0 mM; and (d) PL spectrum change of the G-rich ssDNA-modified PDA liposome solution (1 mM) upon addition of 1 mM KCl (excitation at 503 nm).

Figure 10:
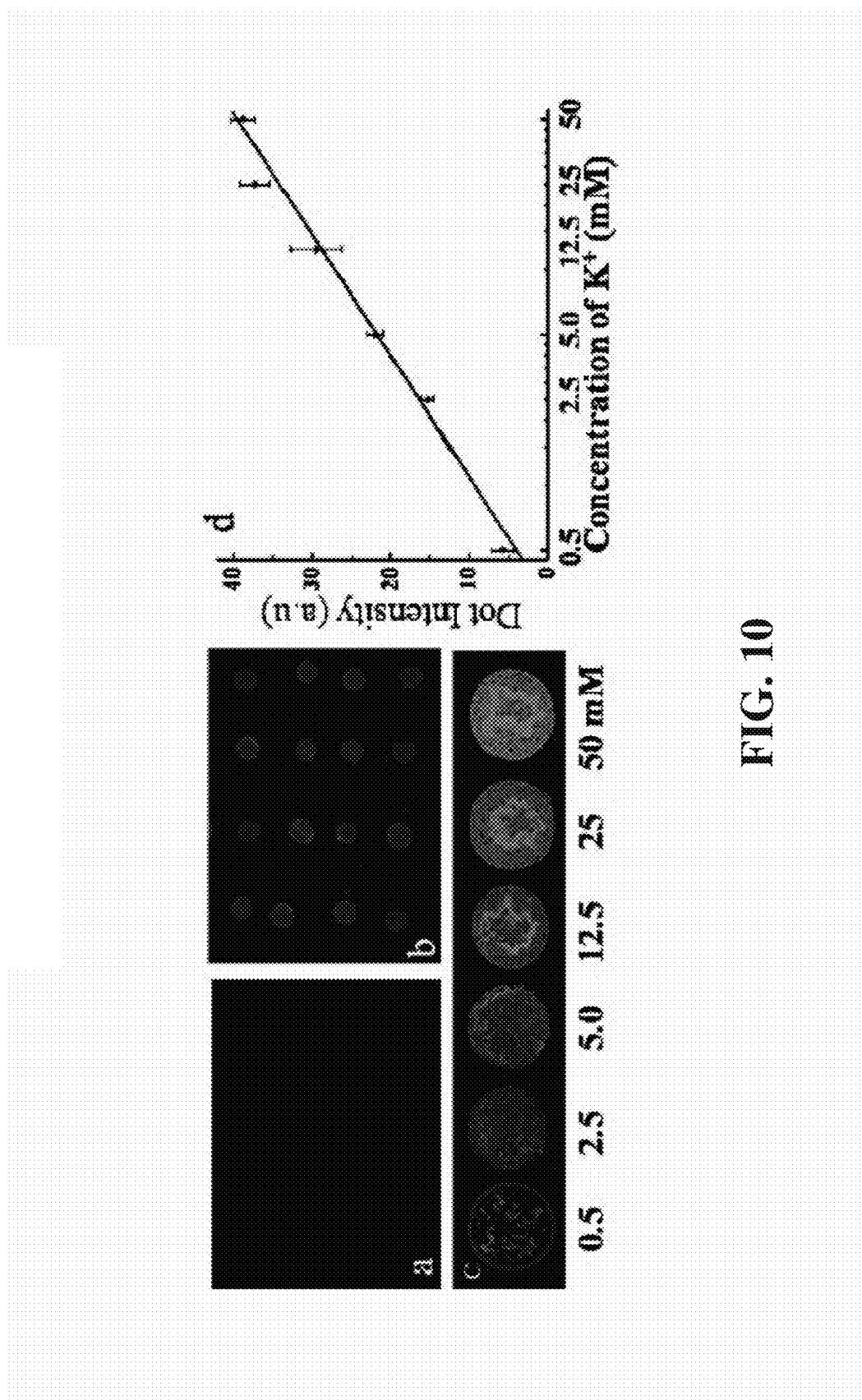

FIG. 10 depicts fluorescent microscope images of the microarrayed PDA liposomes (excitation at 600 nm and a long-pass emission filter with 550 nm cutoff): (a) after adding NaCl (5 mM) and before KCl (5 mM) addition; (b) after adding the KCl solution and 30 min of incubation at room temperature; and (c) fluorescent images of the PDA liposome arrays with KCl solutions at various concentrations (20 mL each). (d) Graphically depicts the correlation curve between the fluorescence intensity and the amount of K+.

Figure 11:
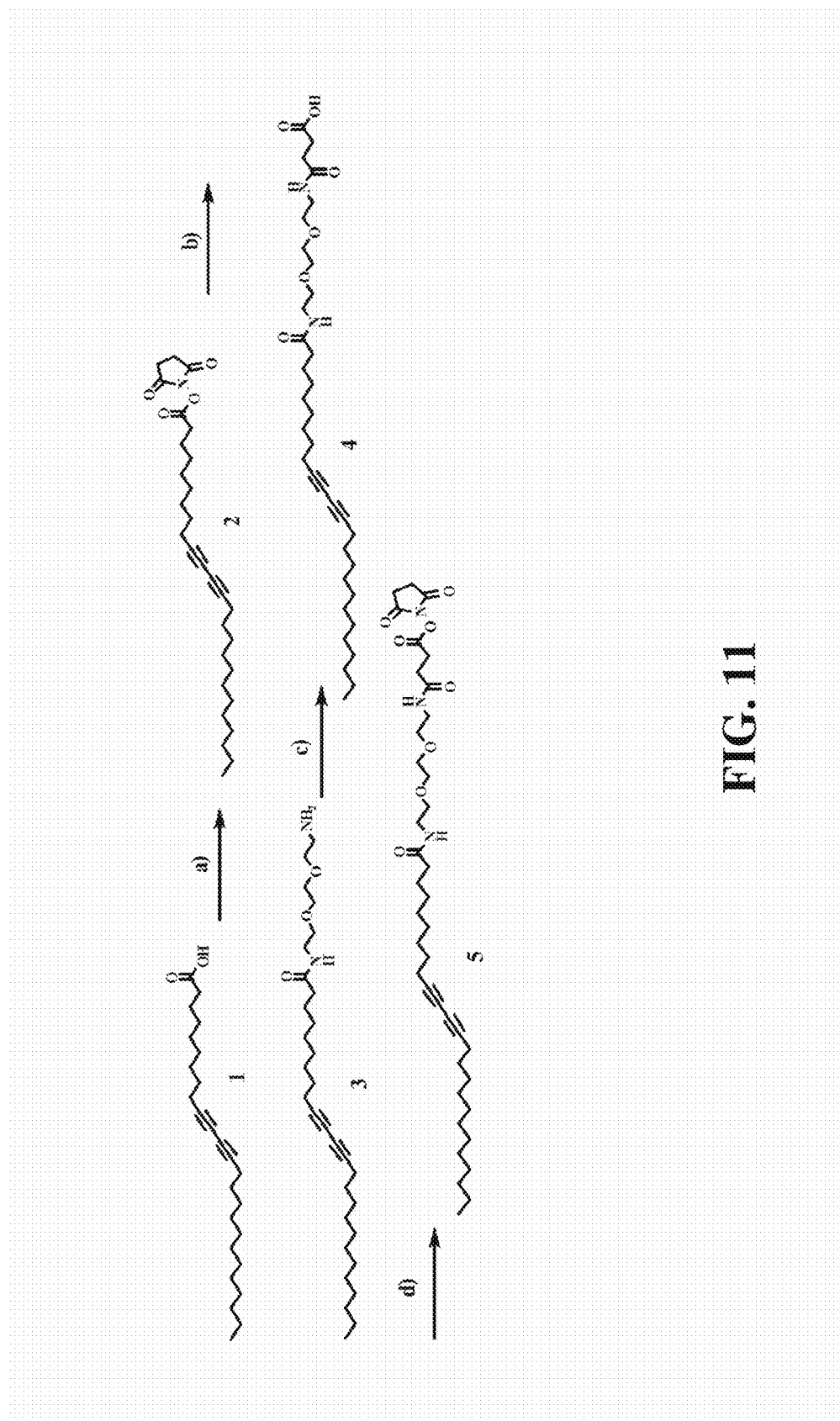

FIG. 11 depicts a reaction scheme for the preparation of PCDA-Linker-NHS. Monomer synthesis: (a) N-hydroxysuccinimide, N-(3-Dimethylaminopropyl)-N6-ethylcarbodiimide hydrochloride, methylene chloride, 25° C., 2 hr. (b) 2,26-(Ethylenedioxy)bis(ethylamine), methylene chloride, 25° C., 2 hr. (c) succinic anhydride, N,Ndimethylformamide, 25° C., 2 h. (d) N-hydroxysuccinimide, N-(3-Dimethylaminopropyl)-N6-ethylcarbodiimide hydrochloride, methylene chloride, 25° C., 2 hr.

Figure 12:
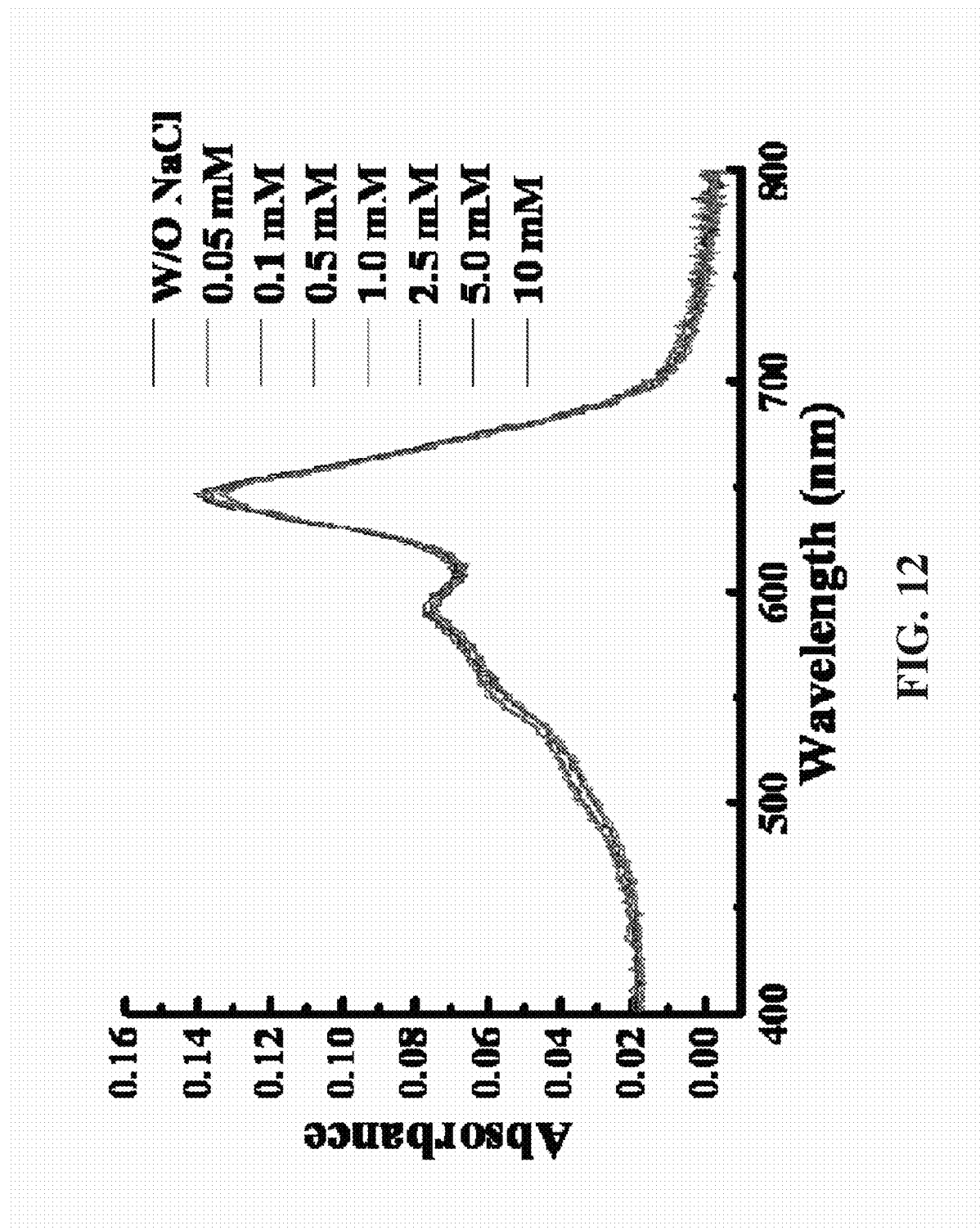

FIG. 12 shows the UV spectrum change of G-rich ssDNA tethered liposome solution upon adding NaCl.

Figure 13:
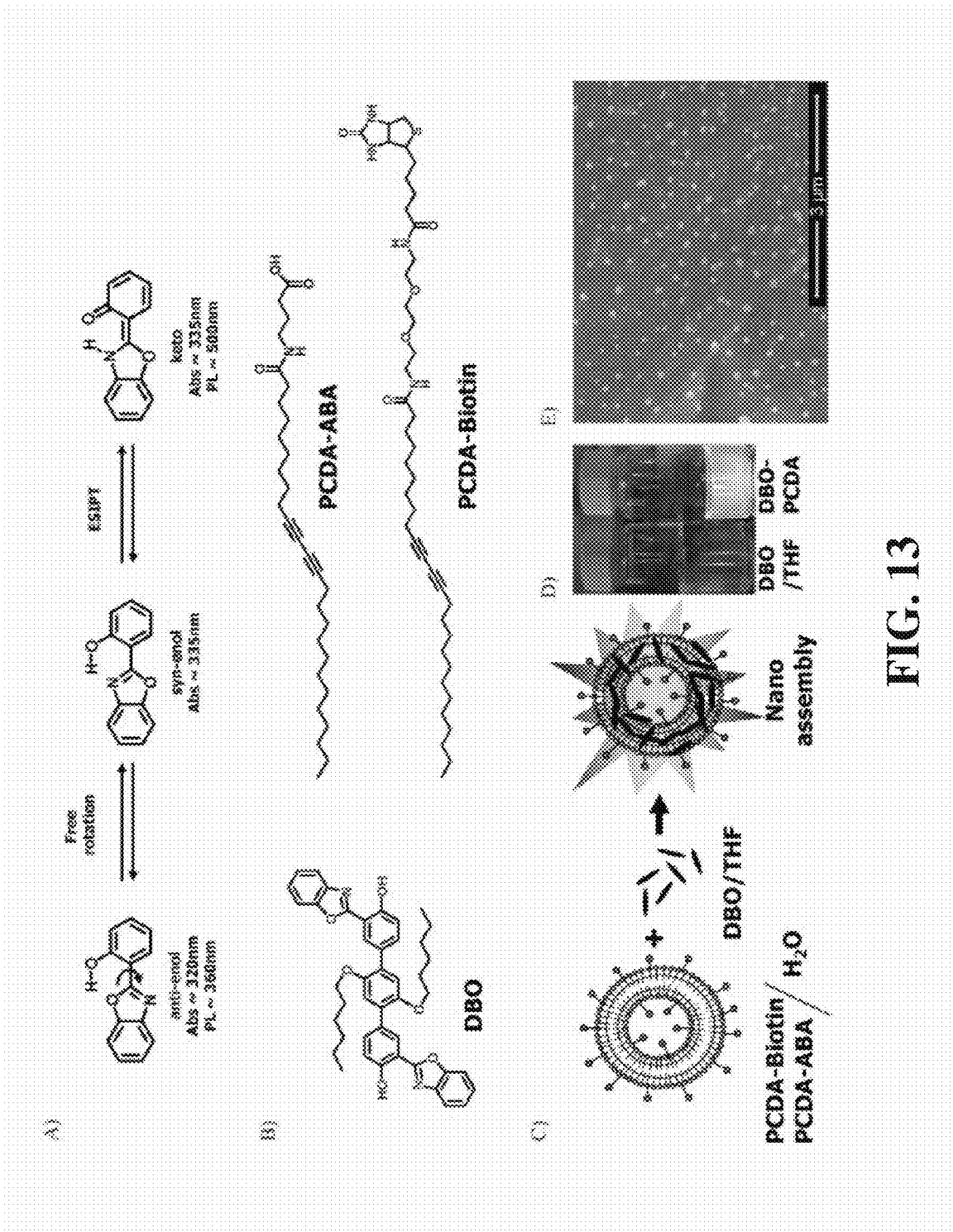

FIG. 13 panel (A) shows rotamer structures (anti-enol and syn-enol) of HBO and its excited state keto formation. The given wavelengths are their absorption and emission λmax. Panel (B) shows molecular structures of DBO, PCDA-ABA, and PCDA-Biotin. Panel (C) is a schematic representation of nanoparticle assembly of DBO in a PCDA vesicle. Panel (D) is a photograph of DBO in THF solution and DBO-PCDA nanoparticles under 365 nmUV light. And panel (E) is a scanning electron microscopy image of the DBO-PCDA nanoparticle.

Figure 14:
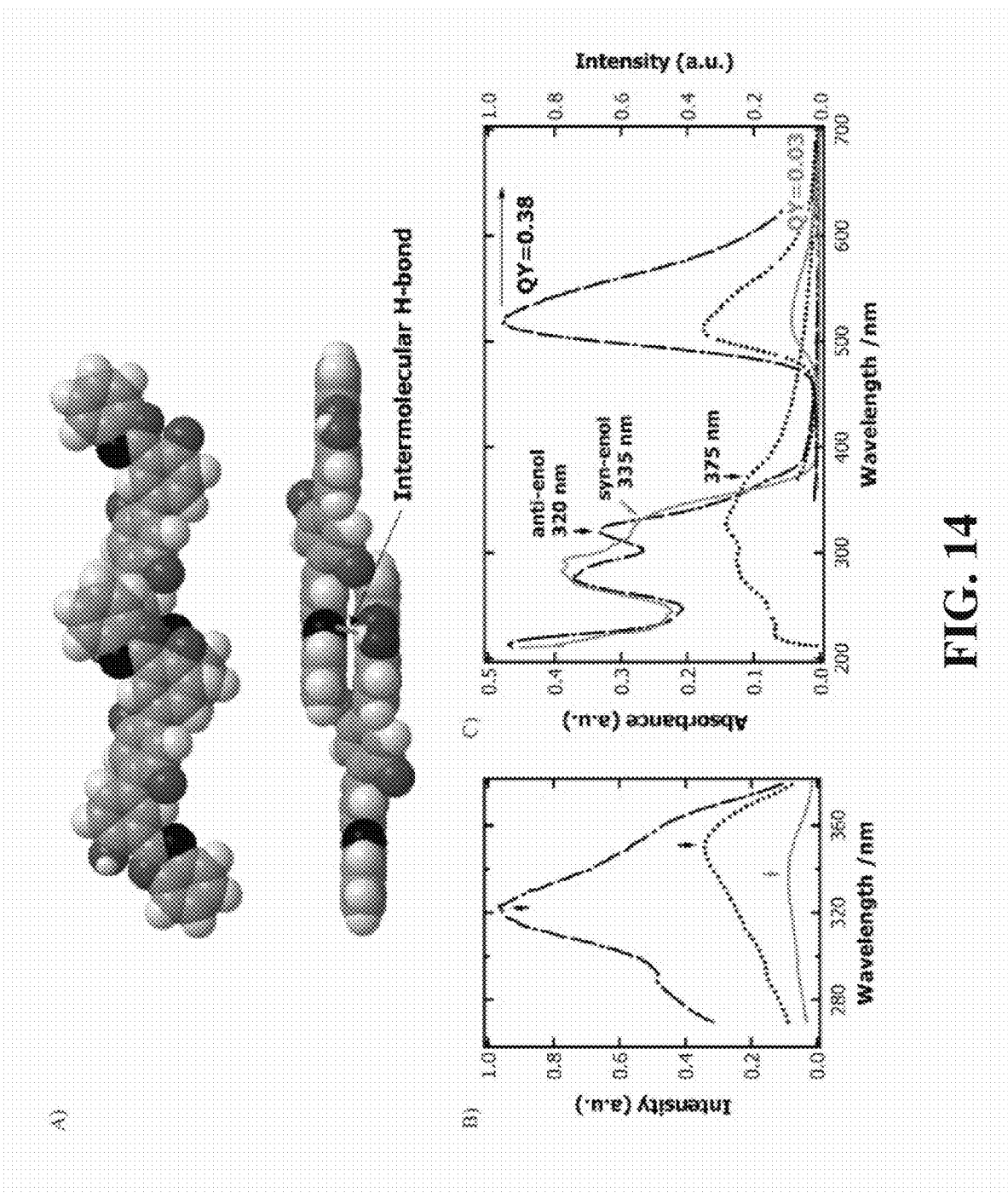

FIG. 14 panel (A) is a geometry-optimized molecular structure of DBO produced by using Materials Studio 4.1 with DFT (density functional theory) with MAP parameter. Two DBOs are organized to show intermolecular hydrogen bonding between benzoxazole units. Panel (B) graphically depicts excitation spectra of DBO in THF solution (solid line), dispersion in deionized water (dotted line), and dispersion in diacetylene vesicle (broken line) for the 520 nm emission of FIG. 14C. Panel (C) graphically depicts UV/V is absorption and photoluminescence spectra of DBO in THF solution (solid lines), in THF:H$_2$O (1:9 v/v) (dotted lines), and in the diacetylene vesicle solution (broken lines). The concentration of the DBO solution and dispersions was 10 mM.

Figure 15:
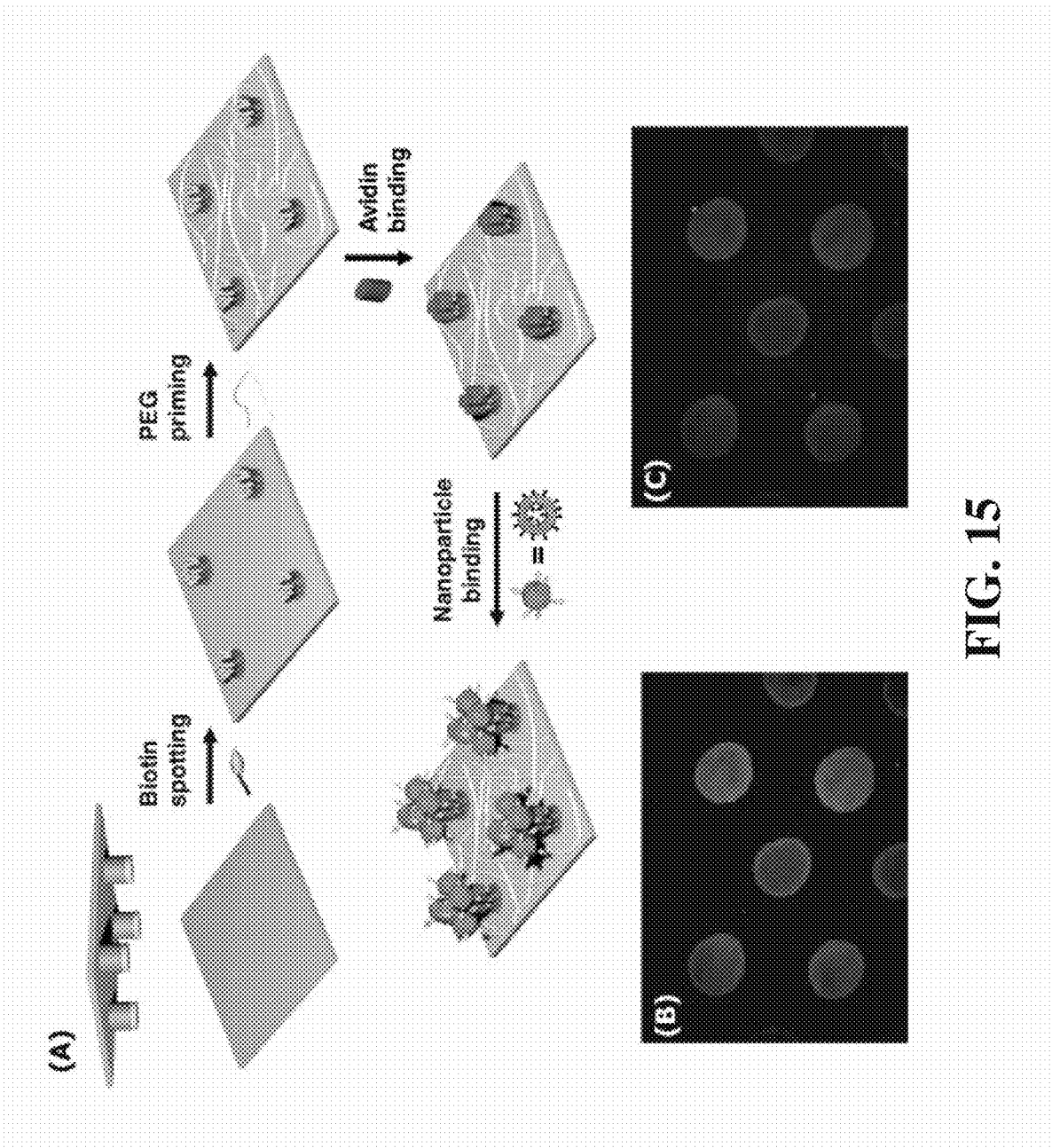

FIG. 15 panel (A) is a schematic illustration of selective fluorescence labeling by means of functionalized DBO-PCDA organic nanoparticles. Panel (B) shows a fluorescence microscopy image obtained by using a 400 nm long-pass emission filter after selective binding of biotinylated DBO-PCDA nanoparticles on the patterned avidin surface. And panel (C) is a fluorescence microscopy image from a 600 nm long-pass emission filter showing the red fluorescence emission from the red phase of polydiacetylene passivation layer induced by biotin-avidin interaction. The diameter of the dots of the fluorescence microscopy images is 500 mm.

Figure 16:
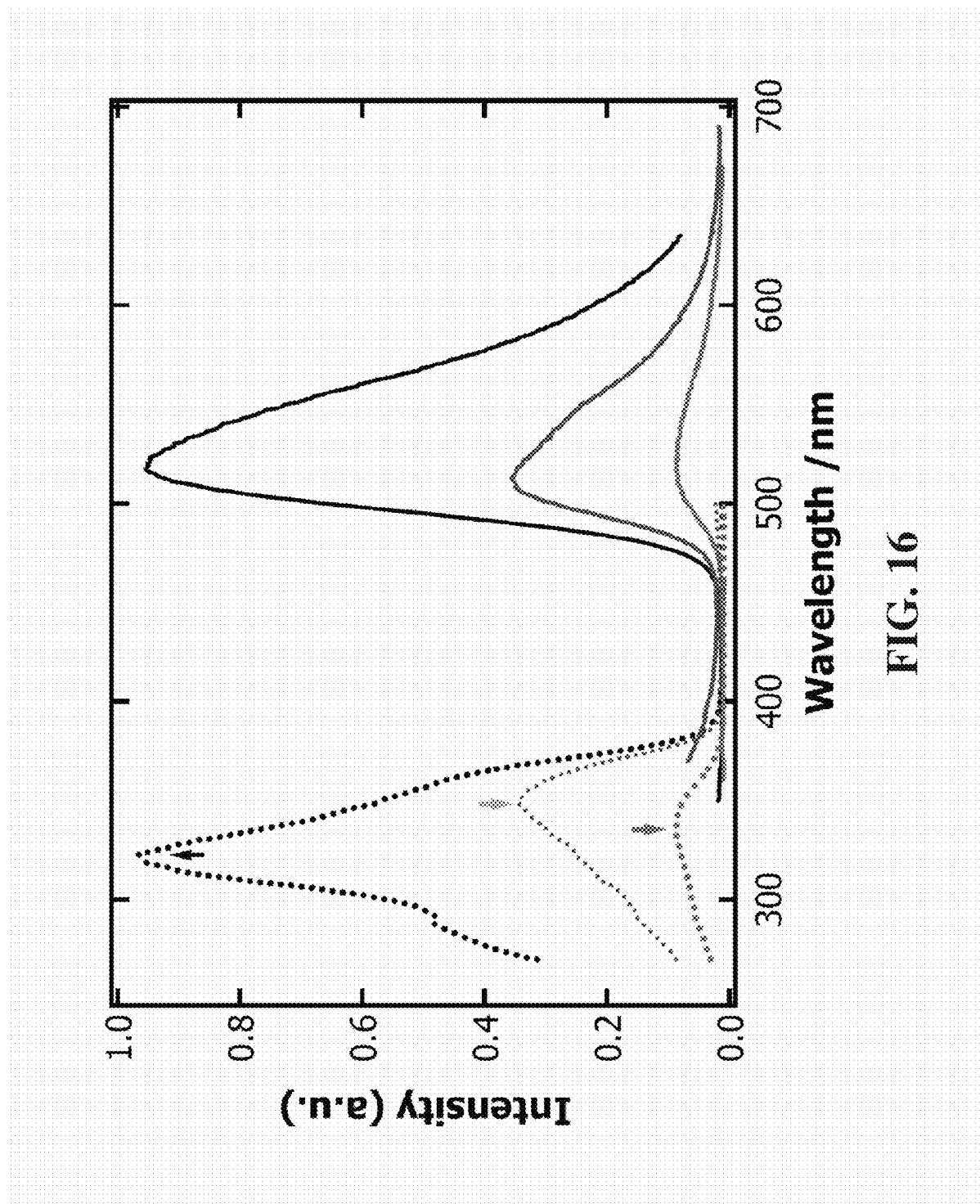

FIG. 16 graphically depicts the excitation (dotted lines) and emission (solid lines) spectra of DBO in THF solution (bottom set of red lines), dispersion in deionized water (middle set of blue lines), and dispersion in diacetylene liposome (top set of black lines). The concentrations of DBO were 10 μM. There is red shift for the nanoparticles in THF/H$_2$O mixture. The anti-enol species (320 nm) formation is seen for the DBO-PCDA vesicle.

Figure 17:
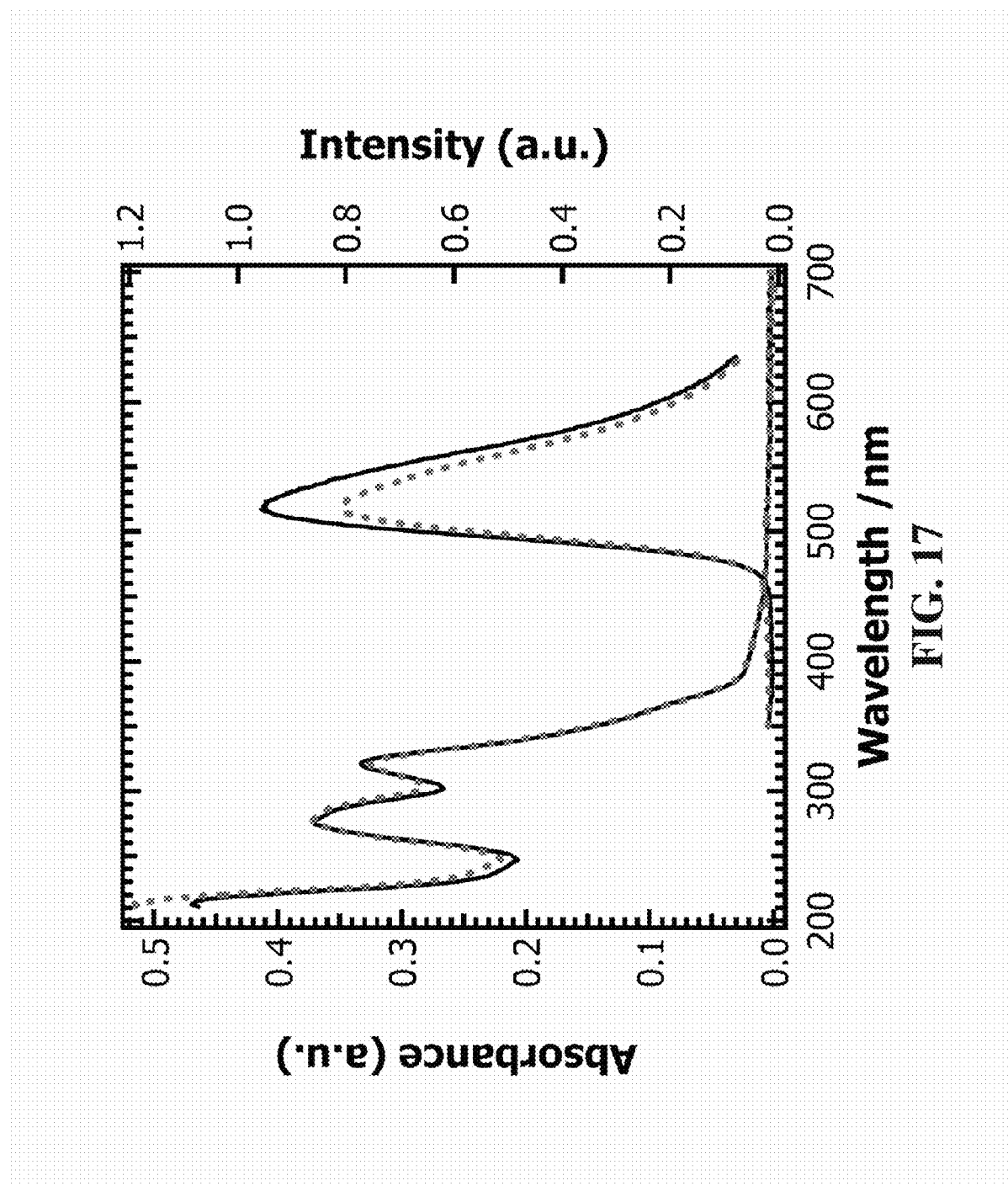

FIG. 17 graphically depicts UV irradiation of DBO nanoparticles in THF/H$_2$O mixture. 6 W 254 nm UV was illuminated 1 cm above the suspension. The black solid lines are before UV irradiation and the red dotted lines were obtained after 30 min. of exposure.

Figure 18:
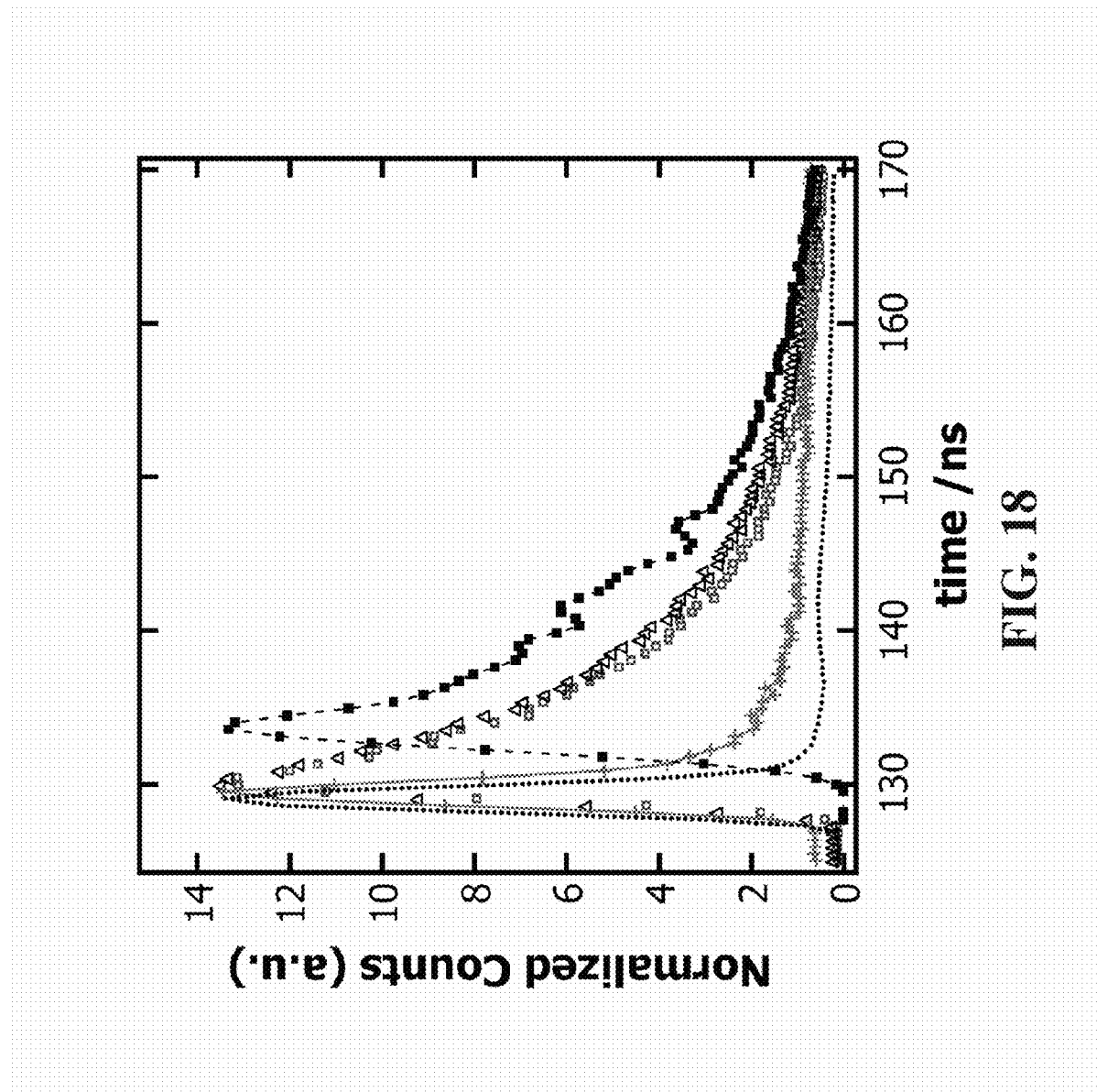

FIG. 18 graphically depicts the fluorescence lifetime of DBO in THF solution (red+), dispersion in THF:H$_2$O 1:9 v/v mixture (blue open squares), and dispersion in diacetylene liposome (black open triangles) observed at 380 nm excitation wavelength. Lifetime measurement was also done at 310 nm excitation for the DBO-PCDA nanoparticles (solid black squares). Instrument response function is plotted in the dotted line.

Figure 19:
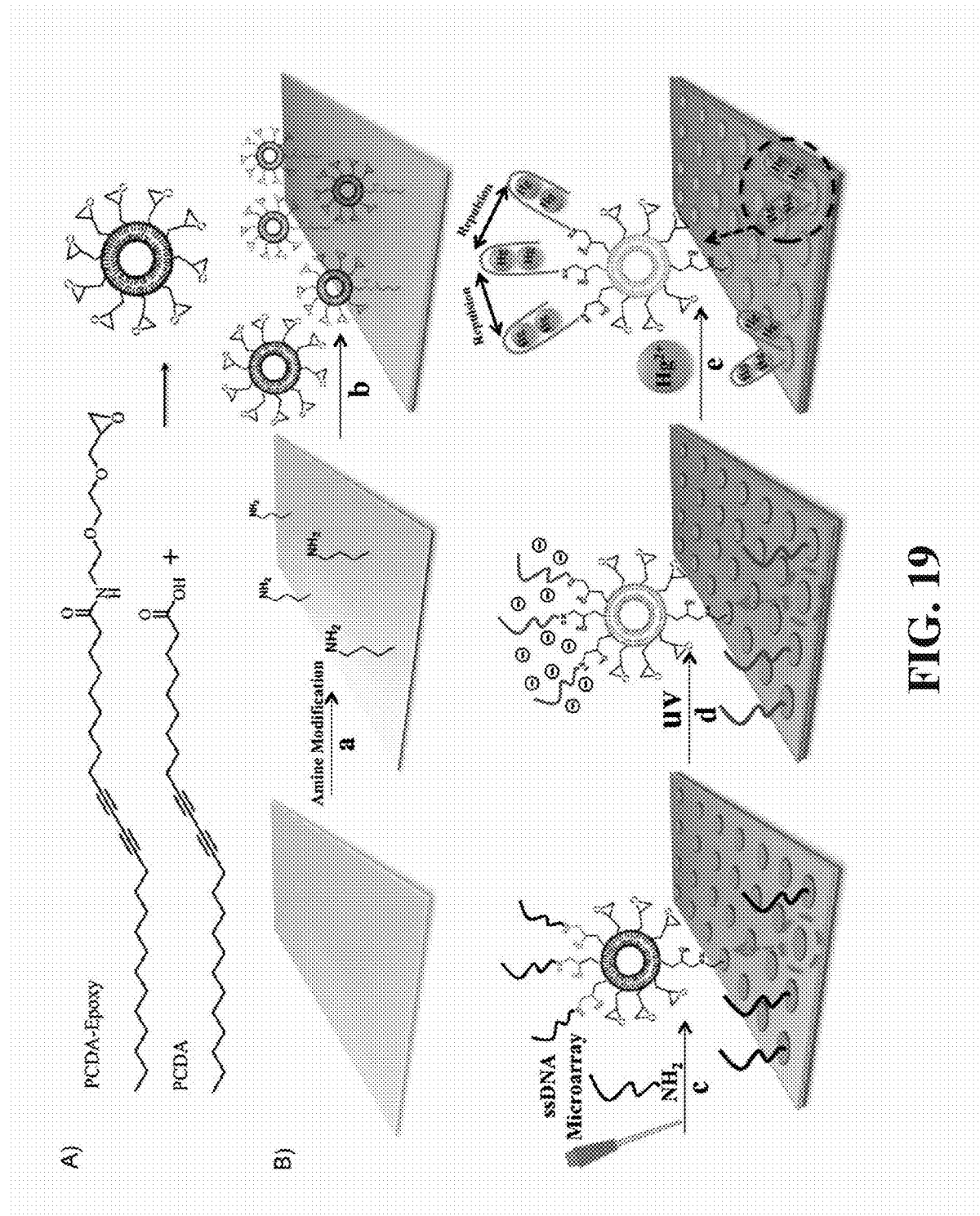

FIG. 19 panel (A) shows the chemical structure of the diacetylene monomers, PCDA and PCDA-Epoxy. Panel (B) is a schematic illustration of the PDA liposome-based microarray for mercury detection, with: a) surface modification of the glass substrate with amine functionality, b)

immobilization of the Epoxy liposomes onto the amine glass slide through epoxy-amine coupling, c) post tethering of the ssDNA aptamer by means of a microarrayer, d) photopolymerization of the PDA liposomes by using a 254 nm UV lamp, and e) recognition of the target mercury ions results in red fluorescent emission.

Figure 20:
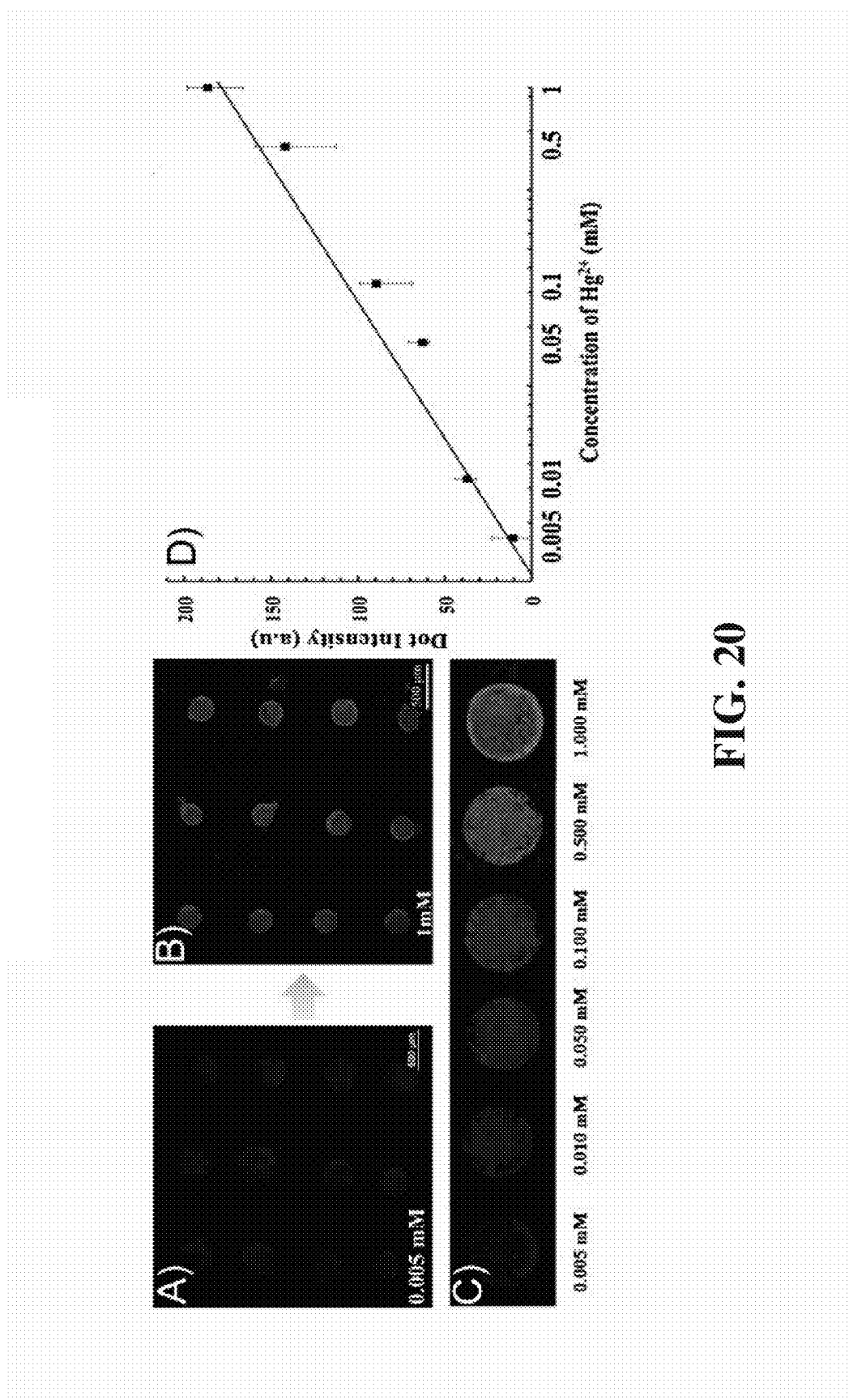

FIG. 20 depicts fluorescence microscope images of the PDA microarray (excitation at 600 nm and a long-pass emission filter with 550 nm cutoff were used) after 1 hour of incubation at room temperature with (A) 0.005 mM of $Hg^{2+}$ and (B) 1 mM of $Hg^{2+}$ solution. Panel (C) shows fluorescence microscope images of the PDA liposome arrays after 1 hour of incubation at room temperature with $Hg^{2+}$ solutions in various concentrations. Scale bar is 500 µm. Panel (D) is a correlation curve between the fluorescence intensity and the amount of $Hg^{2+}$.

Figure 21:
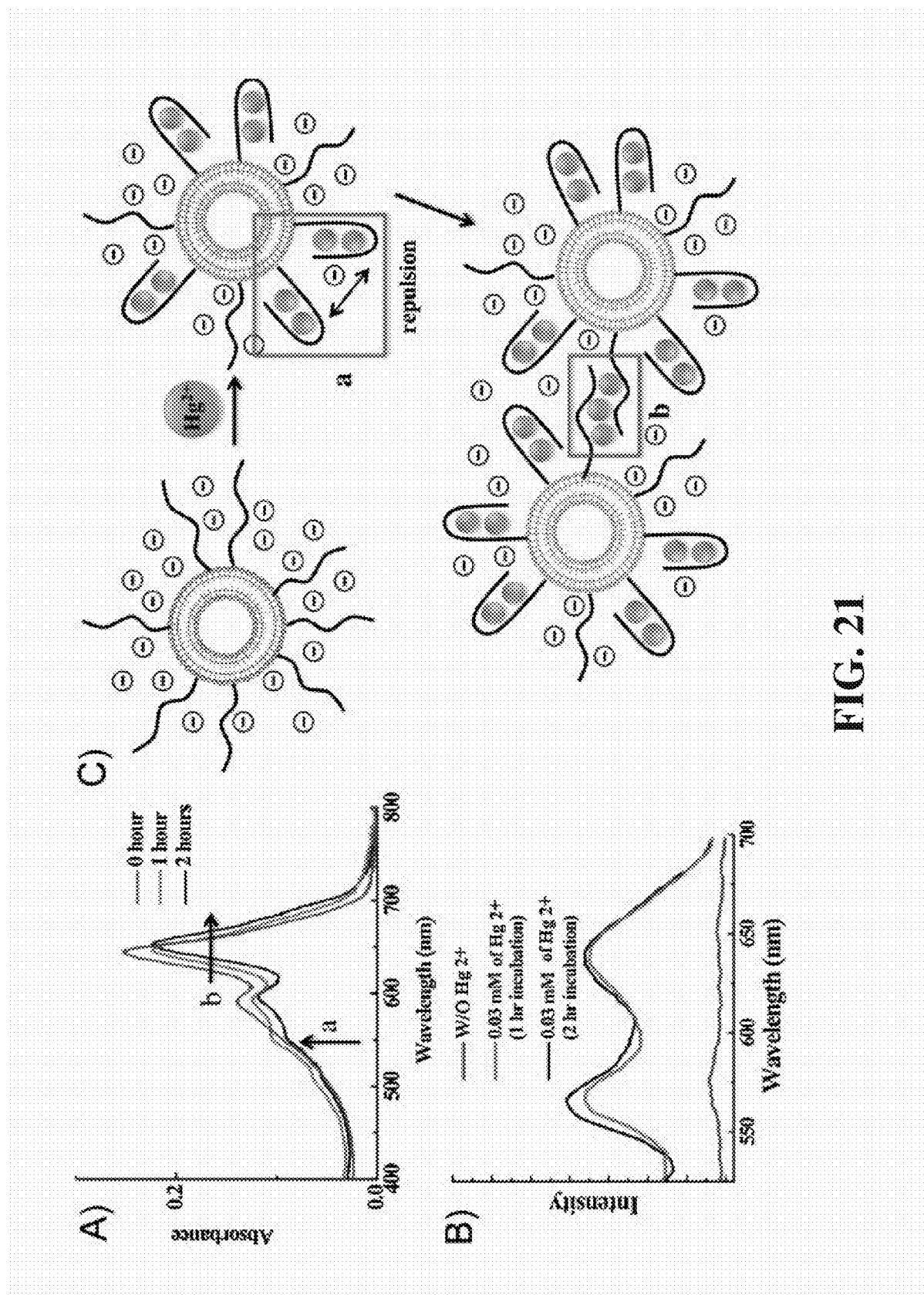

FIG. 21 panel (A) graphically depicts UV-vis spectra and (B) graphically depicts PL spectra of the PDA liposome solution (0.05 mM) upon addition of $Hg^{2+}$ (0.03 mM/0.027 mg) for 1 hour (red line) and 2 hours (black line) of incubation. Panel (C) is a schematic illustration of the T-Hg-T conformation in the PDA liposome solution, where (a) shows the resulting steric repulsion between the intermolecular T-Hg-T complexes after 1 hour incubation at room temp and (b) shows the formation of the intermolecular T-Hg-T aggregation after 2 hours incubation at room temp.

Figure 22:
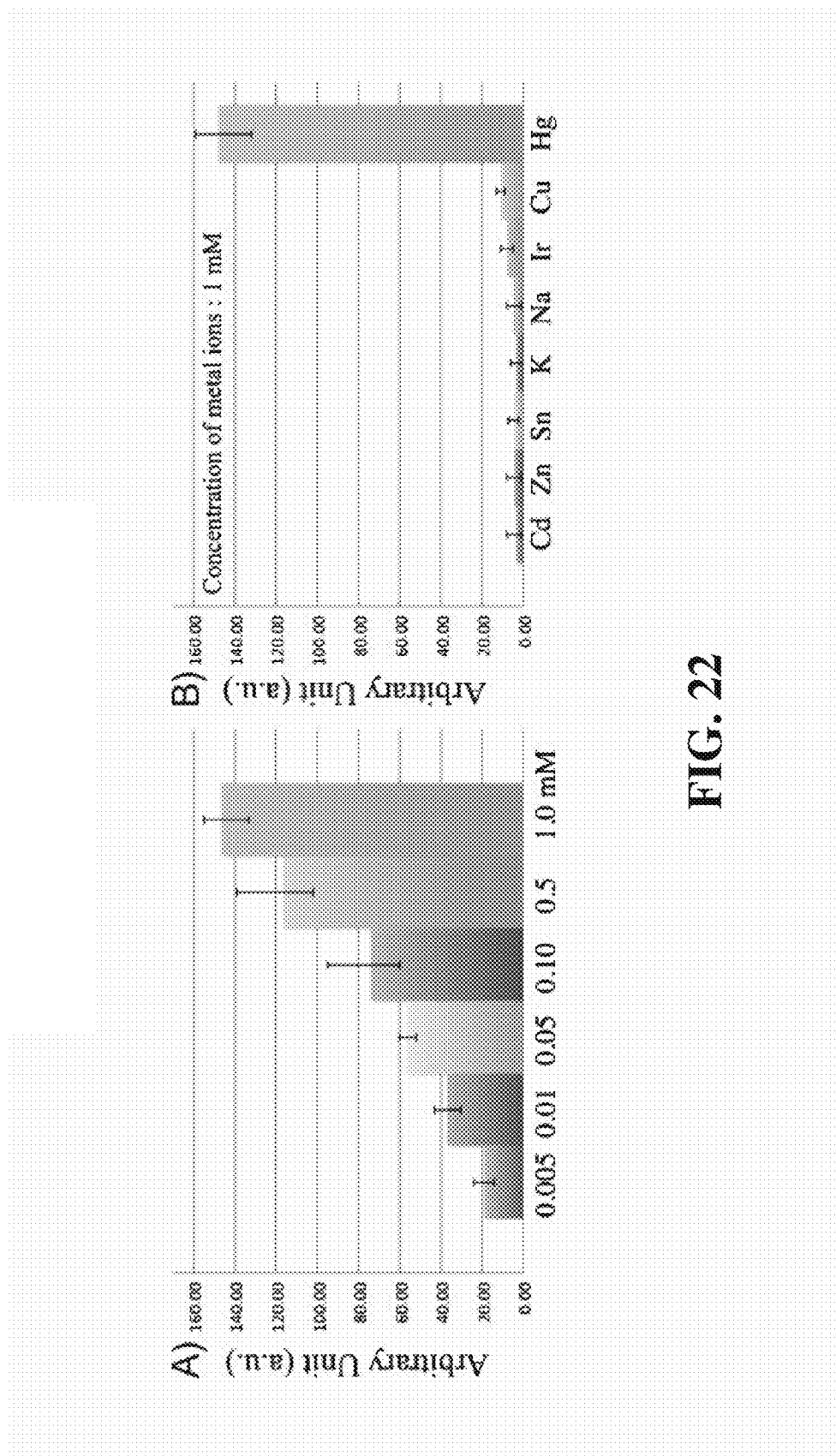

FIG. 22 panel (A) graphically depicts the fluorescence intensity of the PDA microarray after 1 hour incubation with $Hg^{2+}$ (0.005, 0.01, 0.05, 0.10, 0.50, 1.00 mM). And panel (B) graphically depicts the fluorescence intensity of the PDA microarray after 1 hour of incubation with 1.0 mM of each respective metal ion.

Figure 23:
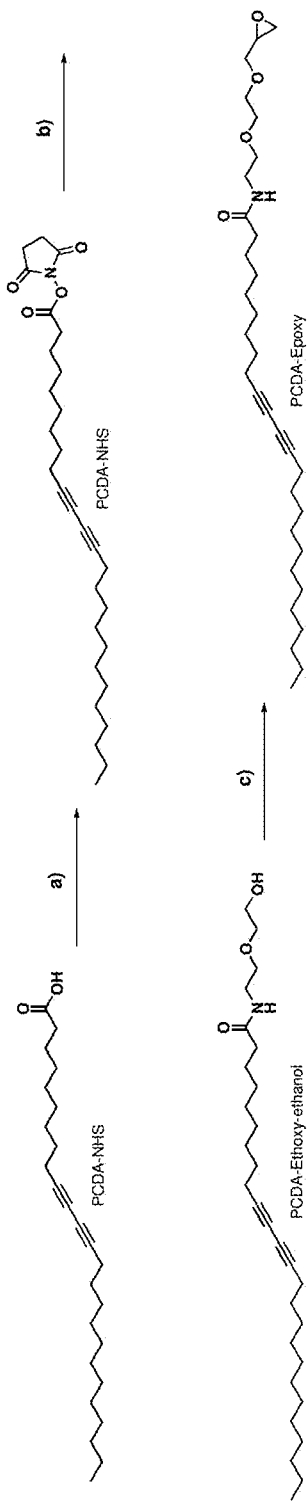

FIG. 23 depicts synthesis of (10,12-pentacosadiynoic acid)-epoxy (PCDA) derivatives.

Figure 24:
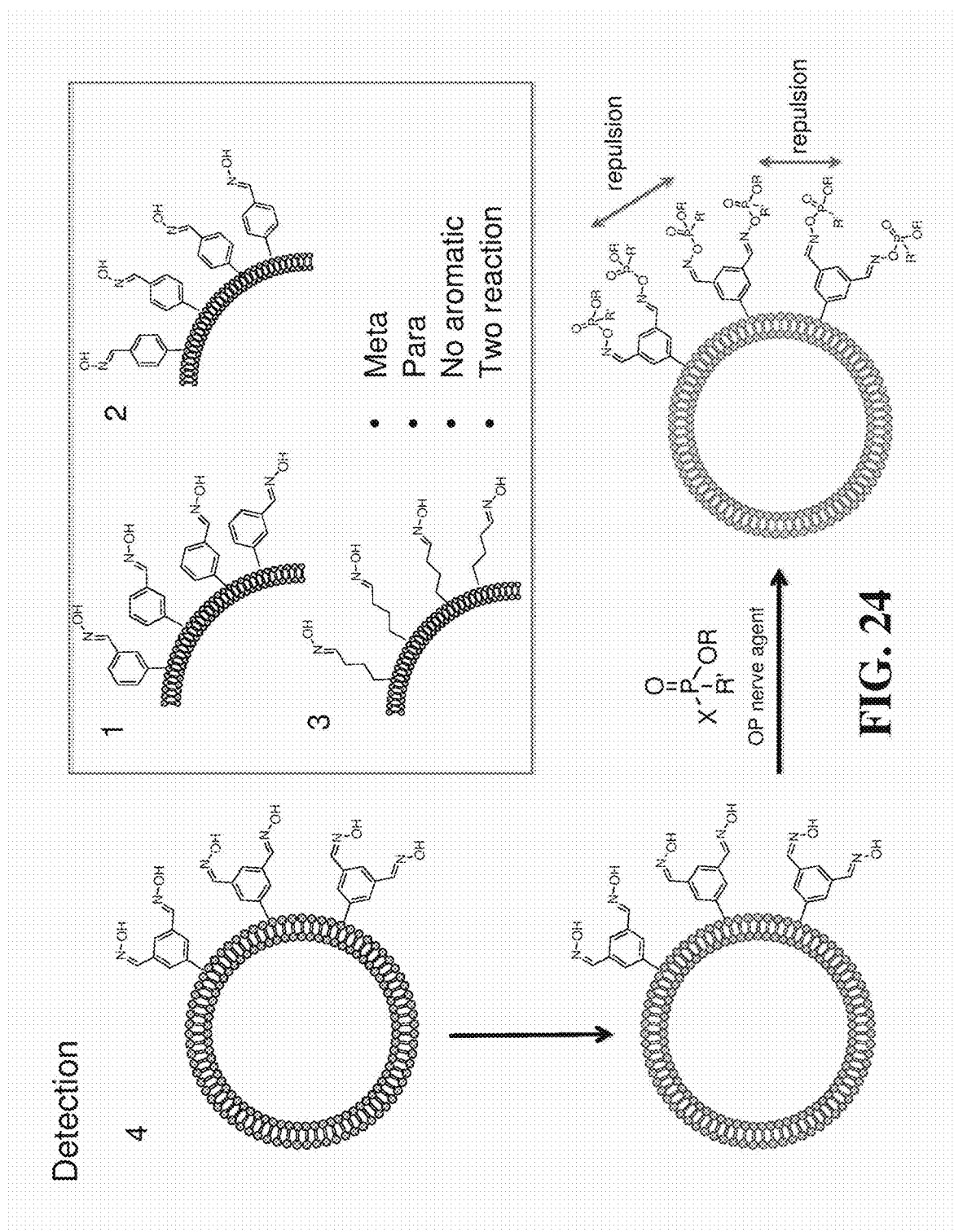

FIG. 24 shows a detection mechanism for organophosphate nerve gas agent.

Figure 25:
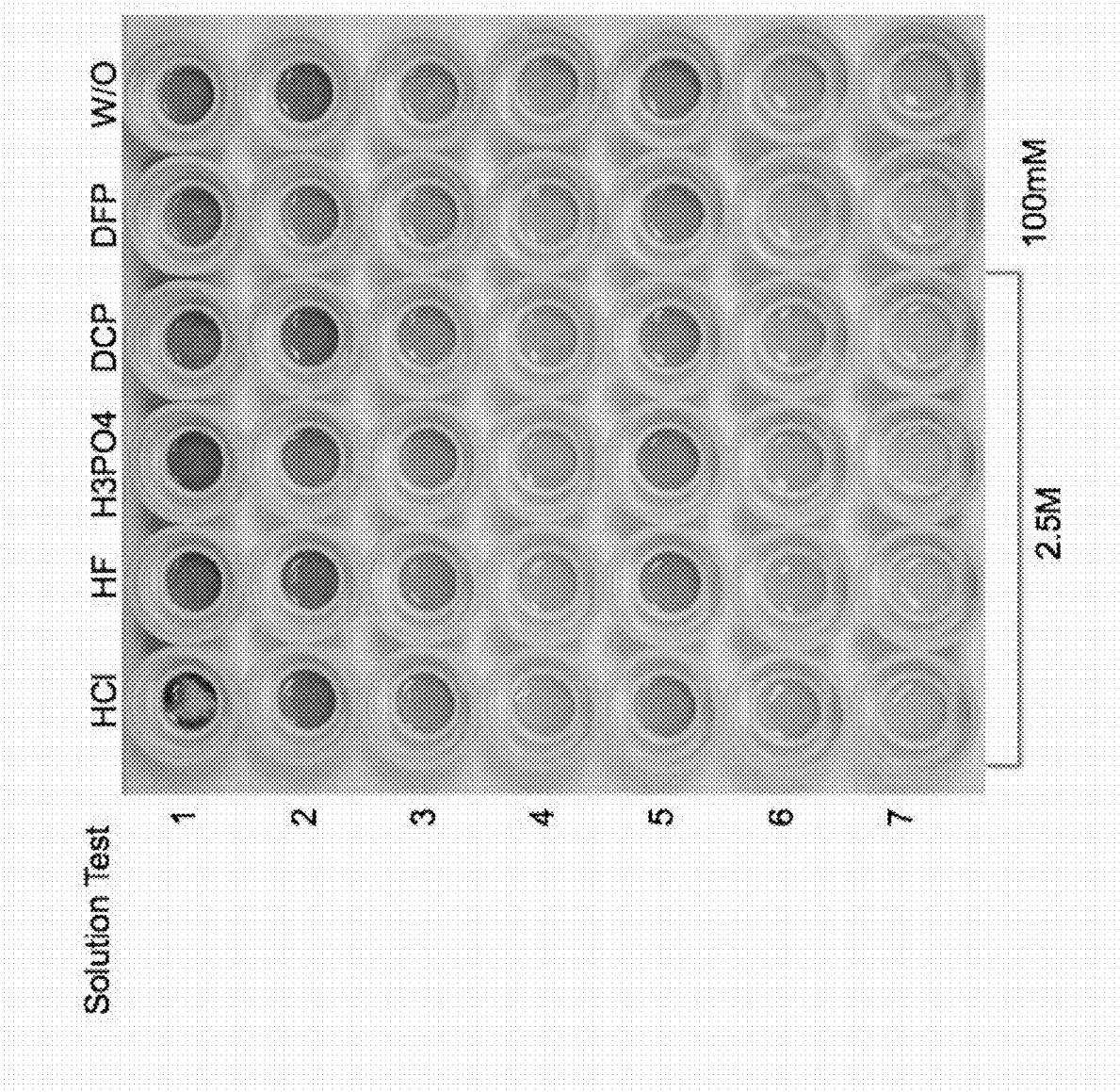

FIG. 25 shows the results of liposome gel testing for the OP nerve gas precursors DCP and DFP and for other acids to demonstrate the selectivity and sensitivity.

Figure 26:
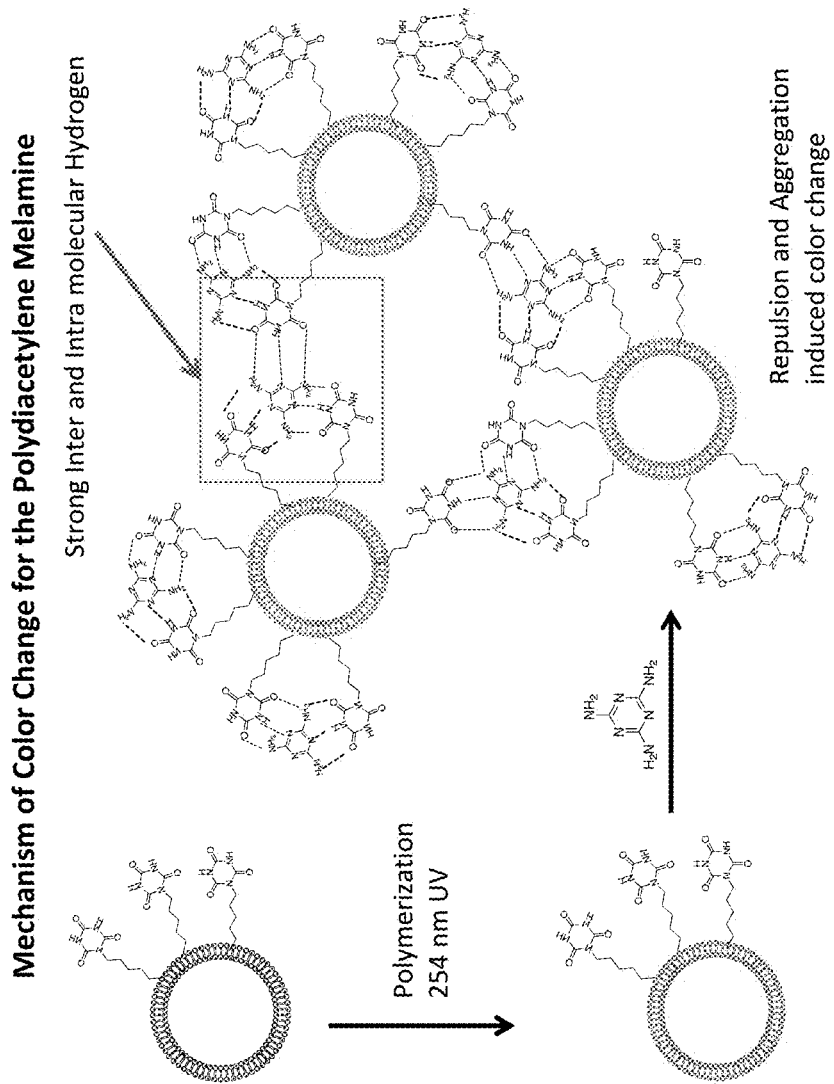

FIG. 26 shows a mechanism of color change for the polydiacetylene melamine sensor.

Figure 27:
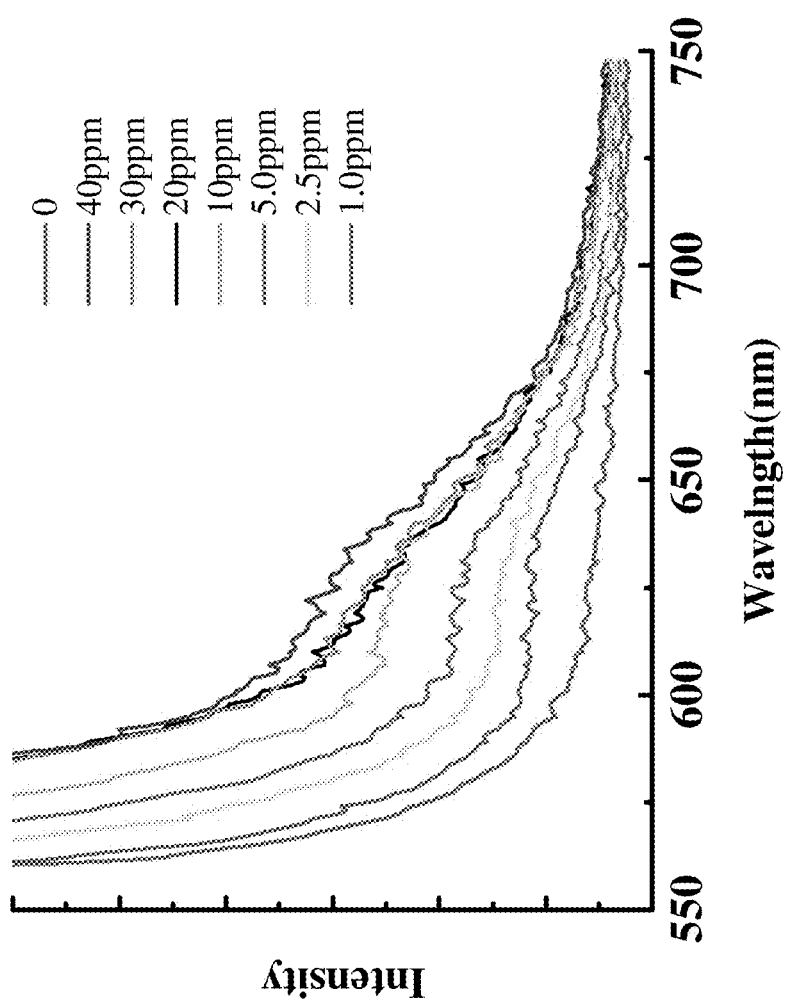

FIG. 27 shows the UV spectrum change of PCDA liposomes following addition of increasing amounts of melamine.

Figure 28:
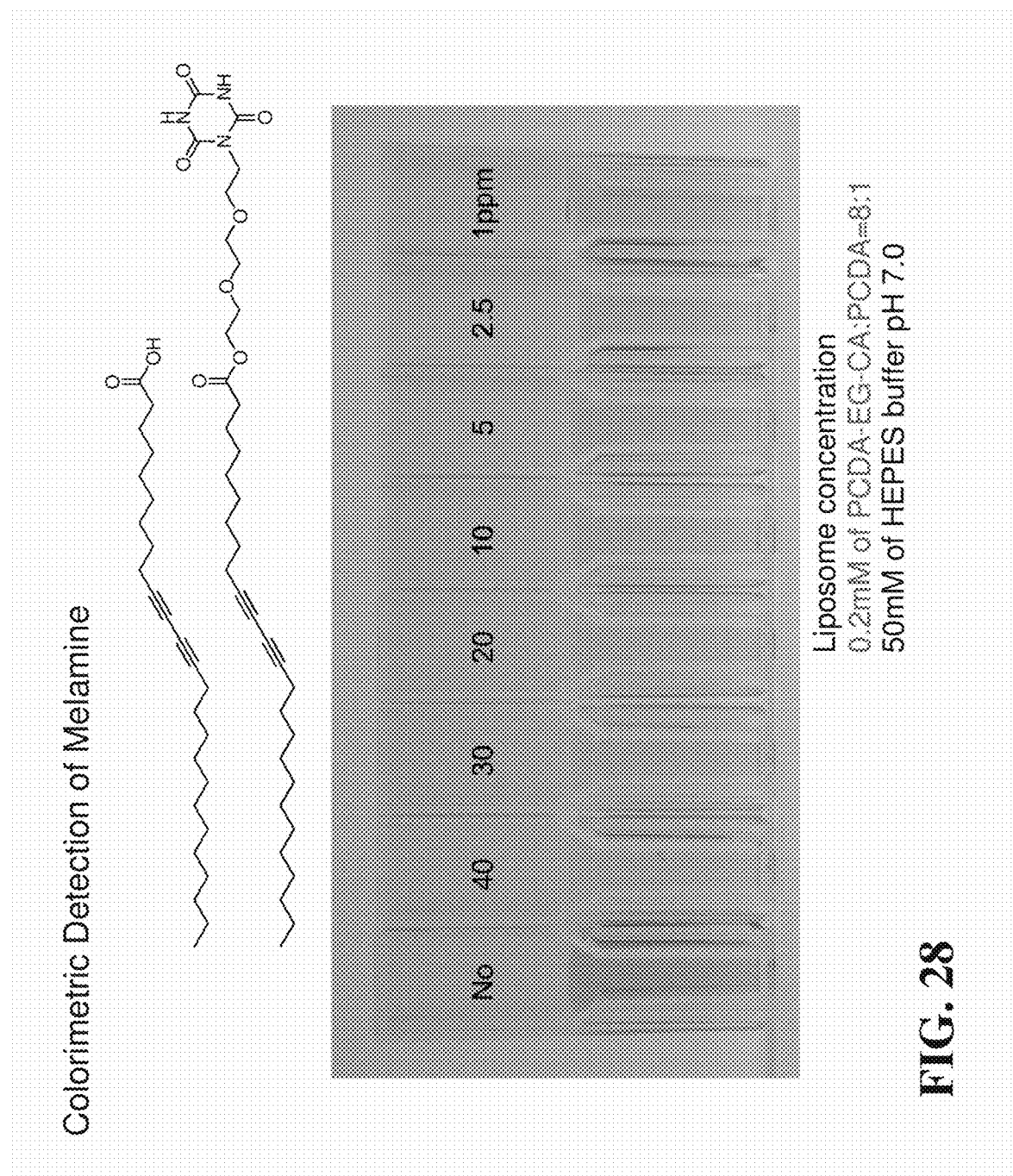

FIG. 28 shows the visible color change observed for detecting various concentrations of melamine in ppm.

Figure 29:
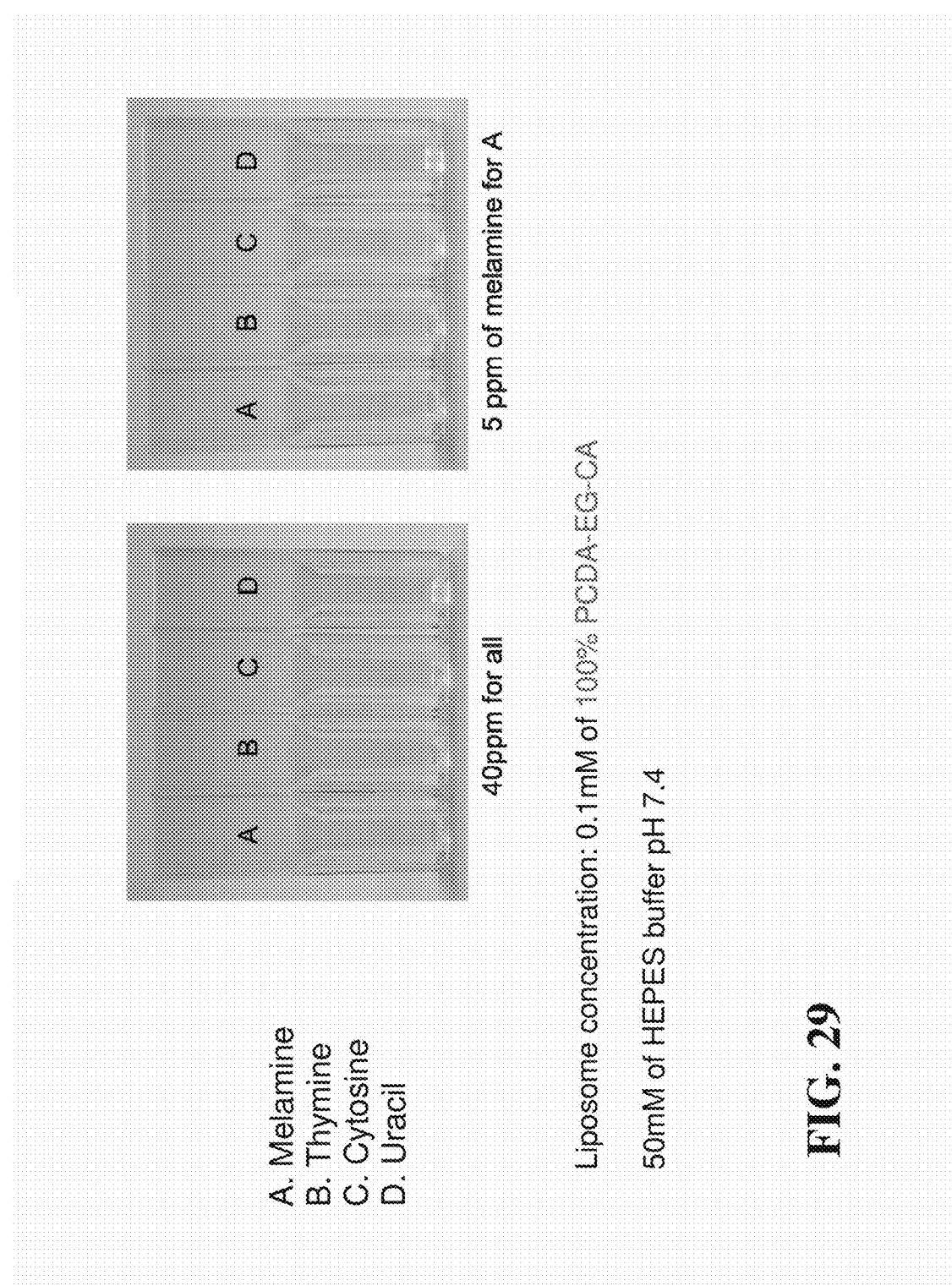

FIG. 29 shows the visible color change of the PCDA liposomes for melamine as compared to thymine, cytosine, and uracil.

Figure 30:
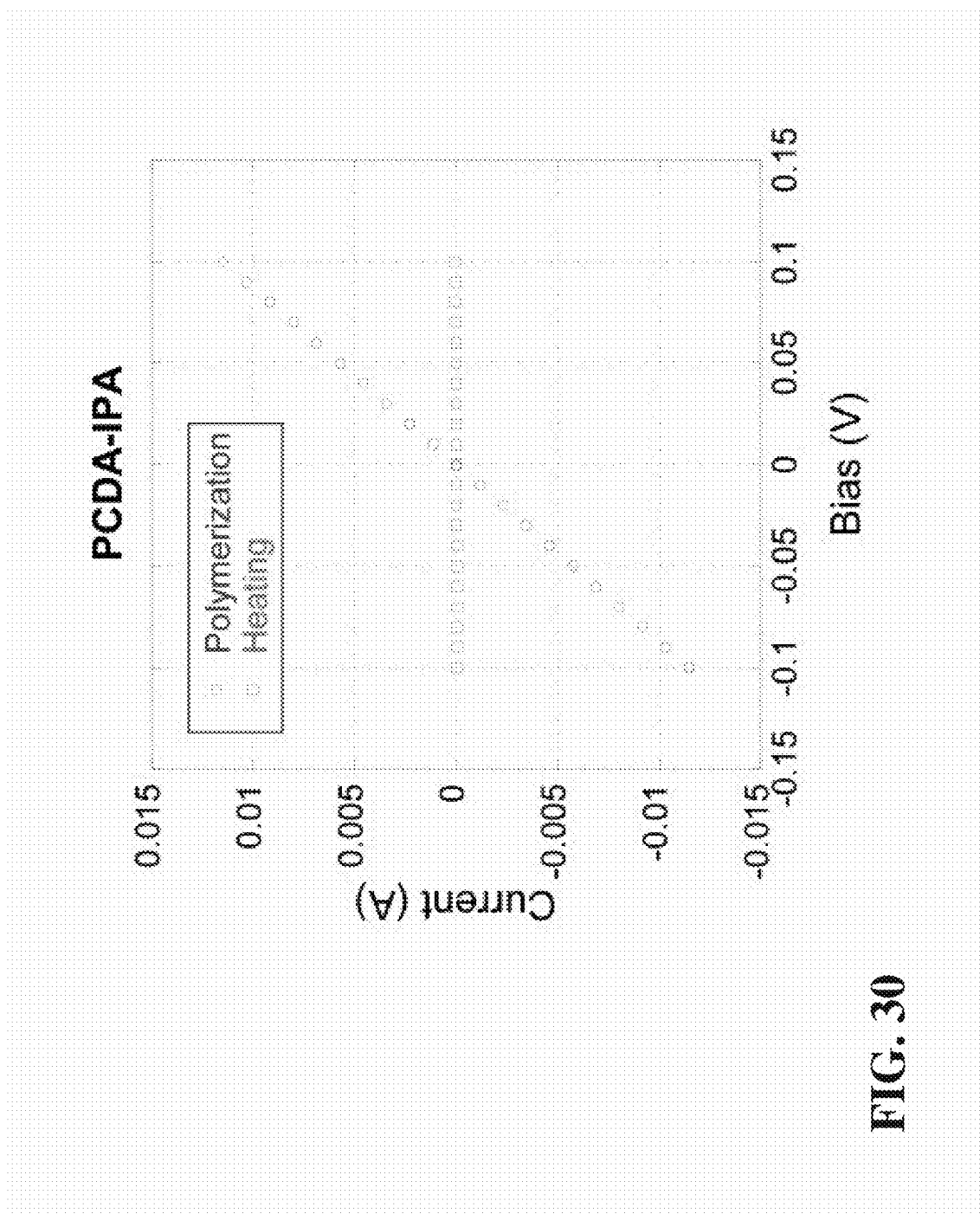

FIG. 30 graphically depicts current (A) versus bias (V) for PCDA-IPA.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to polydiacetylene-based self-signal amplifying sensors, arrays, and diacetylene constructs having fluorescence and target sensing capabilities. The present materials can be used to provide biological sensors and fluorescent labeling materials that are biocompatible, are not self-quenching, and are easily conjugated to a variety of molecules for selective sensing and recognition of target analytes. For example, a sensor capable of detecting a virus, a toxin, bacterium, or other target can be prepared by coupling an affinity component capable of specifically binding to the target onto a terminal group of diacetylene or other lipid molecule, and then mixing it with diacetylene to form a liposome. Such fluorescent materials may also be used to detect or localize proteins in living cells.

Polydiacetylenes (PDA) are conjugated polymers that may include a backbone of alternating double and triple bonds and may be formed from the 1,4-addition polymerization of 1,3-diacetylenes, for example. Polydiacetylenes generally absorb well in the visible region of the electromagnetic spectrum, and hence are highly colored, ranging from blue to yellow. Diacetylene monomers can form various ordered systems, including crystals, liquid crystals, liposomes, films, and wires that are polymerized to form a polymer. Liposomes can be made from monomers with diacetylene chains and polar head groups; e.g., phosphotidylcholines and analogues thereof. The liposomes can be polymerized with UV light or γ-radiation. Monomer films can be formed by Langmuir-Blodgett methods or cast from solvents and polymerized with UV light or γ-radiation. The choice of monomer structure, conditions of liposome or film formation, and polymerization conditions can each affect the conjugation length of the polydiacetylene backbone, and hence the color of the system.

Upon heating, for example, the polymerized PDA system can undergo a change in the effective conjugation length, from the longer length forms (blue and purple) to the shorter length forms (red and yellow). This change may be attributed to the side-chains moving and repacking upon being heated. Soluble polydiacetylenes show solvo-chromic behavior and polydiacetylene films often change color upon exposure to solvent vapors. Polydiacetylene films and liposomes formed from diacetylene surfactants also often change color with a change in pH. In the case of packed polymer arrays that form films and liposomes, changes in the environment that affect the organization and packing of the side chains off the conjugated backbone can affect the conjugation length and hence the chromic and electronic properties of the polymer.

Conjugated polymer-based sensor systems provide a sensitive way to measure a binding event. This is because an environmental change at a single site along the conjugated polymer chain can affect the properties of the collective system, resulting in signal amplification. An affinity component, being a molecule having affinity for a target, can be coupled to a PDA sensor whereupon binding of the target causes a color change. For example, a biological material can be used as a receptor with a synthetic conjugated polymer having a tunable signal amplification property, where the specificity of the system can provide selectivity in sensor design. In this respect, biological and synthetic conjugated polymer hybrid sensors can be made by rational design. For example, a component having affinity for a target or analyte can be coupled to a polymer using organic or bioconjugated synthesis methods and molecular assembly in order to make a sensor that can realize high sensitivity and high selectivity.

Polydiacetylene films and liposomes can be used in chromogenic assays that depend upon color change. For example, binding of a target ligand incorporated in a blue polydiacetylene film or liposome can perturb the side chains of the polydiacetylene, and hence change the conjugation length of the polydiacetylene, resulting in a color change to red. Such a color change is measurable. For example, when a diacetylene film or liposome is exposed to UV light at 254 nm, polymerization between adjacent diacetylenes occurs and the diacetylene becomes blue. Subsequently, when a polymerized polydiacetylene supramolecule is stimulated, for example by temperature, pH, friction, a surfactant, solvent, or binding of a target molecule, its color can transition to red. Polydiacetylene color transition can be dependent on the length of π-conjugation in the polymeric bonds and the structure of the resulting molecule. Accordingly, various types of sensors can be prepared by measuring the change in a polydiacetylene polymeric bond.

The PDA conjugated polymer exhibits pressure-sensitive mechanochromism. In particular, polydiacetylene in the blue phase is not emissive but the molecule produces red fluorescence when it transforms to the red phase by external stimuli, such as temperature, pH, ions, solvent, stress, and/or ligand interactions. The color change is believed to appear from the conformational change of the conjugated backbone of PDA induced by the external stimuli.

A topochemical polymerization method through 254 nm UV irradiation can be used to polymerize well-packed diacetylene monomers with a high degree of spatial order, such as that found in Langmuir-Blodgett monolayers and self-assembled liposome bilayers. Other methods include polymerization using thermal energy and nanoscale polymerization by means of scanning tunneling microscopy (STM).

Photo-induced topochemical polymerization converts transparent diacetylene monomers into a conjugated PDA having blue color. The absorption $\lambda_{max}$ of the blue phase is at about 640 nm. Upon external stimuli, the absorption $\lambda_{max}$ shifts from about 640 nm (the blue phase) to about 540 nm (the red phase) and the triggered red phase of PDA is fluorescent. By applying this environmental sensitive property of PDA combined with rational receptor design, PDA liposome-based self-signaling microarrays can be designed that selectively and sensitively detect a target analyte. The pressure-sensitive mechanochromism of PDAs can be used as a colorimetric biosensor for detecting various targets due to shape change of the molecule that accompanies the recognition or binding event.

In some embodiments, the sensor comprises a hydroxyphenyl-benzoxazole (HBO) derivative and a plurality of diacetylene monomer. At least a portion of the diacetylene monomer is coupled to one or more affinity components having affinity for one or more respective targets. The sensor exhibits a change in fluorescence or conductivity when an affinity component interacts with a respective target. For example, an affinity component may be an antibody and a target may be an antigen.

The affinity component may also be a molecule that is sensitive to an environmental change and the target may be an alternate conformation of the affinity component that is triggered by the environmental change. For example, the affinity component may be sensitive to temperature so that a temperature change causes the affinity component to have an affinity for an altered conformation of itself; i.e., where the target is the altered conformation. Upon rearrangement of the affinity component and binding or forming the new altered conformation, the sensor exhibits a change in fluorescence or conductivity.

The present sensors can be incorporated into microarrays. For example, microarrays are solid substrates composed of immobilized antibodies, aptamers, or peptides serving as probing molecules for the detection of specific targets. The present sensors may be used to generate a sensitive and label-free sensory signal at a binding recognition event that is readily applicable to the detection of many different proteins.

The need for protein microarrays has increased rapidly for investigating particular proteins in diseases and for high throughput drug discovery. Many drugs are designed to have specific functions on proteins; thereby, development of reliable protein microarrays would facilitate the realization of high throughput drug development and screening. However, a low cost, reliable protein microarray remains a significant challenge especially given the difficulty in devising an effective label-free detection strategy.

Figure 1A:
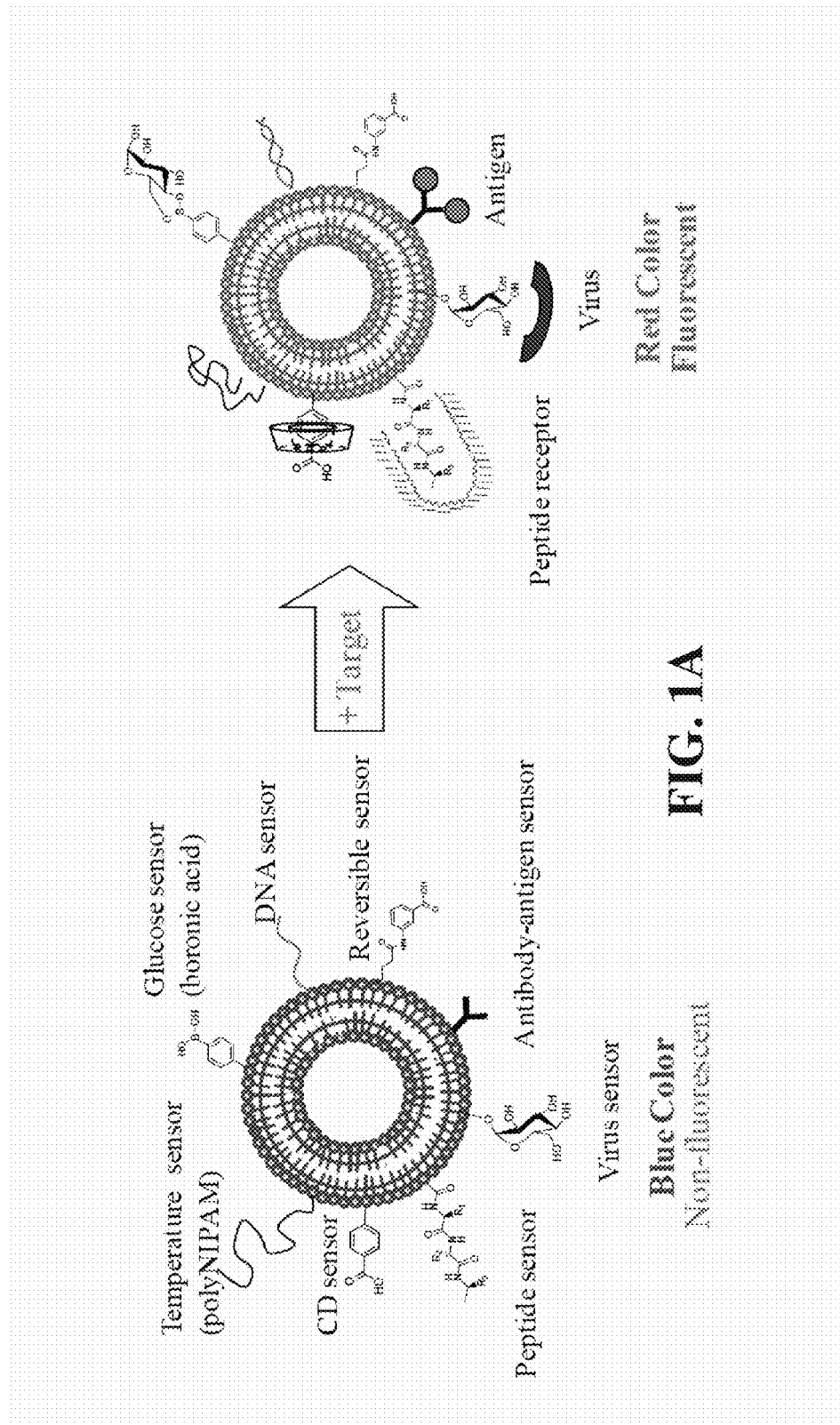

The present technology includes polydiacetylene (PDA)-based fluorescent sensors having label-free detection capability; e.g., FIG. 1. Molecular interactions between the affinity component at the PDA liposome surface and the target analyte molecule produce fluorescence emission as a sensitive and label-free sensory signal. The sensors can be used to form a PDA platform having a user-customizable capacity allowing convenient high throughput screening and easy modification for specific needs. For example, these sensors can include epoxy-modified PDA liposome systems that are sensitive to heavy metals and organic compounds, such as mercury and melamine. Such sensory systems can also be used to detect molecules such as glucose and nerve gas. Epoxy-modified liposomes can also be adapted for antibody-antigen pair detection; e.g., IgG antigen and antibody pair for IFN-γ. The sensors show excellent selectivity. The present sensors can also be adapted for use as nucleic acid aptamer screening devices. Besides the fluorescence detection scheme of the PDA liposome, the sensors can be used in electrochemical sensor cells by using PDA nanowires.

The present technology also provides a conjugation method between PDA liposomes and biological molecules. Molecular interactions between the affinity component at the PDA liposome surface and the target molecules can produce a fluorescent signal as well as a visible color change as a sensitive, selective, and label-free sensory signal. Examples of highly selective PDA microarrays have been developed for potassium detection, highly emissive and stable organic nanoparticles for immunofluorescence labeling, mercury (II) detection, glucose detection, and melamine detection. These examples demonstrate that the PDA-liposome layers that can be applied for any custom-made affinity component making the sensor adaptable and useful as a universal detection system.

Figure 1B:
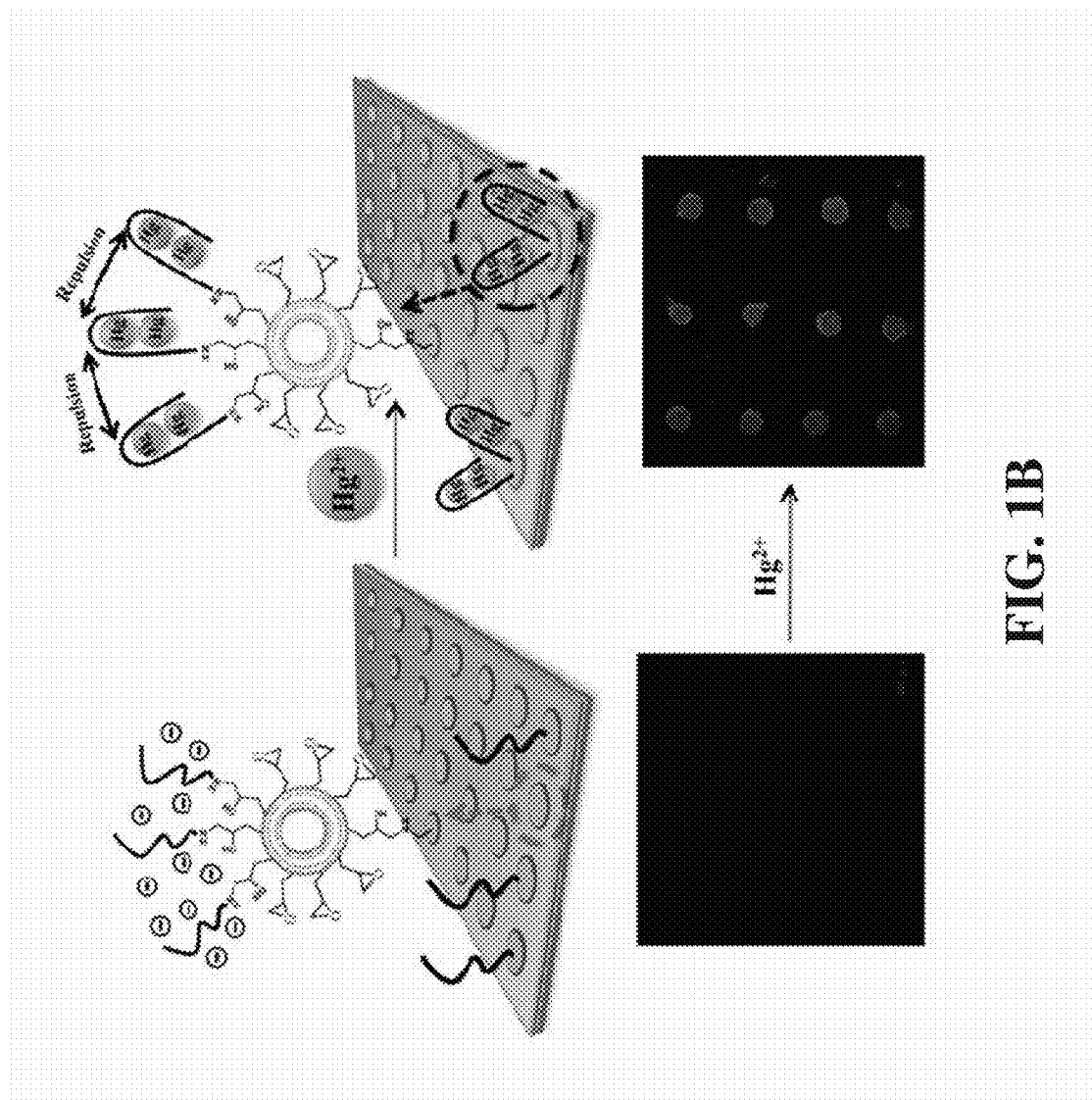

The sensor can include a reversible design in order to suppress false signals. In particular, because the design utilizes the mechanochromism of PDA, non-specifically bound analytes can possibly trigger the color change and fluorescent signal generation. Considering this possibility, PDA has been synthesized that has the capability of reversible color change. Hydrogen bonding by the two amide groups combined with aromatic interactions between benzene rings allows the PDA to exhibit this reversible feature, as shown in FIG. 1B. The ethylene oxide side chains reduce nonspecific binding. This design principle is readily applicable to a label-free sensor.

A PDA microarray can be made for selective potassium detection. Detection of potassium levels in humans is very important but selective detection of physiological potassium is a challenging task due to the presence of sodium in much higher concentrations. In the sensor design, a G-rich ssDNA of SEQ ID NO: 1 (5'-GGTTGGTGTGGTTGG-3') is used that can fold into a G-quadruplex via intramolecular hydrogen bonding by wrapping around a potassium ion exclusively. The PDA liposome is designed in such a way that the G-rich ssDNA probes are presented densely at the liposome surface and upon binding with K+ the resulting bulky quadruplexes repulse each other. The steric repulsion of the quadruplexes induces the perturbation of the ene-yne backbone of PDA liposomes and produces a color change from blue to red where the red fluorescence provides a label-free sensory signal. This sensor demonstrates that sensitive self-signaling is achievable by means of a rational design of receptor groups and demonstrates molecular interactions between the receptor group and the target molecule without any labeling.

The sensor can be configured to make a highly emissive and self-signal generating PDA liposome for immunofluorescent labeling. For example, highly emissive self-assembled organic nanoparticles having a dual color capacity for targeted immunofluorescence labeling can be made using the present technology. Well-defined synthetic PDA liposomes having imbedded organic nanoparticles with high quantum yield of about 38% can be formed through directed self-assembly with functionalized diacetylene surfactants. The surface of the liposomes can be readily functionalized with various biological molecules. Selective targeting and dual color visualization of patterned avidin arrays can be used for selective immunofluorescence labeling.

Figure 2:
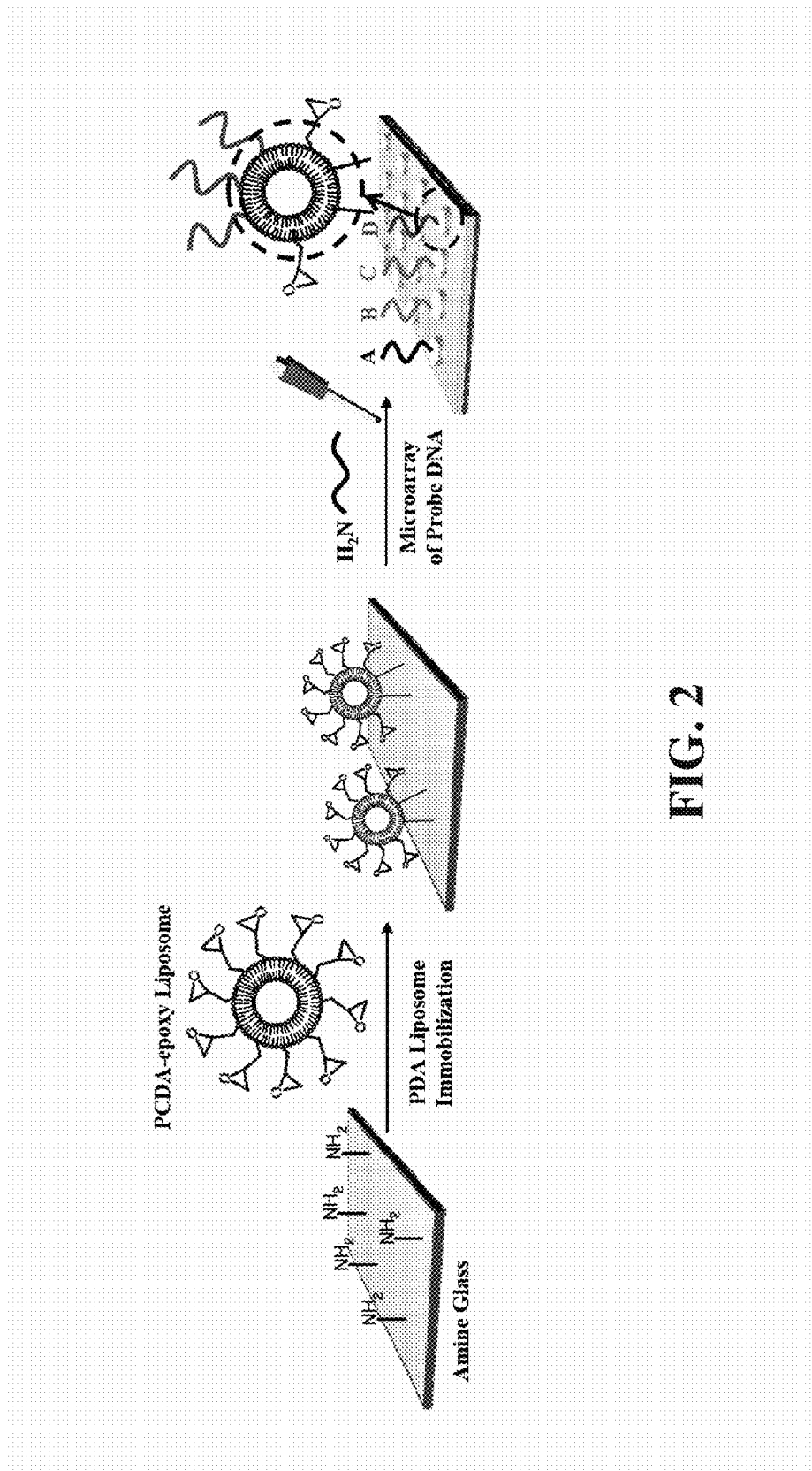
FIG. 2 depicts epoxy-functionalized diacetylene liposomes for tethering of proteins and other biological receptors after liposome immobilization on a substrate. The epoxy coupling group binds the sensors to the surface where different sensors with different DNA affinity components are spotted to allow for user-prepared microarrays.

Universal bioconjugation platforms for high throughput detection with various receptors can be made using the sensors. To achieve a protein microarray having a high throughput capacity, various proteins and biological receptors must be present at the microarray surface. This requires tethering of proteins after liposome immobilization on a substrate for both convenience and to allow for user-prepared microarrays. For example, one or more particular proteins can be affixed to the substrate surface to make a customized array. Self-assembling diacetylene molecules having an epoxy group can be used for this purpose as a carboxylic acid group provides a versatile functional group for bioconjugation with many biological molecules through their ubiquitously present amine groups. With reference to FIG. 2, a design strategy is shown to achieve post-tethering of various biological molecules onto a diacetylene liposome layer. The liposome will comprise an epoxy-modified diacetylene. The epoxy units can be used for both liposome tethering onto the substrate and for the bioconjugation. Various biological receptors can be immobilized depending on the target biological molecules.

A mercury sensor can be made by means of the epoxy-PDA liposome microarray. The mercury sensor uses epoxy-modified PDA liposomes and post-immobilization of the mercury-binding DNA sequence of SEQ ID NO: 2 (5'-TTCTTTCTTCCCCTTGTTTGTT-3') on the tethered epoxy-modified liposome layer. This construct demonstrates the versatility of the system. The microarray shows excellent selectivity between the target Hg ion versus other ions such as Cd, Na, K, and Zn. Upon binding with mercury, the microarrays produce a strong red emission but did not show any change toward the other metal ions tested.

Figure 3:
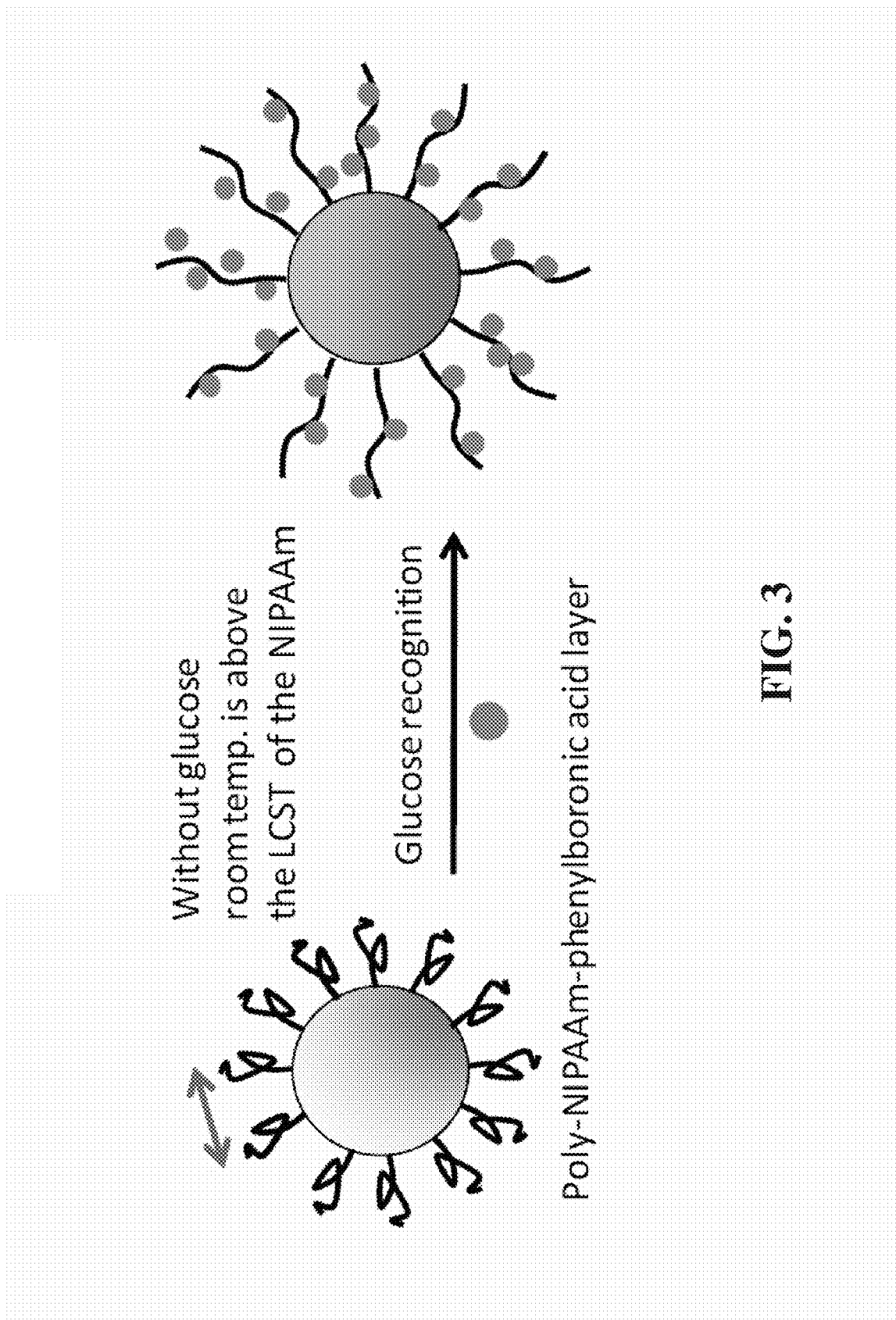
FIG. 3 depicts a glucose sensor, where without glucose, room temperature is above the lower critical solution temperature (LCST) of the poly(N-isopropylacrylamide)-pheylboronic acid layer and the sensor fluoresces red. Binding of glucose changes the poly(N-isopropylacrylamide)-pheylboronic acid layer affinity component and shifts the color to blue.
Figure 4:
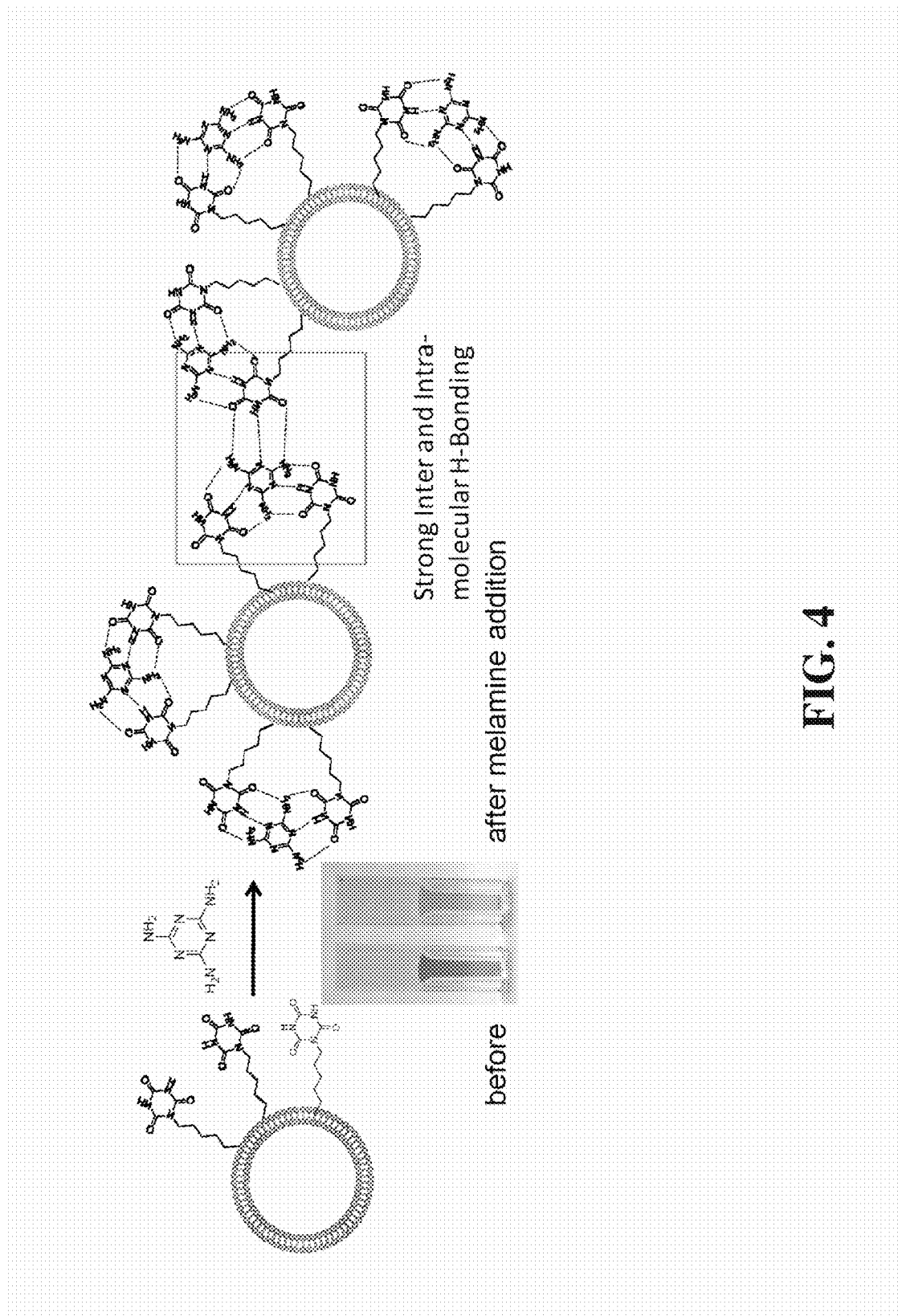
FIG. 4 depicts a melamine sensor that shifts from blue to red after melamine addition.

The sensor can be configured to provide a smart glucose sensor. The smart glucose sensor can change color reversibly in the presence of glucose. An embodiment of the concept is illustrated in FIG. 3. Copolymers of poly(N-isopropylacrylamide) (PNIPAM) having phenyl boronic acid units are tethered to the surface of PDA liposome. When the phenyl boronic acid units recognize glucose they are charged and the low critical solution temperature (LCST) of the copolymer increases. This overall change induces the swelling of the copolymer and the color changes from red to blue.

The sensor can be configured to provide a melamine sensor. Ingestion of melamine may lead to reproductive damage, bladder cancer, and kidney failure. A self-signaling melamine sensor can be developed based on PDA liposome. The PDA liposome demonstrates good selectivity and sensitivity can be used for food safety and food container examination.

Figure 5:
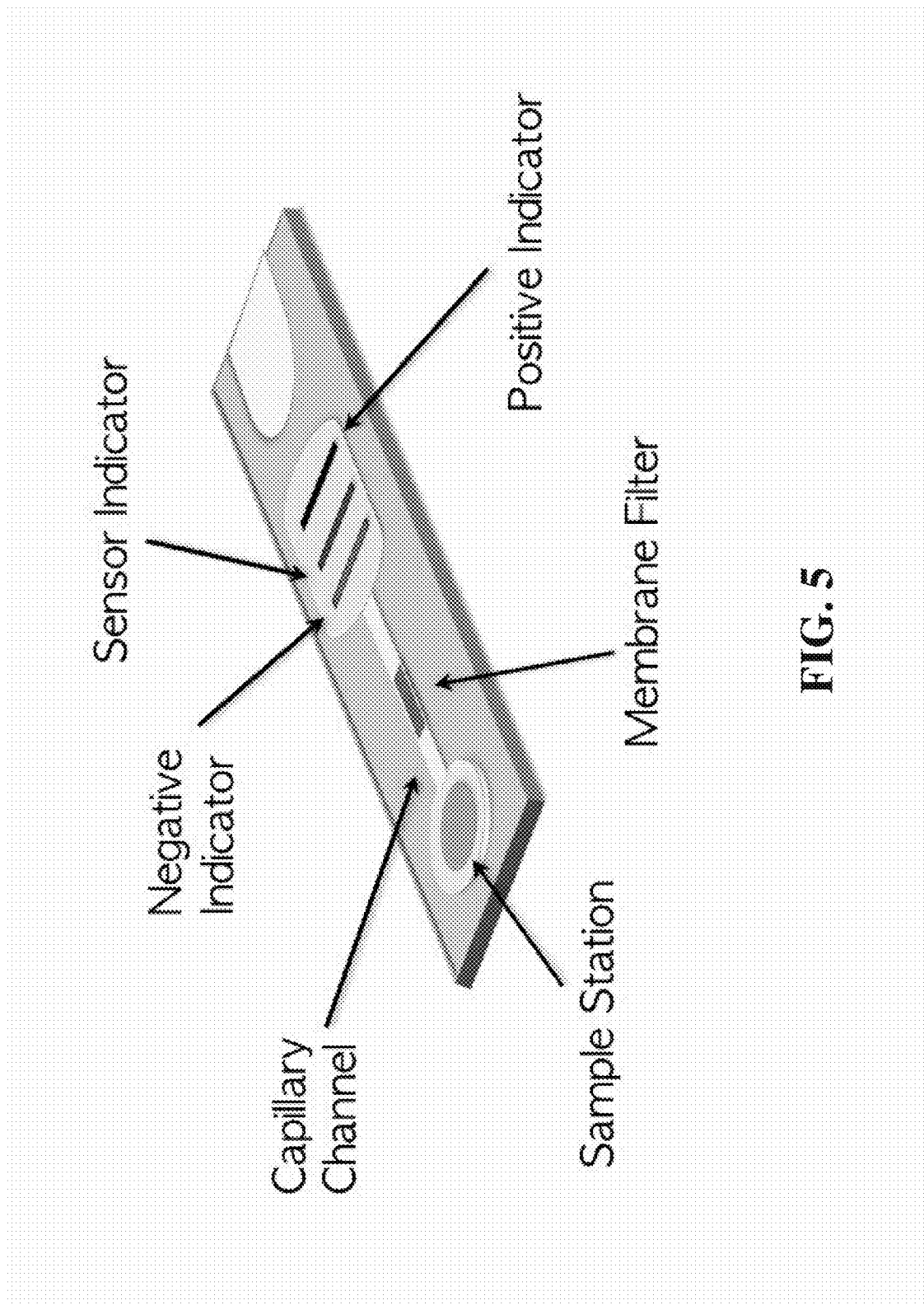
FIG. 5 is an embodiment of a biosensor device that can employ various sensors.

The present technology can be used to fabricate biosensor devices using the various PDA sensors described herein. The biosensor device can be easily fabricated at a low and can provide a convenient colorimetric detection with high fidelity. With reference to FIG. 5, an embodiment of the structure and component of a biosensor device is shown. For example, the device can be built on an etched glass slide as a micro fluidic device. The developed PDA-liposomes for potassium detection will be used. There can be two control lines with different PDA-liposomes, one as a positive control that should be turned on and the other a negative control that should not be turned on. Depending on the test sample, a membrane with a specific molecular weight cut-off can be used to provide better selectivity for samples having various proteins. The device can incorporate various specific sensors, such as the aforementioned potassium sensor, mercury sensor, melamine sensor, glucose sensor, and various protein sensors.

Figure 6:
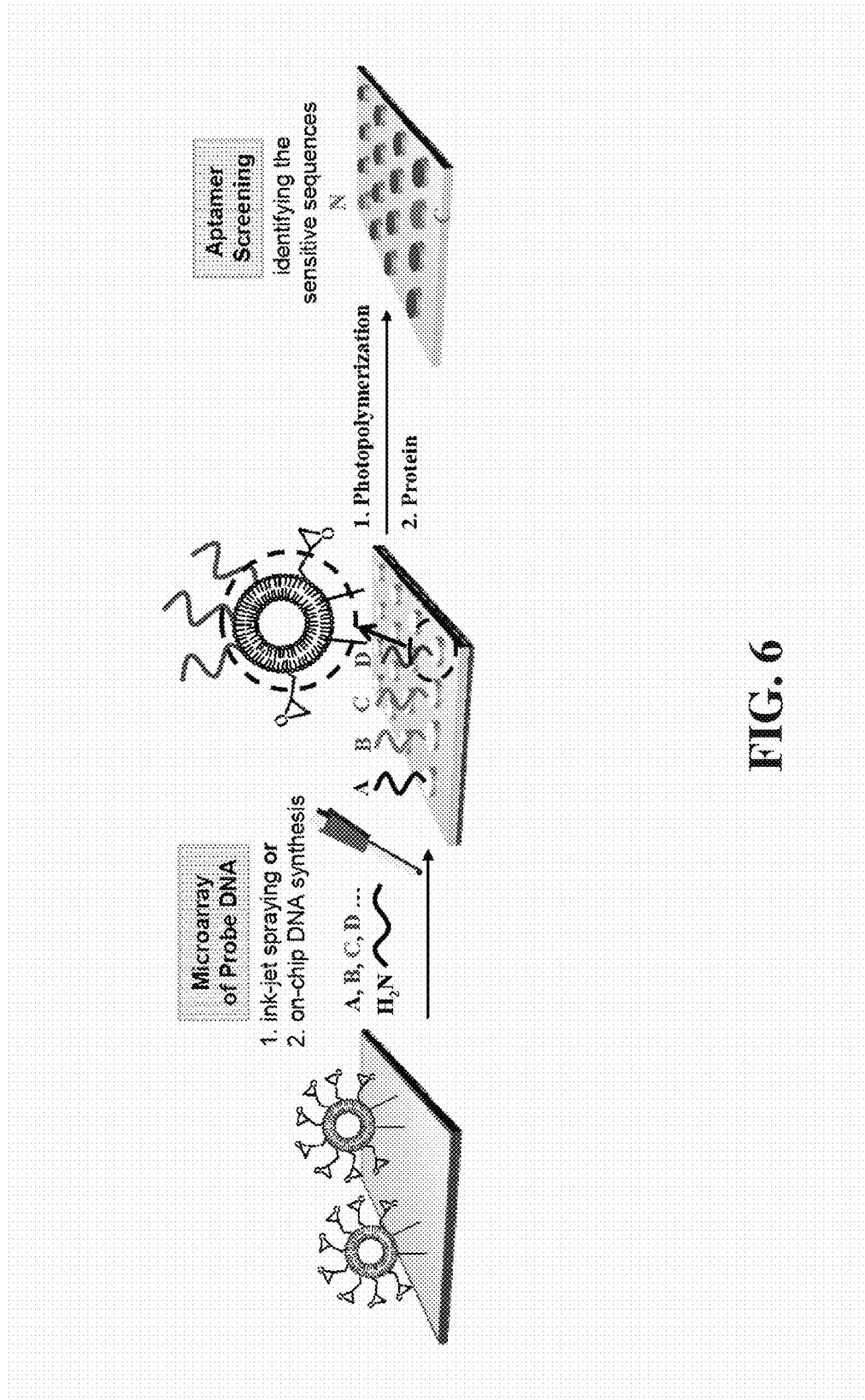
FIG. 6 depicts a schematic for preparing a microarray of probe DNA by coupling particular sensors having particular DNAs to particular locations of the array. The array can be used to screen the particular DNAs for binding activity (i.e., DNA aptamers) to a protein target.

High throughput aptamer screening can be performed utilizing PDA-liposomes. An aptamer is a specific nucleic acid sequence, such as RNA or DNA, that has a specific interaction with a target analyte, for example metal ions or proteins. DNA aptamers were used in development of the potassium sensor and the mercury sensor as described herein. However, the PDA-liposome system can also be efficiently and effectively used for aptamer screening. Various DNA sequences can be tethered to an epoxy-modified PDA liposome layer either by microarraying or on-chip DNA synthesis. High throughput can be achieved by applying ink-jet printing of DNA sequences as well. Solutions having a target analyte of interest will be spread on top of the PDA-layer and the sequences that are turned on due to binding of the target with a particular DNA coupled PDA-liposome will be identified. An embodiment of aptamer screening is schematically illustrated in FIG. 6.

Sensitive and versatile conductivity-based sensors can be formed of PDA nanowires. Besides the fluorescence detection scheme of PDA, electrochemical sensor devices can be constructed using PDA nanowires. Diacetylene molecules having charged groups can self-assemble into a nanowire with cations and the diaceytlene units can be efficiently photopolymerized inside the nanowire. For example, the nanowires can be drop cast onto a glass slide and gold electrodes prepared on the top of the nanowire film using the metal evaporation methods. The nanowire is not conducting at all before photopolymerizaton. After topochemical photopolymerization, the resulting PDA nanowire film shows high conductivity. An example of making a nanowire sensor system is shown in FIG. 7. Upon heating the nanowire to disturb the π-conjugation of the conducting PDA backbone, the conductivity drops down to the insulator level, as shown in the inset graph marked "c" in FIG. 7. The sensitive conductivity change following external stimuli can be efficiently used in a sensitive and label-free sensor design. This system can be used to detect clinically important biological markers by using PDA nanowire devices.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail.

EXAMPLES

Example 1

Detection of Potassium ($K^+$) Using Polydiacetylene (PDA) Liposome-Based Microarrays Polydiacetylene (PDA) liposome-based microarrays can be used to selectively detect potassium even in the presence of sodium and other ions using the sensing functionalized polydiacetylene constructs of the present technology. Potassium ($K^+$) is an important cation in biology and quantitative detection of the extracellular potassium level in the blood stream is also important. The typical physiological concentration of potassium and sodium in the blood stream is about 3.5-5.3 mM and about 135-145 mM, respectively. However, selective detection of physiological potassium is a challenging task due to the presence of sodium in a much higher concentration. The present functionalized PDA liposome microarray sensor has coupled ssDNAs having a guanine-rich sequence SEQ ID NO: 1 (5'-GGTTGGTGTGGTTGG-3') as a selective probe for potassium detection. The sensor utilizes the fact that the G-rich ssDNA can fold into a G-quadruplex via intramolecular hydrogen bonding by wrapping around a potassium ion exclusively.

The functionalized PDA liposome microarray can be designed and implemented in such a way that the G-rich ssDNA probes can be densely oriented at the liposome surface, and upon binding with $K^+$, the resulting bulky quadruplexes repulse each other as illustrated in FIG. 8. Although not wishing to be bound by any particular theory, it is believed that the steric repulsion of the quadruplexes induces the perturbation of the ene-yne backbone of PDA liposomes and produces the color change from blue to red and red fluorescence as well.

The NHS-activated (N-hydroxysuccinimide) carboxylic-acid-containing diacetylene shown in FIG. 8 (PCDA-linker-NHS) includes self-assembled diacetylene liposomes prepared by using a 1:1 mixture of the PCDA-linker-NHS and 10,12-pentacosadiynoic acid (PCDA). The G-rich ssDNA accessory molecule was covalently linked to the liposome surface by means of conventional amide chemistry between the amine-modified G-rich ssDNA and the PCDA-linker-NHS. The self-assembled and functionalized PDA liposomes were then printed onto an amine-modified glass solid substrate using a manual microarrayer in a humidity chamber and photopolymerized.

FIG. 8B schematically illustrates the steric repulsion and the resulting conformational change of the PDA liposome, which is induced by G-quadruplex formation with $K^+$ selectively. The selective G-quadruplex formation of the PDA liposomes with $K^+$ was confirmed by using circular dichroism (CD) analysis as shown in FIG. 9A. The characteristic absorption bands at 270 nm and 290 nm of the quadruplex were observed only when $K^+$ was added to the solution of the PDA liposomes. The CD analysis also shows that the presence of $Na^+$ does not interfere with the selective $K^+$ recognition. Contamination with Na+ at levels about 30 times greater (100 mM) than the concentration of K+ in the assay essentially did not hinder the quadruplex formation of the G-rich ssDNA probe with $K^+$ (3 mM).

FIGS. 9B and 9C show the UV-Vis absorption spectra and photoluminescence (PL) emission spectra of the G-rich ssDNA-tethered PDA liposome solution upon addition of KCl solution in various concentrations. The solution was incubated at 25° C. for 3 h. As the concentration of K+ increases, the absorption band at 650 nm (blue phase) decreases and the new absorption band at 550 nm (red phase) increases. The detection limit shown in FIG. 10B is about 0.1 mM, and that is suitable for the detection of the physiological potassium level (about 3.50-5.30 mM). The same liposome solution did not show any change even upon addition of about 100× higher concentration of $Na^+$, providing excellent selectivity. The fluorescence intensity of the PDA liposome microarray also increased gradually with the increasing concentration of $K^+$ (FIG. 10C). As the incubation time at 25° C. increases, the PL intensity also increases (FIG. 10D).

Solid-state liposome arrays were further developed for selective potassium detection. The G-rich ssDNA modified liposome solution was spotted onto amine-modified glass substrates using a manual microarrayer, followed by incubation at 30° C. for 3 h under 90% humidity condition to prevent the liposomes from drying out, and subsequently photopolymerized with a 1 mW/$cm^2$ 254 nm UV lamp for 2 min. Twenty milliliters of 5 mM NaCl solution and 20 mL of 5 mM KCl solution were then added onto the glass substrate, respectively. As shown in FIG. 10A, no fluorescence was observed after adding the NaCl solution and before adding the KCl, while the red fluorescence emission was turned on as an indication of the K+ detection after adding the KCl solution followed by 30 min of incubation at room temperature (FIG. 10B). The results demonstrate that the immobilized liposomes having G-rich ssDNA selectively detect K+ even in the presence of Na+ because the presence of Na+ does not interfere with the selective K+ detection.

Detection limits in the solid state were determined as follows. FIG. 10C shows the fluorescence microscope images of the PDA microarrays of the present technology after incubation with $K^+$ solutions in various concentrations at room temperature for 30 min. The detection limit for the 30 min incubation in the microscope images is 0.5 mM KCl. The correlation curve between the fluorescence intensity and the amount of K+ is shown in FIG. 10D, and therefore, a quantitative analysis of an unknown K+ concentration is also achievable.

In summary, the present sensors can be used to develop a highly selective PDA liposome-based system to detect $K^+$ even in the presence of $Na^+$. The tethered G-rich ssDNAs at the liposome surface provide selectivity by wrapping around $K^+$ selectively to form quadruplexes. The bulky quadruplexes repulse each other due to steric hindrance and induce the ene-yne backbone perturbation of the PDA liposomes. This selective event triggers the color change from the blue phase to the red phase of the PDA liposome and also produces red fluorescence emission. Quantitative analysis of $K^+$ concentration can be performed using the PDA liposome microarray. The present technology therefore provides solid-state liposome arrays for selective potassium detection in biological samples.

The following materials and methods were employed in developing the potassium sensor. 10,12-pentacosadiynoic acid (PCDA) was purchased from GFS Chemicals. 2,2'-(Ethylenedioxy)bis-(ethylamine) (EDEA), N-hydroxysuccinimide (NHS), and N-(3-Dimethylaminopropyl)-N6-ethylcarbodiimide (EDC), Succinic Anhydride (SA) were purchased from Sigma-Aldrich Chemical Co. Amine modified G-rich ssDNA SEQ ID NO: 1 (5'-GGTTGGTGTGGT-TGG-3') oligonucleotides were purchased from Integrated DNA Technologies, Inc. Dialysis membrane was purchased from Pierce (Slide-A-Lyzer Dialysis Cassette, 20,000 MWCO, 0.1-0.5 mL capacity). $^1$H NMR spectra (500 MHz) were obtained using a Varian Inova 500 NMR instrument. UV/Vis absorption spectra were taken on a Varian Cary50 UV/Vis spectrophotometer. Fluorescence spectra were obtained using PTI QuantaMaster™ spectrofluorometers equipped with an integrating sphere. Fluorescence images were taken by Olympus BX51 W/DP71 fluorescent microscope. Circular dichroism spectra were obtained on an Aviv model 202 Circular Dichroism Spectrometer at 6° C.

Synthesis of PCDA-Linker-NHS: The diacetylene monomers were prepared by coupling N-hydroxysuccinic esters of PCDA. A procedure for the preparation of PCDA-Linker-NHS is shown in FIG. 11 and includes the following aspects. Monomer synthesis: (a) N-hydroxysuccinimide, N-(3-Dimethylaminopropyl)-N6-ethylcarbodiimide hydrochloride, methylene chloride, 25° C., 2 hr. (b) 2,26-(Ethylenedioxy) bis(ethylamine), methylene chloride, 25° C., 2 hr. (c) succinic anhydride, N,Ndimethylformamide, 25° C., 2 h. (d) N-hydroxysuccinimide, N-(3-Dimethylaminopropyl)-N6-ethylcarbodiimide hydrochloride, methylene chloride at 25° C. for approximately 2 hr.

PCDA-NHS(2): To a solution containing 1.00 g (2.67 mmol) of 10,12-pentacosadiynoic acid(1) in 10 mL of methylene chloride, was added 0.38 g (3.47 mmol) of N-hydroxysuccinimide and 0.38 g (4.01 mmol) of N-(3-Dimethylaminopropyl)-N6-ethylcarbodiimide hydrochloride at room temperature. The resulting solution was stirred at room temperature for 2 h. The solvent was removed in vacuo, and the residue purified by extraction with ethyl acetate to give 1.08 g (86.2%) of the desired diacetylene monomer PCDA-NHS (2) as a white solid: $^1$H NMR (300 MHz, CDCl$_3$): δ 0.85 (t, 3H), 1.20-1.62 (m, 36H), 2.21 (t, 4H), 2.60 (t, 2H), 2.85 (s, 4H), 7.18 (brs, 1H).

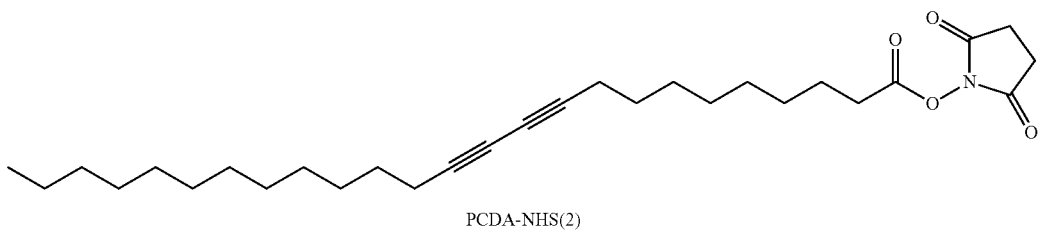 [SMILES: CCCCCCCCCCCCC#CC#CCCCCCCCCC(=O)ON1C(=O)CCC1=O]

PCDA-NHS(2)

PCDA-EDEA (3): To a solution containing 1.055 mL (7.21 mmol) of EDEA in 40 mL of methylene chloride, was added 1.00 g (2.12 mmol) of PCDA-NHS (2) at room temperature. The resulting solution was stirred at room temperature for 2 h. The solvent was removed in vacuo, and the residue purified by extraction with ethyl acetate. The solvent was removed in vacuo, and the residue was purified by column chromatography (9:1 chloroform:methanol) to give 490 mg (46%) of the desired diacetylene monomer PCDA-EDEA(3) as a pale blue solid: $^1$H NMR (300 MHz, CDCl$_3$): δ 0.89 (t, 3H), 1.27-1.64 (m, 35H), 2.21 (m, 6H), 2.92 (t, 2H), 3.45-3.63 (m, 14H), 6.21(s, 1H), 7.27 (brs, 1H).

sonication, the solution was filtered to remove aggregated liposome by using 1.0 μm nylon filter. To the 100 μL of following resultant suspension was added 50 μL (50 nmol) of amine modified G-rich ssDNA at 10° C. The residue suspension was stirred and stored in the incubator for 4 h at

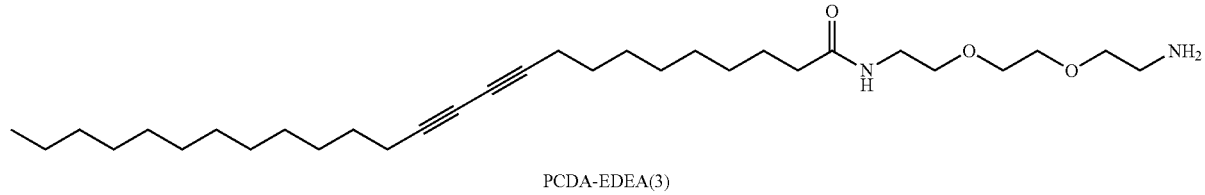 [SMILES: CCCCCCCCCCCCC#CC#CCCCCCCCCC(=O)NCCOCCOCCN]

PCDA-EDEA(3)

PCDA-EDEA-SA (4): To a solution containing 198.3 mg (1.98 mmol) of succinic anhydride in 10 mL of N,N-dimethylformamide was added 500 mg (0.99 mmol) of PCDA-EDEA (3) at room temperature. The resulting solution was stirred at room temperature for 2 h. The solvent was removed in vacuo, and the residue was purified by extraction with ethyl acetate to give 540 mg (90%) of the desired diacetylene monomer PCDA-EDEA-SA(4) as a white solid: $^1$H NMR (300 MHz, CDCl$_3$): δ 0.89 (t, 3H), 1.27-1.64 (m, 39H), 2.22 (m, 6H), 2.45 (t, 2H), 2.65 (t, 2H), 3.45-3.63 (m, 14H), 5.91 (s, 1H), 6.21 (s, 1H), 7.27 (brs, 1H).

37° C. The resultant suspension was sonicated again for 30 min at 80° C. and cooled at 5° C. for 6 h. The unbound G-rich ssDNA was removed by dialysis in di-water for 1 day. Above procedures have to be accomplished under or around 10° C. to remove the hydrolysis of N-hydroxysuccinimide (NHS) leaving group except the tethering of G-rich ssDNA on the surface of the diacetylene liposome and the second sonication.

Preparation of the Liposome Microarray: An amine-modified glass substrate was placed in a humidity chamber for 30 min at 30° C. The G-rich ssDNA tethered diacetylene

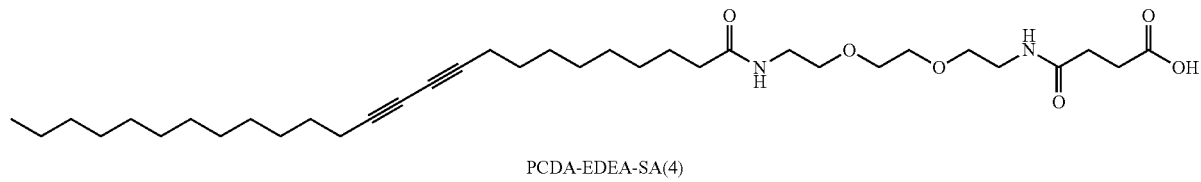 [SMILES: CCCCCCCCCCCCC#CC#CCCCCCCCCC(=O)NCCOCCOCCNC(=O)CCC(=O)O]

PCDA-EDEA-SA(4)

PCDA-Linker-NHS (5): To a solution containing 400 mg (0.66 mmol) of PCDA-EDEA-SA in 20 mL of methylene chloride was 114.1 mg (0.99 mmol) of N-hydroxysuccinimide and 190.1 mg (0.99 mmol) of EDC at room temperature. The resulting solution was stirred at room temperature for 2 h. The solvent was removed in vacuo, and the residue was recrystallized in ethyl acetate to give 250 mg (54%) of the desired diacetylene monomer PCDA-Linker-NHS as a white solid: $^1$H NMR (300 MHz, CDCl$_3$): δ 0.89 (t, 3H), 1.27-1.64 (m, 39H), 2.18 (m, 6H), 2.62 (t, 2H), 2.85 (s, 4H), 3.00 (t, 2H), 3.45-3.63 (m, 14H), 5.91 (s, 1H), 6.21 (s, 1H), 7.27 (brs, 1H).

liposome solution was spotted onto the amine-modified glass slide by using a manual microarrayer (VP 475, V&P scientific, INC) and stored for 4 h at 90% humidity. After rinsing with di-water and drying under a stream of nitrogen, the microarrayed glass substrate was exposed to 254 nm UV (1 mW/cm$^2$) for 2 min.

Potassium Detection of the Liposome Microarray (see FIG. 10A): 20 mL of 5 mM NaCl solution and 20 mL of 5 mM KCl solution was added onto the liposome microarray having the G-rich ssDNA, respectively, and the microarray was incubated for 30 minutes at room temperature before

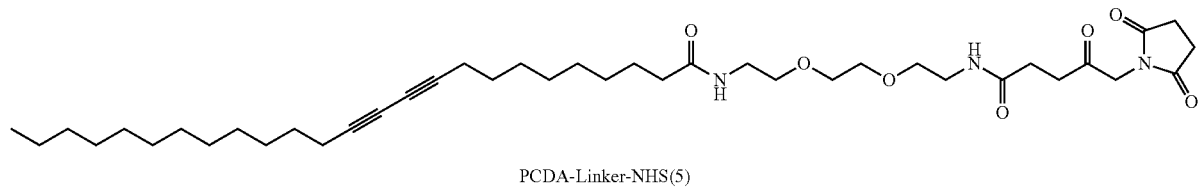 [SMILES: CCCCCCCCCCCCC#CC#CCCCCCCCCC(=O)NCCOCCOCCNC(=O)CCC(=O)CN1C(=O)CCC1=O]

PCDA-Linker-NHS(5)

Preparation of the G-rich ssDNA tethered Diacetylene Liposome: A mixture of the PCDA Linker-NHS (4) and PCDA (1:1 mole ratio) monomers was dissolved in 0.2 mL of dimethyl sulfoxide. The mixture solvent was added to di-water (10mL) and bath sonicated for 5 min to give the final concentration of lipid vesicle (1 mM). Following rinsing. The fluorescence images were obtained by using a fluorescent microscope (Olympus BX51 W/DP71).

Quantitative Data of Fluorescence Intensity with Various Concentrations of Potassium (FIGS. 10C and 10D): The liposome microarray was incubated with a solution containing various concentrations (0.5, 2.5, 5.0, 12.5, 25, and 50 mM: 0.01-1.0×10$^{-3}$ mol in 20 mL) of potassium for 30 min. The fluorescence images were obtained by using a fluorescent microscope (Olympus BX51 W/DP71) and the quantitative fluorescence intensities from the dots were analyzed by using IPLab 4.04 Software (BD Biosciences, USA). The data were obtained with five independent experiments. The error bar is standard deviation and each point represents the mean value.

Potassium Detection of G-rich ssDNA Modified Liposome Solution (FIGS. 9B and FIG. 9C): To a solution containing 200 µL of 1 mM solution of the G-rich ssDNA tethered liposome was added 1 µL of concentrated KCl solution to make the final concentration of 0.05, 0.1, 0.5, 1.0, 2.5, 5.0, and 10.0 mM at room temperature. UV spectrum and PL spectrum were taken after 3 hours incubation at room temperature.

Circular Dichroism (FIG. 9A): A solution of the G-rich ssDNA tethered liposome in di-water was prepared by above mentioned procedure. To a solution of the 0.25 mM G-rich ssDNA tethered liposome (200 µL) were added 10 µL of KCl and NaCl solution to make the final concentration of 3 mM for KCl and 100 mM for NaCl and the resulting liposome solution was incubated for 3 hours at room temperature. The CD spectrum of the liposome solution was measured at 6° C.

FIG. 12 shows the UV spectrum change of G-rich ssDNA tethered liposome solution upon adding NaCl.

Example 2

Highly Emissive Self-Assembled Organic Nanoparticles having Dual Color Capacity for Targeted Immunofluorescence Labeling Highly emissive organic nanoparticles can be developed using colloidal self-assembly of a hydroxyphenyl-benzoxazole (HBO) derivative and diacetylene monomers. Various heterocyclic molecules including HBO possess thermal stability and high electron mobility. HBO has a high extinction coefficient and excellent stability in the UV range and can function as a UV stabilizer. HBO also can undergo excited state intramolecular proton transfer (ESIPT) upon photoexcitation, as illustrated in FIG. 13A.

The molecule 1,4-di(3-(benzoxazol-2-yl)-4-hydroxyphenyl)-2,5-dihexyloxybenzene (DBO), as shown in FIG. 13B, was synthesized. The absorption and photoluminescence spectra of DBO are shown in FIG. 14C. A dilute solution of DBO in tetrahydrofuran (THF) has an absorption $\lambda_{max}$ at 335 nm assigned to syn-enol and emits at 518 nm, showing a large Stokes shift due to excited-state intramolecular proton transfer (ESIPT). A nanoparticle dispersion of DBO was prepared by adding THF solution of DBO to water to induce aggregate formation. The prepared nanoparticles in the mixed solution of THF:H$_2$O (1:9 v/v) show a broad aggregation band above 400 nm due to Mie scattering (FIG. 14C). Interestingly, their fluorescence quantum yield ($\Phi_F$) was 10%, which is more than 3 times larger than the quantum yield of the THF solution (3%). The enhanced fluorescence emission intensity in the aggregates is believed to originate from a more planar structure induced by J-type aggregation through intermolecular hydrogen bonding, evidenced by the absorption red shift by 40 nm from 335 nm, as shown in FIG. 14C.

To reduce the Mie scattering and prepare DBO nanoparticles having a well-defined size, amphiphilic surfactant molecules were used in order to direct the self-assembly of DBO. The surfactant molecules disperse DBO aggregates evenly by passivating the surface of the aggregates. Several amphiphilic molecules such as phospholipids, ionic surfactants, and diacetylenes were used to disperse and assemble DBO or random aggregates of DBO into more defined nanoparticle structures. All of these amphiphilic molecules served well as dispersion agents.

The following results were obtained by using a unique combination of diacetylene molecules as a dispersion agent. A 7:3 mole ratio of 10,12-pentacosadiynoic acid-aminobutyric acid (PCDA-ABA) and 10,12-pentacosadiynoic acid-2,20-(ethylenedioxy)-bis(ethylamide)-biotin (PCDA-Biotin) were mixed in HEPES buffer (0.5 mM) and then sonicated to form PCDA vesicles. 0.1 mL of 1 mM DBO in THF solution was then added into the 10 mL of PCDA vesicle solution and the mixture solution was sonicated for 10 min to form well-defined (80±10) nm of DBO nanoparticles having PCDA passivation layer as illustrated in FIG. 13C. The resulting suspension has a 1:50 mole ratio of DBO to PCDA and the SEM image of the self-assembled DBO-PCDA nanoparticles is shown in FIG. 13E. Note the significantly enhanced fluorescence emission intensity of the self-assembled DBO-PCDA nanoparticles in FIGS. 13D and 14C. The quantum yield of the self-assembled DBO-PCDA nanoparticles was 38%, which is almost 13 times larger than that of DBO in THF solution.

It is also interesting to note that the DBO-PCDA nanoparticles have strong anti-enol absorption at 320 nm. Considering the fact that only the syn-enol form can undergo ESIPT and the molecular rotation from antienol to syn-enol is suppressed in the solid state, observing the strong emission at 518 nm with about 200 nm of Stoke shift was unexpected. Without being bound by theory, it is believed that the DBO in the DBO-PCDA nanoparticles forms a J-type aggregation through intermolecular hydrogen bonding as illustrated in FIG. 14A. The planarized conjugated backbone of DBO and the restricted molecular rotation in the -aggregates are likely the origin of the largely enhanced 38% quantum yield.

First, as theoretical energy calculation studies and experimental data show that twisted conjugated organic molecules generally have a lower quantum yield, it is reasonable that the planarized conjugated backbone of DBO in the self-assembled J-aggregates has a larger quantum yield compared to DBO in solution. Other supporting experimental evidence includes the fact that a much longer lifetime is observed for the self-assembled DBO-PCDA nanoparticles than the DBO in THF solution. The lifetimes of the 518 nm emission band when excited at 380 nm were 0.42 ns and 6.26 ns for the DBO solution in THF and the DBO-PCDA nanoparticles, respectively. The lifetime of the 518 nm emission band when the DBO-PCDA nanoparticles were excited at 310 nm (anti-enol) was 6.41 ns, which is similar to the 6.26 ns of the syn-enol excitation. Other experimental studies show that the lifetime of HBO increases from about 10 ps at room temperature to 5.7 ns at 77 K as the molecular motion was restricted at the 77 K. The quantum efficiency of HBO also increases from 3.5% at room temperature to 37% at 77 K. These values of the lifetime and the quantum efficiency are in good agreement with what is observed for the DBO solution in THF and DBO-PCDA nanoparticles if the solid-state is considered as a mimic of the frozen solution at 77 K, when accounting for the restricted molecular movement in both cases.

To monitor photochemical stability, DBO-PCDA nanoparticles were exposed to a 6-W 254-nm. handheld UV light held 1 cm above the sample for 30 min. The fluorescence intensity of DBO-PCDA nanoparticles decreased only by about 15% upon the intense UV irradiation while other fluorescent organic dyes (Alexa Fluor 488) and conjugated polymers (poly(p-phenyleneethynylene) and poly(3-hexylthiophene)) experience about 80-90% of quenching under the same conditions (data not shown).

Application of the highly emissive and biotin-functionalized DBO-PCDA nanoparticles for immunofluorescence labeling was further investigated. First, sulfo-N-hydrosuccinimide-biotin (1 mg/mL in phosphate buffered saline (PBS)) was spotted on an amine-functionalized glass surface using a manual micro-arrayer (V&P Scientific, VP478A) (see FIG. 15A). Remaining active amines were blocked with poly(ethylene oxide) (see experimental details below) and subsequently avidin from egg white (1 mg/mL in PBS) was spread on the biotin-patterned glass slide. After thoroughly washing off unbound avidin, a 0.5 mM solution of the self-assembled DBO-PCDA nanoparticles in HEPES buffer was finally applied on the avidin-patterned glass slide. After removing non-specifically bound DBO-PCDA nanoparticles by rinsing several times with HEPES buffer, microscopic images were taken as shown in FIG. 15B. Green fluorescent was observed from only the avidin spots, demonstrating good selectivity and bright emission.

The self-assembled DBO-PCDA also has a dual color capability because the PCDA not only serves as a surfactant and a recognition unit for the target avidin spots but also can generate a sensory signal. A PCDA passivation layer was polymerized after self-assembling the biotinylated DBO-PCDA nanoparticles. The polymerized polydiacetylene (PDA) layer experiences perturbation of the conjugated backbone and undergoes mechanochromism from the blue form to the red form during the biotin-avidin recognition/binding. Because the red form is emissive, as anticipated, the red emission is observed when using a 600 nm long-pass emission filter with a 550 nm excitation filter, as shown in FIG. 15C.

In summary, DBO was synthesized and DBO with functionalized PCDA molecules were self-assembled to form well-defined DBO-PCDA nanoparticles. The DBO-PCDA nanoparticles show aggregation-induced fluorescence enhancement having a 38% quantum yield. Intermolecular hydrogen bonding is believed to form J-aggregates and allows intermolecular excited state proton transfer. Selective targeting and dual color visualization of patterned avidin arrays are achieved by using the highly emissive biotinylated DBO-PCDA nanoparticles to demonstrate the application of the organic nanoparticles for immunofluorescent labeling.

Experimental details include the following aspects. Glass slides were cleaned in boiling $H_2O:H_2O_2:NH_4OH$ (1:1:4 volume ratio) solution for 30 min, followed by piranha solution ($H_2O_2:H_2SO_4$, 3:7) etching after thorough rinsing with water and drying. The glass slides were further dipped in 2 wt % 3-aminopropyltriethoxysilane in toluene solution for 1 h, and were sonicated in toluene:methanol (1:1) and methanol for 3 min each to remove unbound silanes. The final amine functionalized glass slides were stored in a sealed container at 4° C.

One milligram of sulfo-NHS-biotin purchased from Aldrich was dissolved in 1 mL of phosphate buffered saline and used right after preparation and before the hydrolysis of sulfo-NHS. An amount of 2.2 mg succinimidyl-4-(N-maleimidomethyl)cyclohexane-1-carboxylate (purchased from Pierce, Co.) was dissolved in 200 mL DMSO and further diluted in DMSO:ethanol 2:8 volume ratio mixture. An amount of 2.4 mg of mono functional thiolated poly(ethylene oxide) (Mw=2400 g/mol, purchased from PolymerScience) was used in 10 mL of PBS. One milligram of Avidin from egg-white purchased from Aldrich was also dissolved in 1 mL of PBS buffer with 0.02 wt % Tween20 (PBST). Sulfo-NHS-biotin was spotted on an amine glass with a manual microarray (V&P Scientific, VP475A) and stored in a humidity chamber (Relative humidity about 90%) for 4 h. After rinsing with PBS buffer, remaining active amines were reacted with SMCC crosslinker and were blocked further with thiol-poly(ethylene oxide) in PBS and rinsed with water. Avidin solution was spread on the biotin spotted glass for 30 min.

After the avidin-biotin binding, the unbound avidin was rinsed off with PBST and stored in PBS until the next experiment. The avidin patterned glass slide was immersed in the biotinylated vesicle suspension for 30 min and examined with a fluorescence microscope (Olympus BX51). Amounts of 3.5 mmol of PCDA-ABA and 1.5 mmol of PCDA Biotin were dissolved in chloroform and filtered through a 0.45 mm syringe filter. After the evaporation of chloroform, 10 mL of 1 mM HEPES buffer was added in to give 0.5 mM PCDA. The homogeneous PCDA suspension was obtained via sonication for 15 min at the transition temperature of PCDA. Pre-determined amount (0.1 mL) of 1 mM DBO in THF solution was injected after or during the vesicle formation to get 1:50 DBO:PCDA mol ratio. And the final DBOPCDA vesicles were stored at 4° C. in the dark before use. Nanoparticles in THF:$H_2O$ 1:9 mixture were obtained by precipitation of 1 mL of 0.1 mM DBO in THF into 9 mL of deionized water during sonication.

Synthesis of DBO 2-(benzoxazol-2-yl)-4-bromophenol was performed as follows. 2-Aminophenol (2.51 g, 23.03 mmol) and 5-bromosalicylic acid (5.5 g 23.03 mmol) were added in 30 mL of polyphosphoric acid and the mixture was heated to 130° C. and stirred for 4 h. After cooling to room temperature, the reaction mixture was precipitated in ice-water, filtered, and washed with DI water. The product was recrystallized from acetic acid and dried in vacuo (yield 5.94 g, 88.9%). $^1$H NMR (300 MHz, $CDCl_3$): δ 11.44 (s, 1H), 8.16-7.04 (m, 7H).

tert-butyl-2-(benzoxazol-2-yl)-4-bromophenyl carbonate (1). 2-(benzoxazol-2-yl)-4-bromophenol (0.8 g, 2.76 mmol) was dissolved in dry, distilled tetrahydrofuran (THF) with di-tertbutyldicarbonate and (4-dimethylamine) pyridine (5 mol-%). When the reaction appeared complete by thin-layer chromatography (TLC), the solution was concentrated and precipitated in DI water, washed with ethanol. The product was dried in vacuo (yield 0.77 g, 74.5%). $^1$H NMR (300 MHz, $CDCl_3$): δ 8.44 (s, 1H), 7.77 (d, 1H), 7.65 (d, 1H), 7.58 (d, 1H), 7.38 (m, 2H), 7.2 (d, 1H), 1.58 (s, 9H).

Scheme S.1. Synthesis of tert-butyl-2-(benzoxazol-2-yl)-4-bromophenyl carbonate (1)

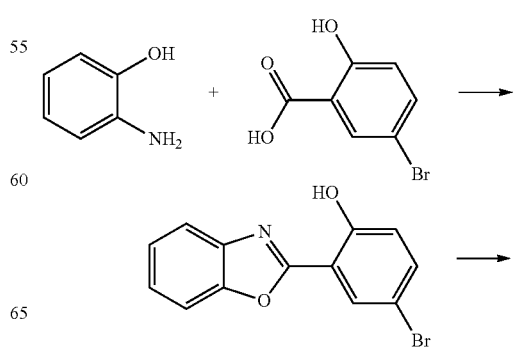

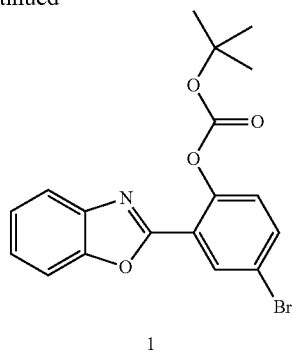

1

2,5-dibromo-1,4-dihydroxybenzene. Hydroquinone (50 g, 0.454 mol) was added in acetic acid (240 mL) and stirred vigorously. Bromine (46.6 mL, 0.91 mol) in acetic acid (200 mL) was dropwise to above suspension at about 10-15° C. The mixture solution was stirred at room temperature for 12 h and the pale crystal was filtered. The filtrate was reduced to the minimum under vacuum and the white crude product was recrystallized in methanol, filtered, and dried in vacuo (yield 29.86 g, 24.55%). $^1$H NMR(300 MHz, CDCl$_3$): δ 6.98 (s 2H).

2,5-dibromo-1,4-dihexyloxybenzene. A suspension of KOH powder (10.47 g, 186.6 mmol) in dried DMSO (360 mL) was degassed under vigorous stirring for 1 h. 2,5-dibromo-1,4-dihydroxybenzene (5 g, 18.66 mol) and 1-bromohexane (5.8 mL, 41.06 mmol) were added and stirred for 12 h. The solution was concentrated and precipitated in water, filtered, washed with methanol. The product was recrystallized in ethanol, dried in vacuo (4.518 g, 55.5%). $^1$H NMR(300 MHz, CDCl$_3$): δ 7.08 (s, 2H), 3.95 (t, 4H), 1.8 (m, 4H), 1.49 (m, 4H). 1.37 (m, 8H), 0.9 (t, 6H).

2,5-(1,4-dihexyloxyphenyl)diboronic acid (2). 2,5-dibromo-1,4-dihexyloxybenzene (2 g, 4.58 mmol) was dissolved in ethyl ether (20 mL) and Butyl-Lithium (2.5 M in hexane, 5.05 mL) was added and stirred at room temperature for 12 h under argon gas. Triisopropylborate (2.3 mL, 10.05 mmol) was added at −40° C. and stirred over night from −40° C. to room temperature. The reaction was quenched by the addition of HCl 2M solution (50 mL) and the resulting precipitation was collected, washed with water, ethyl ether, and dried under vacuo (yield 0.53 g, 31.61%). $^1$H NMR (300 MHz, CDCl$_3$): δ 7.16 (s, 2H), 3.95 (t, 4H), 1.68 (m, 4H), 1.8 (m, 4H), 1.25 (m, 8H), 0.85 (t, 6H).

Scheme S.2 Synthesis of
2,5-(1,4-dihexyloxyphenyl)diboronic acid (2)

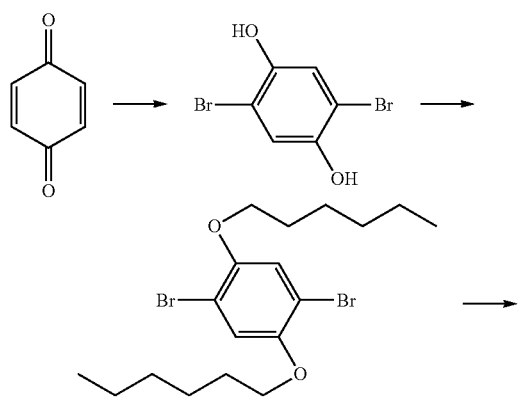

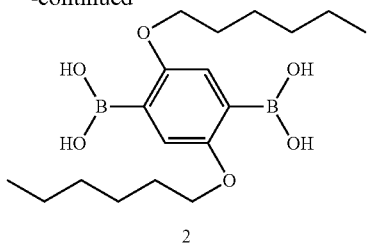

2 t-Boc benzoxazole oligomer. The oligomerization was carried out between (1) and (2) (see molecules in Schemes S.1 and S.2). (1) (0.3 g, 0.8 mmol), (2) (0.148 g, 0.4 mmol), and palladium catalyst (5 mol %) were placed in a two-necked round bottom flask charged with 7 mL of THF under argon. 1 M Na$_2$CO$_3$ solution was added and stirred for 48 h at 80° C. After cooling, the reaction mixture was poured into methanol. The precipitates were isolated by filtration and washed with DI water and methanol and dried under vacuo. $^1$H NMR (300 MHz, CDCl$_3$): δ 8.56 (s, 2H), 7.78 (m, 4H), 7.58 (m, 2H), 7.36 (m, 6H), 7.06 (s, 2H), 3.98 (t, 4H), 1.7-1.2 (m, 16H), 0.78(t, 6H).

Benzoxazole oligomer. The t-Boc benzoxazole oligomer was dissolved in chloroform (3 mL) and trifluoreacetic acid (2 mL) was added. After stirring for 12 h, solvents was removed by evaporation and dried under vacuum oven (yield 0.217 g). $^1$H NMR (300 MHz, CDCl$_3$): δ 11.55 (s, 2H), 8.35 (s, 2H), 7.79-7.68 (m, 4H), 7.62 (m, 2H), 7.41 (t. 4H), 7.2 (d, 2H), 7.06 (s, 2H), 3.99 (t, 4H), 1.78-1.23 (m, 16H), 0.78 (t, 6H).

Scheme S.3. Synthesis of DBO

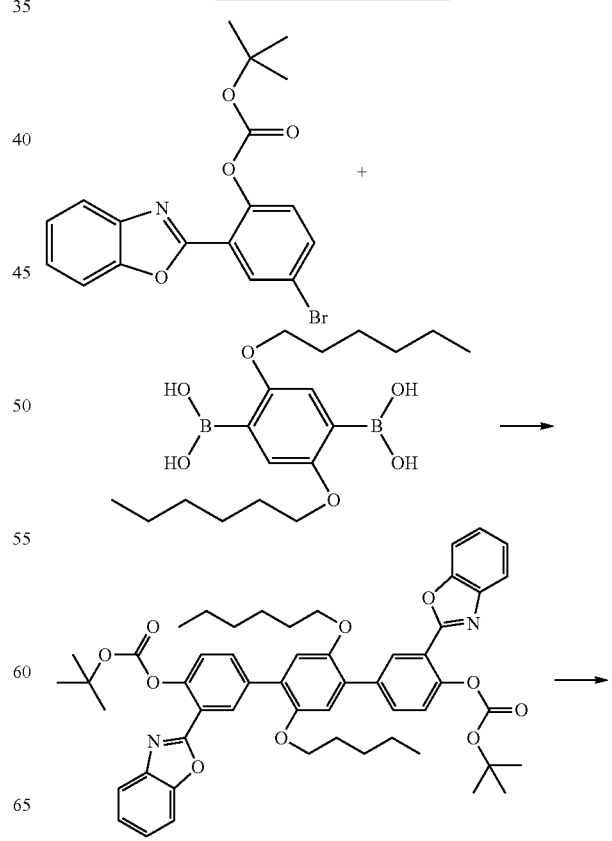

Synthesis of PDA molecules includes the following aspects. The diacetylene monomers were prepared by coupling N-hydroxysuccininic esters of PCDA. A typical procedure for the preparation of PCDA-ABA and PCDA-biotin is as follows.

PCDA-NHS: To a solution containing 1.00 g (2.67 mmol) of 10,12-pentacosadiynoic acid in 10 mL of methylene chloride, was added 0.38 g (3.47 mmol) of N-hydroxysuccinimide and 0.38 g (4.01 mmol) of N-(3-Dimethylaminopropyl)-N'-ethylcarbodiimide hydrochloride at room temperature. The resulting solution was stirred at room temperature for 2 h. The solvent was removed in vacuo and the residue purified by extraction with ethyl acetate to give 1.08 g (86.2%) of the desired diacetylene monomer PCDA-NHS as a white solid. $^1$H NMR (300 MHz, CDCl$_3$): δ 0.85 (t, 3H), 1.20-1.62 (m, 36H), 2.21 (t, 4H), 2.60 (t, 2H), 2.85 (s, 4H), 7.18 (brs, 1H).

PCDA-ABA: To a solution containing 0.56 g (0.50 mmol) of 4-aminobutylic acid in 5 mL of tetrahydrofuran, was added 0.25 g (2.55 mmol) of tri-ethylamine, and 1 mL of di-water was added to dissolve completely at room temperature. PCDA-NHS 0.20 g (0.42 mmol) in 5 mL of tetrahydrofuran was added dropwise to a mixture solution. The resulting solution was allowed to stir for overnight at room temperature. The solvent was removed in vacuo and the residue was purified by extraction with methylene chloride. The organic layer was dehydrated with MgSO$_4$ and recrystallized in methylene chloride to give 0.15 g (77.6%) of the desired diacetylene monomer PCDA-ABA as a pale blue solid. $^1$H NMR (300 MHz, CDCl$_3$): δ 0.85 (t, 3H), 1.20-1.62 (m, 36H), 1.86 (q, 2H), 2.21-2.38 (m, 8H), 3.35 (t, 2H), 7.28 (brs, 1H).

PCDA-EDEA: To a solution containing 1.055 mL (7.21 mmol) of 2,2'-(ethylenedioxy)bis(ethylamine) in 60 mL of methylene chloride, was added dropwise 1.00 g (2.12 mmol) of PCDA-NHS for 3 h at room temperature. The resulting mixture was allowed to stir for 2 h at room temperature. The resulting mixture was concentrated in vacuo, and the residue was purified by column chromatography (9:1 chloroform:methanol) to give 0.51 g (46.7%) as a white solid. $^1$H NMR (300 MHz, CDCl$_3$): δ 0.89 (t, 3H), 1.27-1.76 (m, 35H), 2.23 (m, 6H), 2.91 (t, 2H), 3.42-3.63 (m, 12H), 6.21 (t, 1H), 7.27 (brs, 1H).

PCDA-biotin: To a solution containing 0.23 g (0.94 mmol) of biotin in 5 mL of DMF, was added dropwise 0.40 g (0.79 mmol) of PCDA-EDEA in 5 mL methylene chloride. The mixture solution was allowed to stir for overnight at room temperature. The solvent was removed in vacuo, and the residue was purified by column chromatography (9:1 chloroform:methanol) to give 0.18 g (33.9%) of the desired diacetylene monomer PCDA-EDEA-biotin as a white solid. $^1$H NMR (300 MHz, CDCl$_3$): δ 0.89 (t, 3H), 1.27-1.76 (m, 41H), 2.23 (m, 8H), 2.74 (d, 1H), 2.94 (m, 1H), 3.17 (m, 1H), 3.42-3.65 (m, 13H), 4.32 (q, 1H), 4.54 (q, 1H), 4.92 (s, 1H), 5.87 (s, 1H), 6.27 (t, 1H), 6.31(t, 1H), 7.27 (brs, 1H).

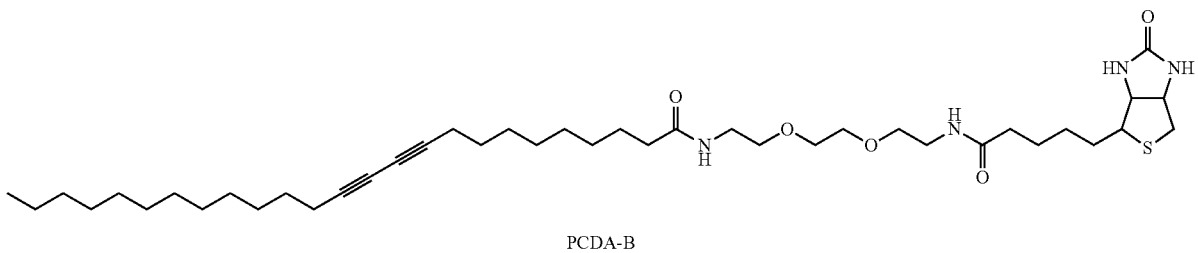

PCDA-B

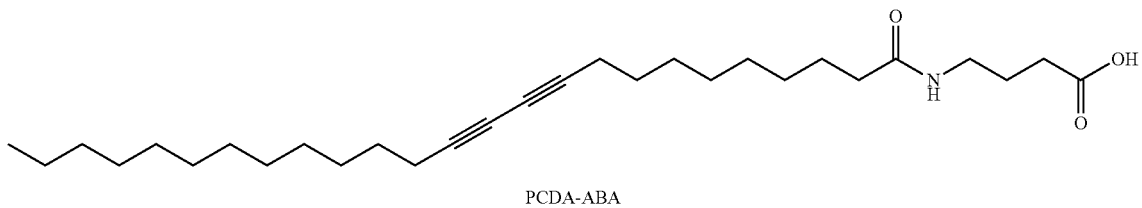 [SMILES: CCCCCCCCCCCCC#CC#CCCCCCCCCC(=O)NCCCC(=O)O]

PCDA-ABA

Characterization was performed as follows. UV/Vis absorption spectra were obtained using a Cary50 (Varian) and the photoluminescence spectra and the absolute quantum efficiency were collected with QM4 (PTI, Inc) equipped with an integrating sphere and a Nitrogen dye laser. Fluorescence images were taken with an Olympus BX51 fluorescence microscope. The size of the vesicles was measured with scanning electron microscopy.

Excitation spectrum of DBO nanoparticles was determined as follows. 10 μM DBO in THF solution shows its large Stokes' shift at 518 nm by maximum excitation of 340 nm. Nanoaggregates in a THF:H$_2$O (1:9) mixture show red shift of the excitation and absorption by 40 nm. The aggregate dispersed in well defined PCDA vesicle structure shows two distinct absorption and excitation at 320 nm and 370 nm; the latter is from the red shift of the syn-enol species and the former is from the anti-enol species. To check the photo stability, the DBO-PCDA was exposed with 254 nm UV for 30 min. 6 W UV lamp was held 1 cm above the sample. There is 15% decrease in the photoluminescence, but it still holds its emissive nature. And the lifetime measurement was done to check the fluorescence decay lifetime of the DBO.

FIG. 16 graphically depicts the excitation (dotted lines) and emission (solid lines) spectra of DBO in THF solution (bottom dotted and solid lines), dispersion in deionized water (middle dotted and solid lines), and dispersion in diacetylene liposome (top dotted and solid lines). The concentrations of DBO were 10 μM. There is red shift for the nanoparticles in THF/H$_2$O mixture. The anti-enol species (320 nm) formation is seen for the DBO-PCDA vesicle.

FIG. 17 graphically depicts UV irradiation of DBO nanoparticles in THF/H$_2$O mixture. 6 W 254 nm UV was illuminated 1 cm above the suspension. The black solid lines are before UV irradiation and the red dotted lines were obtained after 30 min of exposure.

FIG. 18 graphically depicts the fluorescence lifetime of DBO in THF solution (red+), dispersion in THF:H$_2$O (1:9) v/v mixture (blue open squares), and dispersion in diacetylene liposome (black open triangles) observed at 380 nm excitation wavelength. Lifetime measurement was also done at 310 nm excitation for the DBO-PCDA nanoparticles (solid black squares). Instrument response function is plotted as the dotted line.

Example 3

Polydiacetylene Liposome Microarrays for Selective and Sensitive Mercury (II) Detection PDA microarrays are designed for selective and sensitive mercury detection. Mercury (Hg$^{2+}$) is a well-known neurotoxin, and its accumulation in the human body induces critical brain damage, resulting in blindness, deafness, memory loss, and death. Therefore, the allowable concentration of mercury in drinking water is strictly regulated to be less than 2 ppb. To detect mercury, various methods have been developed by means of gold nanoparticles, fluorophores, DNAzymes, proteins, and polymers. The present sensory PDA microarrays were developed based on self-assembling diacetylene molecules having an epoxy group to achieve a universal PDA platform for convenient post-tethering of receptors. The epoxy group provides a versatile functional group for bioconjugation with biological molecules by means of its reaction with seemingly ubiquitous amine groups found on biological molecules; e.g. proteins. Epoxy groups are also stable for storage. N-hydroxysuccinimide (NHS)-activated carboxylic acid can be used for immobilization of PDA liposomes on an amine-modified substrate, and an amine is used for immobilization of an aldehyde-modified substrate. The immobilization efficiency and the stability of the epoxy group are compared with those of NHS-activated carboxylic acid and ethylenediamine, PCDA (10,12-pentacosadiynoic acid)-epoxy is synthesized as described below. The self-assembled diacetylene liposomes (epoxy liposomes) were prepared using a 4:1 mixture of the PCDA-epoxy and PCDA. The two control liposomes were composed of a 1:1 mixture of PCDA: PCDA-linker-NHS (NHS liposome) and a 1:1 mixture of PCDA-EDEA:PCDA-EDA (EDA liposome). The epoxy and NHS liposomes were immobilized on an amine-modified glass substrate and the EDA liposome on an aldehyde-modified glass substrate, respectively, using identical conditions. The results show that PCDA-epoxy liposomes have much faster immobilization kinetics, and result in better film quality and better stability than the other two.

Selective and sensitive PDA microarrays can be developed for mercury detection based on the epoxy liposome system. FIG. 19 illustrates the design strategy for one embodiment. Note that the epoxy units were used for liposome tethering onto the substrate and for the post-tethering of the ssDNA aptamer as a selective receptor for mercury detection. The thymine-rich ssDNA aptamer of SEQ ID NO: 2 (5'-TTCTTTCTTCCCCTTFTTTGTT-3') forms a thymine-Hg$^{II}$-thymine complex (T-Hg-T) by selective binding with Hg$^{2+}$. As schematically illustrated in FIG. 19, the PDA mercury sensors are designed in such a way that when the ssDNA aptamers recognize and wrap around mercury ions, the resulting bulky T-Hg-T complexes repulse each other. The static repulsion force is then transferred to the PDA liposomes to perturb their conjugated ene-yne backbone, and produces the color change from blue to red and the red fluorescence emission.

The PCDA-Epoxy/PCDA (4:1) liposome solution was first immobilized onto an amine glass slide. The thymine-rich ssDNA aptamer is then spotted using a microarrayer onto the liposome layer and the slide is incubated at room temp for 3 h under 70% humidity to prevent the aptamer-solution from drying out. After rinsing away any unreacted ssDAN aptamers, the liposome slide is photopolymerized using a 254 nm UV lamp (1 mW/cm$^2$) for 20 s.

First, the sensitivity of the PDA microarray was tested, FIG. 20 shows the fluorescence microscopy images of the PDA microarray after incubation with H$^{2+}$ solution in various concentrations at room temperature for 1 h. The developed red-fluorescence intensity has a close relationship with the concentration of the mercury solution, and the correlation is shown in FIG. 20D. As the concentration of mercury ions increases, more T-Hg-T complexes are formed, and induce stronger perturbation of the ene-yne backbone of the PDA liposomes, resulting in the increase in the red fluorescence intensity. Based on the correlation curve, therefore, a quantitative analysis of an unknown mercury concentration is also achievable. The detection limit after 1 h of incubation confirmed by microscopy images was about 0.005 mM (about 0.027 mg/20 mL). This detection limit is imposed by the microscope employed and the limit could likely be better if a more sensitive instrument was used.

A detection study was also conducted with the PDA liposome in solution to better understand the recognition of Hg$^{2+}$ by the ssDNA aptamer. FIG. 21 shows the UV-vis absorption and PL emission spectra of the PDA-liposome solution upon addition of mercury (Hg$^{2+}$) ions at room temperature. The absorption peak at 650 nm decreased and the red-phase absorption band appeared upon addition of 0.03 mM of Hg$^{2+}$ (FIG. 21A). The fluorescence intensity of the PDA liposomes also increased upon addition of Hg$^{2+}$ (FIG. 21B). Interestingly, after 2 h incubation, the UV-vis spectrum showed a bathochromic shift, as shown in FIG. 2A, and the PDA liposomes formed an aggregate. Unlike the PDA liposomes in the solid microarray, the PDA liposomes in solution have freedom of translational movement. Therefore, the thymine-rich ssDNA liposome in solution can form intermolecular as well as intramolecular T-Hg-T complexes, as schematically illustrated in FIG. 21C. The formation of the intermolecular T-Hg-T complexes is the likely origin of the observed aggregation and the slight bathochromic shift in UV-vis spectrum.

The selectivity of the PDA microarray was investigated by incubating various metal ions, such as Cd$^{2+}$, K$^+$, Na$^+$, Sn$^{2+}$, Ir$^{2+}$, Cu$^{2+}$, and Zn$^{2+}$, with the PDA microarray. As can be seen in panels A and B of FIG. 22, the fluorescence-emission intensity induced by other metal ions are orders of magnitude smaller than that induced by the same concentration of mercury ion, demonstrating the excellent selectivity of the PDA-liposome array.

In summary, PDAliposome-based microarrays were developed for selective and sensitive mercury detection. The epoxy group is a proven example of a universal functional group for efficient immobilization of PDA liposomes onto a solid substrate, and for the convenient post-tethering of an affinity component such as the amine-modified ssDNA aptamer SEQ ID NO: 2 (5'-TTCTTTCTTCCCCTTGTTT-GTT-3') on the liposome surface as a selective receptor for the recognition of mercury ion. The PDA mercury sensors are designed in such a way that when the ssDNA aptamers recognize and wrap around mercury ions, the steric repulsion between the resulting bulky T-Hg-T complexes perturbs the conjugated ene-yne backbone of the PDA liposomes, and produces the color change from blue to red and the red fluorescence emission. The detection limit of the PDA microarray with the equipment employed is about 5 mM. The specificity of the ssDNA aptamer toward $Hg^{2+}$ provides excellent selectivity to the PDA microarray as well. The epoxy-based PDA liposome design is an excellent universal PDA platform that can be readily applicable to other sensor designs, allowing fast formation the PDA-liposome layer and efficient tethering of an affinity component after liposome immobilization on a substrate for both convenience and to allow for user-prepared microarrays.

The following materials and methods were employed.

Materials: Glass slides used as a solid substrate for the array were cleaned with chloroform, acetone, and 2-propanol for 5 mins each. The pre-cleaned glass slides were sonicated in sulfuric acid containing no-chromix. After thorough rinse with deionized water and dry, the glass slides were treated with 2 wt % 3-aminopropyltriethoxysilane in toluene solution for 1 hour and baked at 130° C. for 30 min. The glass slides were sonicated in toluene, toluene:methanol (1:1) and methanol for 3 mins each to remove any unbound silane monomer.

Preparation of the Liposomes: A mixture of the PCDA-Epoxy and PCDA (4:1 mole ratio) was dissolved in 0.2 mL of tetrahydrofuran. The mixture solvent was injected into 5 mM HEPES buffer at pH 8.0 (30 mL) and bath sonicated for 5 min to give the final concentration of the lipid vesicle of 0.5 mM. After the sonication, the solution was filtered through 0.8 µm cellulose syringe filter 3 times to remove liposomes of undesired size and stored at 5° C. for 2 hours.

Immobilization of the Liposomes: An amine-modified glass slide was incubated in the PCDA-Epoxy/PCDA (4:1) liposome solution for 20 min at room temp. The PDA liposome immobilized glass slide was vigorously rinsed using 10 mM HEPES buffer pH 8.0 for 3 min. The liposome immobilized glass was then dried and stored under nitrogen at 5° C. PCDA-EDEA/PCDA-EDA (1:1) and the PCDA-linker-NHS/PCDA(1:1) liposome were immobilized.

Fabrication of the PDA Microarray: 100 µM of ssDNA in 5 mM HEPES buffer pH 9.5/3×SSC Buffer (1:1) was prepared. The ssDNA probe solution was then heated at 90° C. for 3 min. Thymine rich ssDNA was spotted onto the glass slide coated with the PDA liposomes using a manual microarrayer (VP 475, V&P scientific, Inc.) at 70% humidity. The glass slide with the spotted ssDNA was incubated for 6 hours at 75% humidity. After rinsing with 1% SDS buffer pH 8.0 for 3 mins and deionized water, the slide was dried under a stream of nitrogen followed by the photopolymerization with 254 nm UV light (1 mW/cm²) for 20 sec.

Fluorescent Microscope Images: The liposome microarray was incubated with a solution containing various concentrations (0.005, 0.01, 0.050, 0.10, 0.50, and 1 mM; i.e., 1-130 ppm) of $Hg^{2+}$ for 1 hour. The fluorescence images were obtained by using a fluorescent microscope (Olympus BX51 W/DP71). The excitation wavelength was 600 nm. The data were obtained with five independent experiments. The error bar is standard deviation and each point represents the mean value. Other metal ions concentration and incubation time were the same as the $Hg^{2+}$ incubation protocol.

Preparation of the Diacetylene Liposome having the Thymine-rich ssDNA Aptamer: To the 200 µL of 0.5 mM of PCDA-Epoxy/PCDA (4:1) liposome solution was added 100 µL (70 nmol) of the amine-modified thymine-rich ssDNA at 10° C. The reaction mixture was stirred and stored in an incubator at 37° C. for 4 hours. The resulting reaction mixture was sonicated for 10 min and cooled at 5° C. for 4 hours. The unbound ssDNA was removed through dialysis (Slide-A-Lyzer Dialysis Cassette, 20,000 MWCO, 0.1-0.5 mL capacity) in deionized water.

Mercury Detection with the PDA Liposome in Solution: To a solution containing 100 µL of 0.05 mM solution of the PDA liposome having the thymine-rich ssDNA, was added 50 µL of concentrated $Hg^{2+}$ solution to make the final concentration of 0.03 mM at room temperature. UV-vis and PL spectra were taken after 1 and 2 hours incubation at room temperature.

The following materials and methods were employed. All solvents were purchased from Sigma-Aldrich Chemicals. 10,12-pentacosadiynoic acid (PCDA) was purchased from GFS Chemicals. 2-(2-Aminoethoxy)ethanol, N-hydroxysuccinimide (NHS), 1-ethyl-3-[3-dimethylaminopropyl]carbodiimide hydrochloride (EDC), and succinic anhydride (SA), metal ions ($CdCl_2$, KCl, NaCl, $IrCl_2$, $SnCl_2$, $CuCl_2$, $ZnCl_2$, $HgCl_2$) were purchased from Sigma-Aldrich Chemical Co. The amine-modified thymine-rich ssDNA SEQ ID NO: 2 (5'-TTCTTTCTTCCCCTTGTTTGTT-3') oligonucleotide was purchased from Integrated DNA Technologies, Inc. Dialysis membranes were purchased from pierce (Slide-A-Lyzer Dialysis Cassette, 20,000 MWCO, 0.1-0.5 mL capacity). The gene frame for the liposome immobilization was purchased from Fisher Scientific. ¹HNMR spectra (500 MHz) were obtained from Varian Inova 500 NMR instrumentation. UV/Vis absorption spectra were taken on a Varian Cary50 UV/Vis spectrophotometer. Fluorescence spectra were obtained using a PTI QuantaMaster™ spectrofluorometer equipped with an integrating sphere. Fluorescence images were taken using an Olympus BX51 W/DP71 fluorescent microscope.

Synthesis of PCDA derivatives was as follows. The diacetylene monomer PCDA-epoxy was synthesized according to the reaction scheme shown in FIG. 23. With reference to FIG. 23, monomer synthesis included: (a) N-hydroxysuccinimide, N-(3-Dimethylaminopropyl)-N'-ethylcarbodiimide hydrochloride, methylene chloride, 25° C., 2 hours; (b) 2-(2-Aminoethoxy)ethanol, methylene chloride, 25° C., 3 hours; and (c) Epibromohydrin, sodium hydroxide, tetrahydrofuran, 15° C., overnight.

PCDA-NHS: To a 10 mL of methylene chloride solution containing 2.00 g (5.34 mmol) of 10,12-pentacosadiynoic acid (PCDA), was added 0.76 g (6.94 mmol) of N-hydroxysuccinimide and 0.76 g (8.02 mmol) of 1-ethyl-3-[3-dimethylaminopropyl]carbodiimide hydrochloride at room temperature. The resulting reaction mixture was stirred at room temperature for 2 h. The solvent was removed in vacuo, and the residue was purified by extraction with ethyl acetate to give 2.16 g (86.2%) of the desired diacetylene monomer PCDA-NHS as a white solid: ¹H NMR (500 MHz, $CDCl_3$): δ 0.86 (t, 3H), 1.21-1.52 (m, 36H), 2.21 (t, 4H), 2.60 (t, 2H), 2.87 (s, 4H).

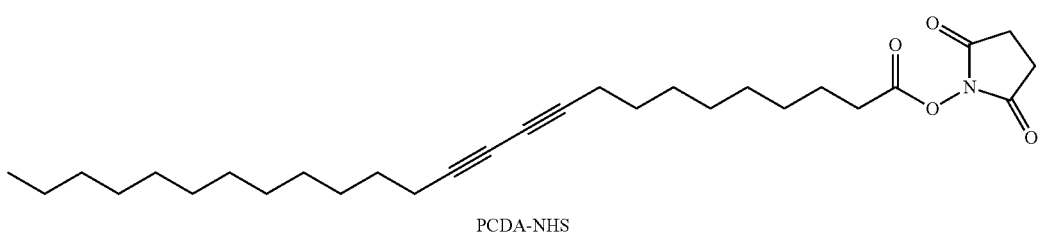 [SMILES: CCCCCCCCCCCCC#CC#CCCCCCCCCC(=O)ON1C(=O)CCC1=O]

PCDA-NHS

PCDA-Ethoxy-ethanol: To a 100 mL of methylene chloride solution containing 1.60 g (15.26 mmol) of 2-(2-aminoethoxy)ethanol was added dropwise 2.40 g (5.08 mmol) of PCDA-NHS in 50 mL of methylene chloride. The resulting reaction mixture was stirred for 3 h at room temperature and filtered. The solvent was removed from the filtrate was by applying vacuum. The residue was extracted with methylene chloride and washed with brine 3 times. The residue was further purified by recrystallization in methylene chloride to give 0.55 g (77.6%) of the desired diacetylene monomer PCDA-Ethoxy-ethanol as a white solid: $^1$H NMR (500 MHz, CDCl$_3$): δ 0.85 (t, 3H), 1.22-1.52 (m, 36H), 2.22 (m 6H), 3.44 (q, 2H), 3.55 (q, 4H), 3.72 (q, 2H), 5.81 (s, 1H).

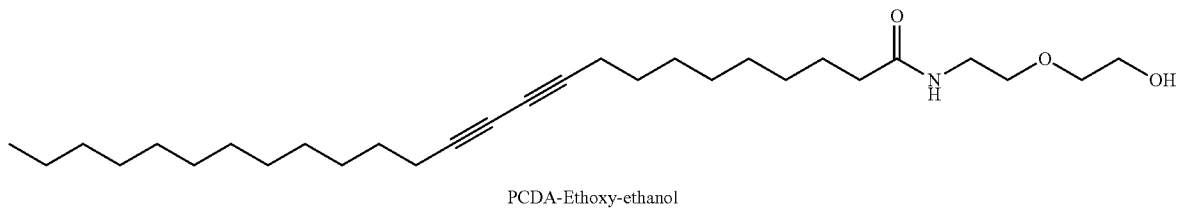 [SMILES: CCCCCCCCCCCCC#CC#CCCCCCCCCC(=O)NCCOCCO]

PCDA-Ethoxy-ethanol

PCDA-Epoxy: 0.10 g (4.24 mmol) of sodiumhydride was suspended in 10 mL tetrahydrofuran at 5° C. To the suspension was added dropwise 1.00 g (2.16 mmol) of PCDA-Ethoxy-ethanol in 20 mL anhydrous tetrahydofuran for 15 min and the reaction mixture was stirred for 4 h at room temperature. To the mixture solution was added 0.50 g (3.69 mmol) of epibromohydrin and the reaction mixture was stirred at room temperature for overnight. The resulting reaction mixture was filtered and concentrated in vacuo, and the residue was purified by column chromatography (95:5 chloroform: methanol) to give 0.65 g of the desired diacetylene monomer PCDA-Epoxy (46.7%) as a white solid: $^1$H NMR (500 MHz, CDCl$_3$): δ 0.85 (t, 3H), 1.21-1.58 (m, 37H), 2.16 (t, 6H), 2.57 (q, 1H), 2.77 (t, 1H), 3.14 (m, 1H), 3.43 (m, 3H), 3.52 (t, 2H), 3.59-3.65 (m, 4H), 3.79 (q, 1H), 5.89(s, 1H).

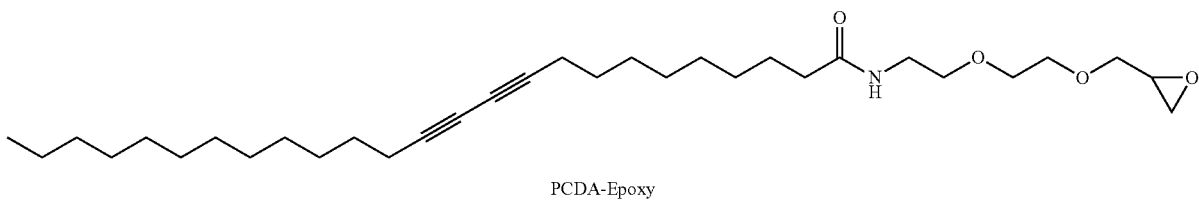 [SMILES: CCCCCCCCCCCCC#CC#CCCCCCCCCC(=O)NCCOCCOCC1CO1]

PCDA-Epoxy

Example 4

Selective and Sensitive Nerve Gas Detection

PDA sensors are designed for selective and sensitive nerve gas detection as follows. Referring now to FIG. 24, a detection mechanism for organophosphate (OP) nerve gas agent is shown. Design principles of the PCDA derivative include the oxime derived PCDA monomers:

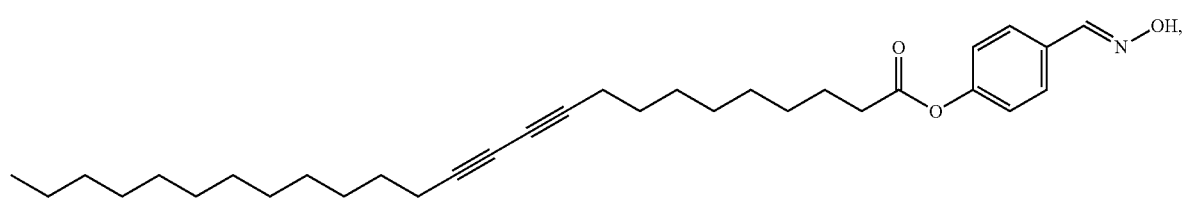

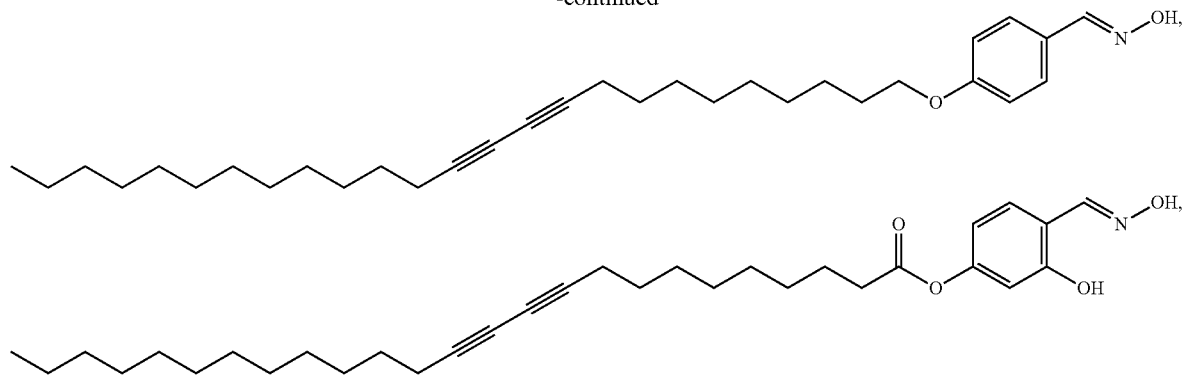

where the oxime reacts with OP agent faster by α-effect. For example, the oxime unit can bind with nerve gas simulants such as diisopropyl fluorophosphate (DFP) and diethyl chlorophosphate (DCP).

Design principles also include the aldehyde derived PCDA monomers:

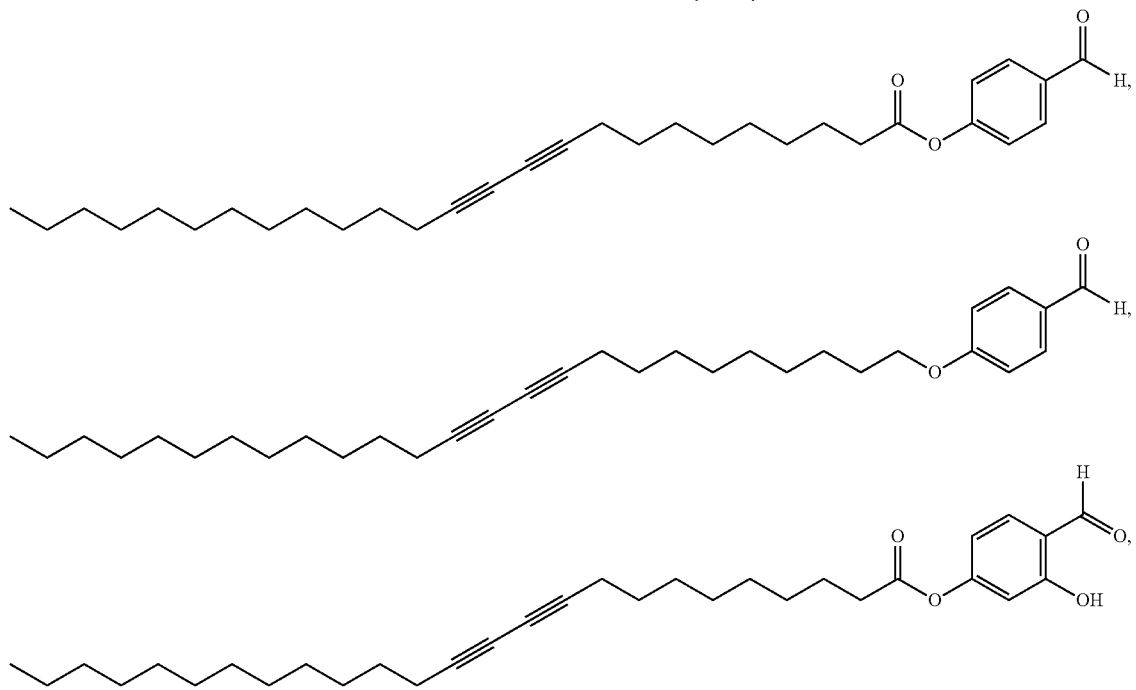

where the aldehyde derived PCDA monomer is stable for other acids and is sensitive for external stress. These benzaldehyde PDA derivatives increase the sensitivity when mixed with the oxime derived PDA monomers. The aldehyde PDA monomers show very sensitive color changes at about 30° C. to about 40° C. compared to about 60° C. to about 70° C. for other PDA molecules.

Liposomes and gels of liposomes were prepared using these monomers and mixtures of these monomers. The following sets of liposome samples (1:1 ratio) were made:
1. PCDA-hydroxy-oxime
   PCDA-hydroxy-aldehyde
2. PCDA-hydroxy-oxime
   PCDA-aldehyde
3. PCDA-oxime
   PCDA-hydroxy-aldehyde
4. PCDa-oxime
   PCDA-aldehyde
5. PCD-oxime
   PCDA-hydroxy-aldehyde
6. PCD-oxime
   PCDA-aldehyde
7. PCDA-hydroxy-oxime
   PCD-oxime Preparation of liposome gel samples included the following: 1. 1 wt % of agarose added to 0.5 mM of liposome solution. 2. Agarose and Liposome mixture was sonicated and mildly heated. 3. The solution was cooled for 1 hr.

The final concentration of liposome was 0.5 mM for 3-4 and 0.25 mM for 1-2. Detection time for the solution test: 5 sec for liposome solution and 10 min for liposome gel. Detection time for the vapor test: 10 min for liposome gel. PCDA-Hydroxy-Aldedyde and PCDA-Aldehyde was used for each oxime derived PCDA samples as a pair. Solution and gels formulations of the liposomes were able to detect OP.

FIG. 25 shows the results of liposome gel testing for the OP nerve gas simulants DCP and DFP and for other acids to demonstrate the selectivity and sensitivity. Fluorescence shift from blue to red can be seen for the gels exposed to DCP and DFP.

Example 5

Selective and Sensitive Melamine Detection

PDA sensors are designed for selective and sensitive melamine detection as follows.

Ingestion of melamine may lead to reproductive damage, or bladder or kidney stones, which can lead to bladder cancer. The European Union set a standard for acceptable human consumption of melamine at 0.5 milligrams per kg of body mass, Canada declared a limit of 0.35 mg and the US FDA's limit was put at 0.63 mg, but was later reduced to 0.063 mg daily. The World Health Organization's food safety director estimated that the amount of melamine a person could stand per day without incurring a bigger health risk, the "tolerable daily intake" (TDI), was 0.2 mg per kg of body mass. Melamine adulteration has been a problem in animal feed and protein products, including dairy products.

The following PDCA monomers were used:

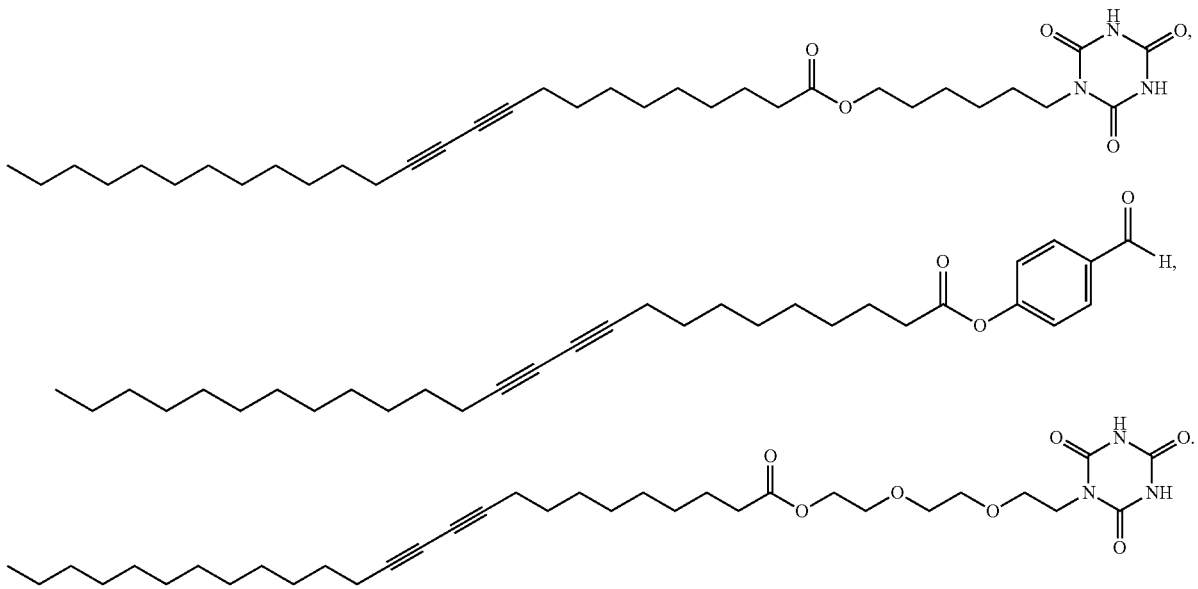

Liposome preparation methods include the following.

Thin Film method: Dissolve the monomer to Chloroform; Add the 5 mM HEPES buffer pH 8; Agitate at 80° C. for 15 min.; Sonicated for 15 min at 80° C.; Filtered using 0.8 um syringe filter; Cool down for 4 hr.

Injection Method: Dissolve the monomer to THF; Inject the solution to 5 mM HESPES buffer; Sonicated for 15 min at 80° C.; Filtered using 0.8 um syringe filter; Cool down for 4 hr.

Dropping Method: Dissolve the monomer to DMSO; Drop the solution to 5 mM HESPES buffer at 80° C.; Sonicated for 15 min at 80° C.; Filtered using 0.8 um syringe filter; Cool down for 4 hr.

Using the various monomers, it was observed that the long hydrophobic chain near the affinity group is not good for liposome formation when mixed with other monomers because of a hydrophilic and hydrophobic mismatch. The better liposome formation, the stronger the blue color intensity. The blue color intensity is an indicator of polymerization rate. Of the monomers shown above, the monomer including the ether groups:

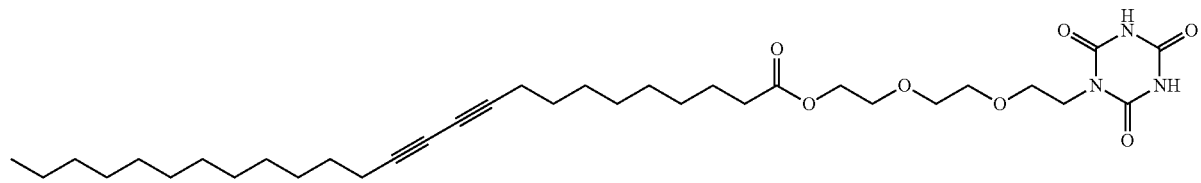 [SMILES: CCCCCCCCCCCCC#CC#CCCCCCCCCC(=O)OCCOCCOCCn1c(=O)[nH]c(=O)[nH]c1=O]

demonstrated better liposome formation.

Referring now to FIG. 26, a mechanism of color change for the polydiacetylene melamine sensor is shown. Strong inter- and intramolecular hydrogen bonds can form with the sensor(s) and melamine to produce a color change.

FIG. 27 shows the UV spectrum change of PCDA liposomes following addition of different amounts of melamine.

FIG. 28 shows the visible color change upon addition of various amounts of melamine. Solutions are shown contained in cuvettes. In particular, a color change is noticeable following addition of melamine at 1 ppm in comparison with the PCDA liposomes without melamine. This demonstrates the sensitivity of the sensor using just the naked eye.

FIG. 29 demonstrates the selectivity of the PCDA liposomes for melamine as compared to thymine, cytosine, and uracil. Visible color change is observed for melamine only as 40 ppm of thymine, cytosine, and uracil each fails to change the color.

Example 6

PDA Monomer for a Sensitive Conductive Sensor

The following PDA monomer was used to make a sensor that provides a good measurable change in conductivity:

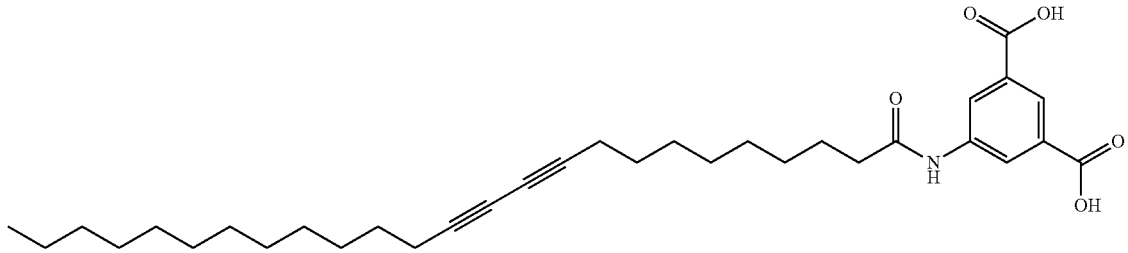 [SMILES: CCCCCCCCCCCCC#CC#CCCCCCCCCC(=O)Nc1cc(C(=O)O)cc(C(=O)O)c1]

Conductivity changes are very sensitive to external stimuli for the p-conjugated polymer. A single p orbital can induce a large change in conductivity. Typically, the conducting level of polydiacetylene is low and almost resistive, but isophthalic acid (IPA) derived PDA monomer shows a much higher conductivity. For example, some PDAs may have conductivities in the microampere range whereas the present monomer shows conductivity between about 1 to about 40 milliamperes. This monomer can be used to make very sensitive wire sensors.

Referring now to FIG. 30, current (A) versus bias (V) is shown for the PCDA-IPA.

The present technology described in the various embodiments herein provides methods for making and using selective self-signaling analyte sensing microarrays that can be readily applicable to many other chemical and biological sensor applications to allow for highly selective and sensitive quantitative analysis. The embodiments and the examples described herein are exemplary and not intended to be limiting in describing the full scope of apparatus, compositions, systems, and methods of the present technology. Equivalent changes, modifications, and variations of some embodiments, materials, compositions and methods can be made within the scope of the present technology, with substantially similar results.

What is claimed is:

1. A melamine sensor comprising a liposome comprising a plurality of PDA monomers

wherein, $R^1$ is an alkyl group of about twelve carbon atoms;
$R^2$ is an alkyl group of about eight carbon atoms; and
$R^4$ is a member of the group consisting of:

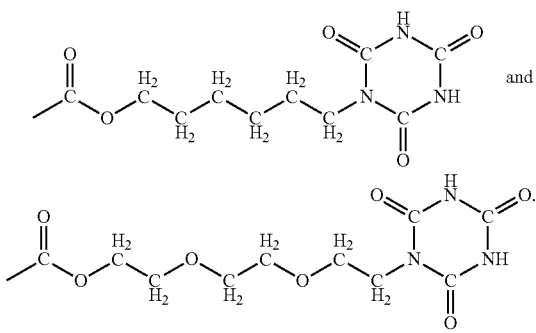

2. An organophosphate sensor comprising a liposome or gel comprising a plurality of PDA monomers

wherein, $R^1$ is an alkyl group of about twelve carbon atoms;
$R^2$ is an alkyl group of about eight carbon atoms; and
$R^5$ is a member of the group consisting of:

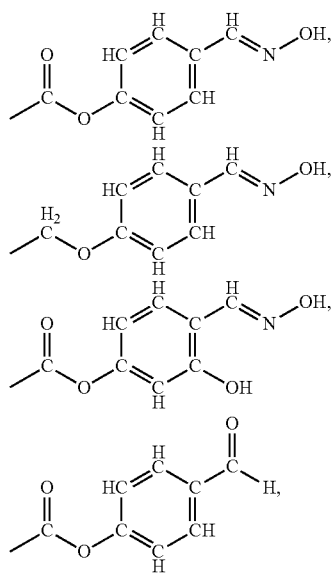

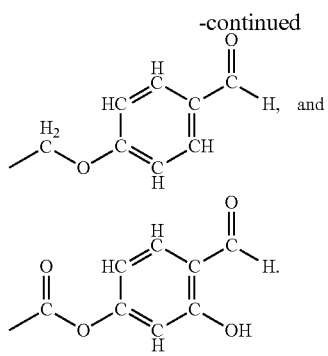

3. The organophosphate sensor of claim 2, wherein the plurality of PDA monomers comprises at least one oxime containing monomer and at least one benzaldehyde containing monomer.

4. A sensor comprising:
 a hydroxyphenyl-benzoxazole (HBO) derivative;
 a plurality of diacetylene monomers, wherein at least a portion of the diacetylene monomers is coupled to a first affinity component having affinity for a first target;
 wherein the sensor exhibits a change in fluorescence or conductivity when the affinity component interacts with the first target.

5. The sensor of claim 4, wherein the HBO derivative comprises 1,4-di(3-(benzoxazol-2-yl)-4-hydroxyphenyl)-2,5-dihexyloxybenzene (DBO).

6. The sensor of claim 4, wherein the plurality of diacetylene monomers comprises 10,12-pentacosadiynoic acid-aminobutyric acid (PCDA-ABA).

7. The sensor of claim 4, wherein the portion of the diacetylene monomers coupled to the first affinity component comprises 10,12-pentacosadiynoic acid-2,2'-(ethylenedioxy)-bis(ethylamide) (PCDA) coupled to the first affinity component.

8. The sensor of claim 4 comprising about a 7:3 mole ratio of diacetylene monomers to the portion of the diacetylene monomers coupled to the first affinity component.

9. The sensor of claim 4 comprising about a 1:50 mole ratio of HBO derivative to diacetylene monomers.

10. The sensor of claim 4, wherein the sensor has a fluorescence quantum yield ($\Phi F$) of about 38%.

11. The sensor of claim 4, wherein the first affinity component is selected from the group consisting of a chemical ligand, antibody, antibody fragment, oligonucleotide, antigen, polypeptide, glycolipid, protein, enzyme, peptide nucleic acid, and polysaccharide.

12. The sensor of claim 4, wherein the first affinity component is biotin.

13. The sensor of claim 4, wherein the sensor is bound to a surface by binding of the first affinity component to the first target, wherein the first target is immobilized on the surface.

14. The sensor of claim 4, wherein the plurality of diacetylene monomers comprises a portion of diacetylene monomers that includes an epoxy group.

15. The sensor of claim 4, wherein the sensor is in the form of a particle.

* * * * *

```
                       SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: ssDNA aptamer for potassium

<400> SEQUENCE: 1
ggttggtgtg gttgg                                                      15

<210> SEQ ID NO 2
<211> LENGTH: 22
<212> TYPE: DNA
<213> ORGANISM: Artificial Sequence
<220> FEATURE:
<223> OTHER INFORMATION: ssDNA aptamer for mercury

<400> SEQUENCE: 2
ttctttcttc ccttgtttg tt                                              22
```